(12) United States Patent
Montclare et al.

(10) Patent No.: US 11,892,449 B2
(45) Date of Patent: Feb. 6, 2024

(54) THERAPEUTICS AND POINT OF CARE LATERAL-FLOW TEST FOR VIRUS AND ANTIBODIES USING TAGGED ASSEMBLED PROTEINS

(71) Applicant: New York University, New York, NY (US)

(72) Inventors: Jin Kim Montclare, New York, NY (US); Farbod Mahmoudinobar, Harrison, NJ (US); Kamia Punia, Staten Island, NY (US); Dustin Robert Britton, Brooklyn, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 18/058,703

(22) Filed: Nov. 23, 2022

(65) Prior Publication Data

US 2023/0280343 A1    Sep. 7, 2023

Related U.S. Application Data

(60) Provisional application No. 63/282,487, filed on Nov. 23, 2021.

(51) Int. Cl.
*G01N 33/569* (2006.01)
*A61P 31/14* (2006.01)
*C07K 14/78* (2006.01)
*G01N 33/543* (2006.01)

(52) U.S. Cl.
CPC ........ *G01N 33/56983* (2013.01); *A61P 31/14* (2018.01); *C07K 14/78* (2013.01); *C12Y 304/17023* (2013.01); *G01N 33/54388* (2021.08); *C07K 2319/50* (2013.01); *G01N 2469/10* (2013.01); *G01N 2469/20* (2013.01)

(58) Field of Classification Search
None
See application file for complete search history.

(56) References Cited

U.S. PATENT DOCUMENTS

2013/0331465 A1* 12/2013 Montclare .............. C07K 14/00
530/402

* cited by examiner

*Primary Examiner* — Suzanne M Noakes
*Assistant Examiner* — Jae W Lee
(74) *Attorney, Agent, or Firm* — Hodgson Russ LLP

(57) ABSTRACT

Provided is a multivalent protein that targets interaction of SARS-CoV-2 spike receptor binding domain (RBD) with the human angiotensin-converting enzyme 2 (ACE2) receptor protein. The multivalent proteins may also be used to treat subjects having cancer and/or a disease and/or viral infection. Also presented is a multiplex lateral flow test strips for simultaneous detection of the virus and viral antibodies.

10 Claims, 20 Drawing Sheets

Specification includes a Sequence Listing.

| Protein | ACE2 | ACE-MAP | ACE-MAP-2 | ACE_BINDER |
|---------|------|---------|-----------|------------|
| IC50 | 1.8 nM | 1050 nM | 488 nM | 1800 nM |

THERAPEUTICS AND POINT OF CARE LATERAL-FLOW TEST FOR VIRUS AND ANTIBODIES USING TAGGED ASSEMBLED PROTEINS

CROSS REFERENCE TO RELATED APPLICATIONS

This application claims priority to U.S. Provisional Application No. 63/282,487, filed on Nov. 23, 2021, the disclosure of which is incorporated herein by reference.

STATEMENT REGARDING FEDERALLY SPONSORED RESEARCH

This invention was made with government support under grant numbers 1644681 and 2031364 awarded by the National Science Foundation and W911NF-19-1-0150 awarded by the Army Research Office. The government has certain rights in the invention.

SEQUENCE LISTING

The instant application contains a Sequence Listing, which has been submitted electronically in XML format and is hereby incorporated by reference in its entirely. The XML copy, created on Nov. 23, 2022, is named "058636_00564_ST26.xml" and is 216,672 bytes.

BACKGROUND OF THE INVENTION

The COVID-19 pandemic caused by severe acute respiratory syndrome coronavirus 2 (SARS-CoV-2) has, since December 2019, caused over million deaths with over 180 million confirmed cases worldwide. Great strides have been made through innovations in rapid testing and neutralizing antibody treatments in an effort to control the spread and fatality of the disease. However, the lack of immediate widespread testing at the beginning of the pandemic has proven fatal. The need for widely available therapies is also clear. If an infected person reaches the stage at which hospitalization is necessary, the COVID-19 patient faces a 21% fatality rate, more than five times greater than that of influenza. Hospitalization has also been linked to higher viral titers in hospitalized patients. In terms of surveillance of the virus, testing of SARS-CoV-2 has relied on specialized instruments in addition to costly reagents and supplies for carrying out the reactions. Low and middle income countries (LMICs) are especially vulnerable since the healthcare infrastructure and resources may not allow for widespread testing. One such proposed solution, lateral flow assays (LFAs) and enzyme-linked immunosorbent assays (ELISA), represent a point-of-care (POC) test for a simple, inexpensive, and fast diagnosis that also predominantly relies on protein-protein interactions (PPIs).

During infection by SARS-CoV-2, the spike (S) protein on the virus surface recognizes the peptidase domain (PD) of the angiotensin-converting enzyme 2 (ACE2) of the host. Structural studies reveal that the N-terminal alpha-helix (residues 1-23) of human ACE2 receptor is critical to binding the S1 receptor binding domain (RBD) of SARS-CoV-2 involved in infection. Recently engineered recombinant ACE2 has shown an increased avidity to SARS-CoV-2 compared to the wild-type. Recombinant ACE2 has also been clinically proven to block early infection and reduce recovery. However, recent studies have also shown that isolation of this alpha-helix as an antibody or protein domain mimic (PDM) provides weak protein-protein interaction with the SARS-CoV-2 RBD.

HIF1α has been the subject of recent research in PPIs because of the high percentage of alpha-helicity at the interface for multiple binding interfaces and when inhibited by helix mimetics, has shown to reduce tumor growth in animal models. Recently, key residues of the C-terminal transactivation (CTAD, aa 786-826) of HIF1α that interact with the cysteine-histidine rich 1 (CH1) domain of the coactivator protein p300 has been mimicked into an effective PDM using the oxopiperazine helix mimetics (OHM) strategy. OHMs employ chemical conjugation of the nitrogen atoms in neighboring backbone amides with an ethylene bridge to create a chiral scaffold to maintain a structure and thus function akin to proteins. This design uses just the twelve CTAD residues with a binding affinity of up to 530 nM—as compared to the full length CTAD of HIF1α with a binding affinity of 38 nM by tryptophan fluorescence assay. The OHM PDM reduces HIF activity and down-regulated the expression of hypoxia-inducible genes and in vivo experiments reduces tumor volume by approximately 50%.

SUMMARY OF THE DISCLOSURE

The present disclosure provides a multivalent protein that targets the interaction of SARS-CoV-2 spike receptor binding domain (RBD) with the human angiotensin-converting enzyme 2 (ACE2) receptor protein and a multivalent protein that targets the interaction of p300 with the hypoxia induced factor 1α (HIF1α). These proteins rely on multi-valency rather than the sensitivity of a monomeric ligand to provide avidity to its target (See FIG. 1). The present protein was obtained by engineering a small ACE2 mimetic tagged assembled protein (ACE-TAP) or multivalent assembled protein (ACE-MAP) to the SARS-CoV-2 spike protein by fusing the N-terminal helix of ACE2 to the coiled-coil domain of the cartilage oligomeric matrix protein (referred to herein as ccCOMP or C protein). HIF1α-MAP (H-MAP) grafts the critical residues of HIF1a to ACE-MAP such that they are solvent exposed. Some properties of the present protein ACE-MAP and H-MAP include exhibiting picomolar binding affinity to the spike RBD and p300 proteins respectively, ability to be expressed in E. coli, thermal stability and relatively small (62 and 75 kDa, respectively in) size. These properties indicate H-MAP and ACE-MAP can be used for both diagnostics and therapeutics to their respective targets. The ACE-MAP may also be referred to as ACE-TAP in this disclosure.

In an aspect, the present disclosure provides molecules (e.g., multivalent assembled proteins (MAPs)) that bind to COVID-19 virus or the p300 peptide, wherein the molecules comprise a plurality of proteins (e.g., 5 proteins). In an embodiment, each multivalent molecule may be a pentamer, wherein each of the monomers (e.g., a protein of the present disclosure) of the pentamer comprise a plurality of blocks. For example, each monomer (e.g., protein) may comprise of one or more $X_1$ blocks, $X_2$ blocks, and $X_3$ blocks, where the $X_1$ block is a coiled-coil domain, the $X_2$ block is a linker, and the $X_3$ block is a binding domain. The blocks may oriented from the N to the C-terminus as $(X_1)_a$-$(X_2)_b$-$(X_3)_c$ where a, b, and c are a number of repeats for that block. a, b, and c, may all be the same, all be different, or two of a, b, and c are the same and remaining one is different. The blocks may also be oriented from C-terminus to N-terminus as $(X_3)_c$-$(X_2)_b$-$(X_1)_a$. Examples of each block are provided herein. A protein may comprise one or more additional blocks. The multivalent molecules are formed by the self-assembling ability of the coiled-coil domain ($X_1$ block) to form oligomers (e.g., trimers, tetramers, and pentamers).

The present disclosure also provides a rapid, simple, and effective point of care (POC) test. Multiplex lateral flow test strips for simultaneous detection of the virus and viral antibodies, including discrimination of antibody subtypes are described. A method using the multiplex lateral flow test strips to detect the virus, the antibodies, or simultaneously the virus and the antibodies is also described. The virus is detected by use of ACE-TAP, while the viral antibodies are detected by using S-TAP. Specific, colorimetrically detectable binding molecules directed against COVID-19 virus and antibodies generated against COVID-19 are also described.

DESCRIPTION OF THE DISCLOSURE

Figure 1:
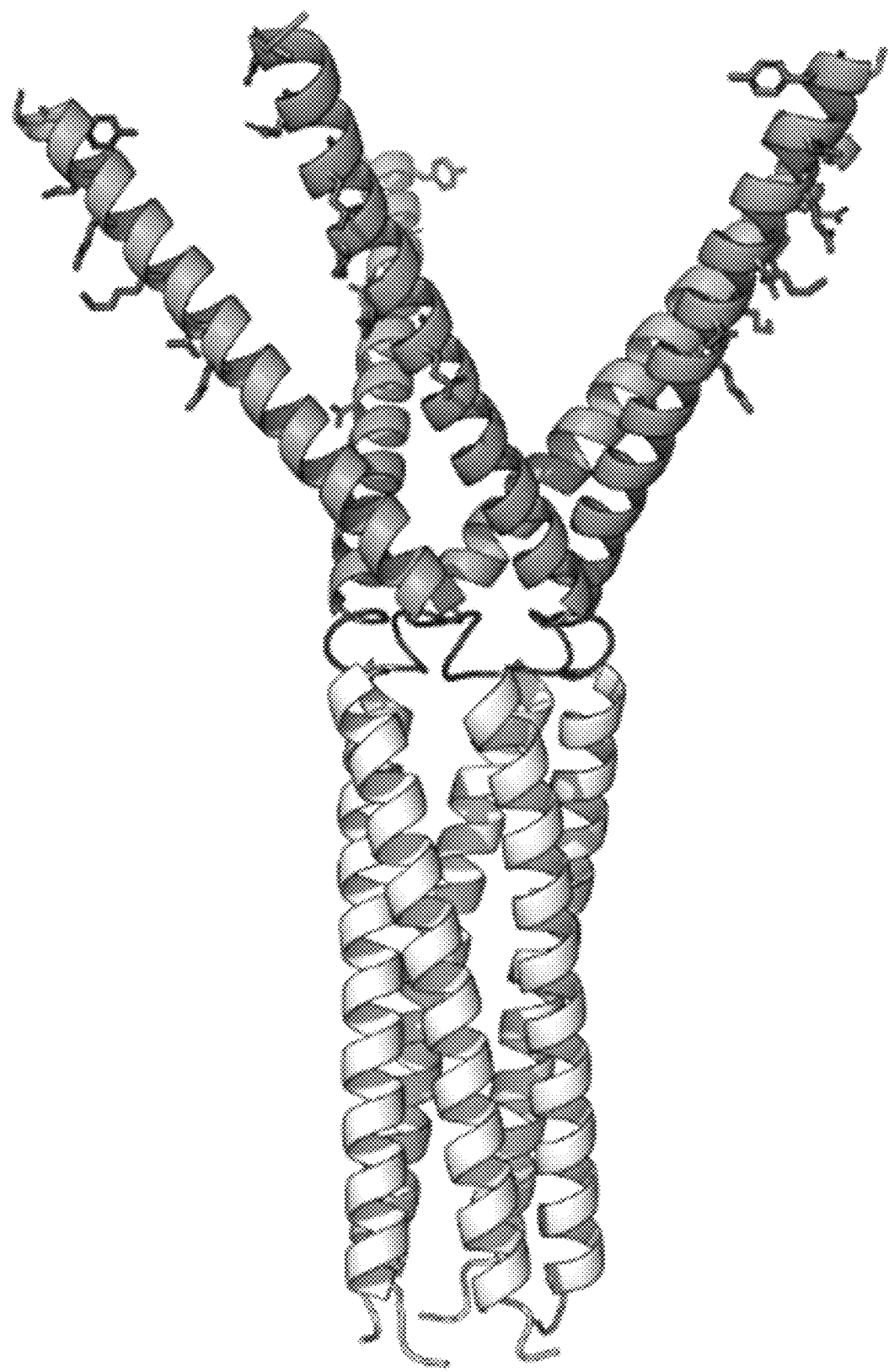
FIG. 1. Cartoon representation of computationally designed ACE-MAP. C, kink, linker and binder protein are shown in white, red, green and cyan color respectively. The residues involved in binding to S-RBD are shown in stick representation and dark blue color.

This disclosure describes a lateral flow assay (LFA) which can be used as a point of care (POC) test for SARS-CoV-2 and therapeutic agents against SARS-CoV-2.

Throughout this application, the use of the singular form encompasses the plural form and vice versa. For example, "a", or "an" also includes a plurality of the referenced items, unless otherwise indicated.

Where a range of values is provided in this disclosure, it should be understood that each intervening value, to the tenth of the unit of the lower limit between the upper and lower limit of that range, and any other intervening value in that stated range is encompassed within the invention, unless clearly indicated otherwise. The upper and lower limits of these smaller ranges may independently be included in the smaller ranges encompassed within the disclosure.

The term "treatment" as used herein refers to alleviation of one or more symptoms or features associated with the presence of the particular condition or suspected condition being treated. Treatment does not necessarily mean complete cure or remission, nor does it preclude recurrence or relapses. Treatment can be effected over a short term, over a medium term, or can be a long-term treatment, such as, within the context of a maintenance therapy. Treatment can be continuous or intermittent.

The term "effective amount" as used herein refers to an amount of an agent sufficient to achieve, in a single or multiple doses, the intended purpose of treatment or administration. The exact amount desired or required will vary depending on the particular compound or composition used, its mode of administration, patient specifics and the like. Appropriate effective amount can be determined by one of ordinary skill in the art informed by the instant disclosure using only routine experimentation.

The term "neutralizing" as used herein in reference to an antibody (e.g., antibody generated as part of a host immune response) refers to antibody or the antigen binding fragment that inhibits SARS-CoV-2 virus from infecting a target cell for replication, regardless of the mechanism by which neutralization may be achieved. For example, the virus may be neutralized by inhibiting the entry of SARS-CoV-2 into host mammalian cells or inhibiting entry of pseudotype viruses displaying the Spike protein of SARS-CoV-2 into host mammalian cells. The term "pseudovirus" refers to recombinant viral particles containing a reporter gene that also expresses the Spike protein of SARS-CoV-2 on its surface.

As used in this disclosure, the singular forms include the plural forms and vice versa unless the context clearly indicates otherwise.

All nucleotide sequences described herein, their RNA and DNA equivalents, and complimentary sequences are included in this disclosure. Disclosure of protein sequences also includes corresponding RNA and DNA sequences encoding for such proteins. While specific sequences are listed in this disclosure, it will be appreciated that amino acid changes/substitutions may be made in the sequences without affecting the function/activity. Such, sequences which are 75%, 80%, 85%, 90%, 95%, 96%, 97%, 98% and 99% identical to the sequences disclosed herein or to the nucleotide sequences encoding the amino acid sequences disclosed herein are considered to be part of the disclosure.

In an aspect, the present disclosure provides molecules (e.g., multivalent assembled proteins (MAPs)) that bind to COVID-19 virus, wherein the molecules comprise a plurality of proteins (e.g., 5 proteins). In an embodiment, each multivalent molecule may be a pentamer, wherein each of the monomers (e.g., a protein of the present disclosure) of the pentamer comprise a plurality of blocks. For example, each monomer (e.g., protein) may comprise of one or more $X_1$ blocks, $X_2$ blocks, and $X_3$ blocks, where the $X_1$ block is a coiled-coil domain, the $X_2$ block is a linker, and the $X_3$ block is a binding domain. The blocks may oriented from the N to the C-terminus as $(X_1)_a\text{-}(X_2)_b\text{-}(X_3)_c$ where a, b, and c are a number of repeats for that block. a, b, and c, may all be the same, all be different, or two of a, b, and c are the same and remaining one is different. The blocks may also be oriented from C-terminus to N-terminus as $(X_3)_c\text{-}(X_2)_b\text{-}(X_1)_a$. As an example for repeating blocks, each block may repeat any number of times and/or they may be ordered with multiple successive blocks such as $X_1\text{-}X_1\text{-}X_1\text{-}X_2\text{-}X_2\text{-}X_3$ where in this case a=3, b=2, and c=1. Examples of each block are provided herein. In various embodiments, a, b, and c are independently 1 to 50, including all values and ranges therebetween. A protein may comprise one or more additional blocks. The multivalent molecules are formed by the self-assembling ability of the coiled-coil domain ($X_1$ block) to form oligomers (e.g., trimers, tetramers, and pentamers). The MAPs may be referred to as "ACE-MAPs" or "H-MAPs."

The $X_1$ block is a coiled-coil-based domain. Additionally, the $X_1$ block may comprise a "kink" or "kinked region." Non-limiting examples of $X_1$ include CC-Type2-LL-L17Q octomer (PDB: 6G6F), CC-Type2-deLI hexamer (PDB: 6G6E), GCN4-pAA heptamer (PDB: 2HY6), CC-Type2-IL-Sg-L17E heptamer (PDB: 6G69), CC-Type2-LL-L-L17Q hexamer (PDB: 6G6B), CC-Type2-IL-Sg hexamer (PDB: 6G68), CC-Type2-deLI hexamer (PDB:6G6E), CC-Type2-IV hexamer (PDB: 6G66), COMPcc pentamer (PBD: 3v2p) and GCN4 trimer (PBD: 2O7H) or tetramer (PBD: 2IPZ), the sequences of which are incorporated herein by reference from PDB (www.resb.org) as of the date of filing. Examples of sequences for the $X_1$ block include, but are not limited to:

```
                                        (SEQ ID NO: 3)
MRGSHHHHHHGSACELAATATATATATATAACGDLAPQMLRELQETNAALQ

DVRELLRQQVKEITFLKNTLLEIWKAAK, (SEQ ID NO: 4)
MRGSHHHHHHGSASELAATATATATATATAASGDLAPQMLRELQETNAALQ

DVRELLRQQVKEITFLKNTLLEIWKAAK, (SEQ ID NO: 5)
MRGSHHHHHHGSACELAATATATATATATAACGDLAPQMLRELQETNAALQ

DVRELLRQQVKEITFLKNTLLEIWK, (SEQ ID NO: 6)
MRGSHHHHHHGSASELAATATATATATATAASGDLAPQMLRELQETNAALQ

DVRELLRQQVKEITFLKNTLLEIWK, (SEQ ID NO: 172)
MRGSHHHHHHGSACELAATATATATATATAACGDLAPQMLRELQETNAALQ

DVRELLRQQVKEITFLKNT, (SEQ ID NO: 173)
MRGSHHHHHHGSASELAATATATATATATAASGDLAPQMLRELQETNAALQ

DVRELLRQQVKEITFLKNT,
```

Other examples, may comprise portions of any of the foregoing sequences. The sequences may be used without the His tag or beginning linker domain, or with or without a nuclear localization sequence (NLS) tag such as PKKKRKV (SEQ ID NO:7). For example, the sequence of $X_1$ may comprise, consist essentially of, or consist of:

```
                                         (SEQ ID NO: 8)
GSACELAATATATATATATAACGDLAPQMLRELQETNAALQDVRELLRQQV
KEITFLKNTLLEIWKAAK, (SEQ ID NO: 9)
GSASELAATATATATATATAASGDLAPQMLRELQETNAALQDVRELLRQQV
KEITFLKNTLLEIWKAAK, (SEQ ID NO: 10)
GSACELAATATATATATATAACGDLAPQMLRELQETNAALQDVRELLRQQV
KEITFLKNTLLEIWK, (SEQ ID NO: 11)
GSASELAATATATATATATAASGDLAPQMLRELQETNAALQDVRELLRQQV
KEITFLKNTLLEIWK, (SEQ ID NO: 174)
MRGSHHHHHHGSACELAATATATATATATAACGDLAPQMLRELQETNAALQ
DVRELLRQQVKEITFLKNTLLEIWK, (SEQ ID NO: 175)
MRGSHHHHHHGSASELAATATATATATATAASGDLAPQMLRELQETNAALQ
DVRELLRQQVKEITFLKNTLLEIWK, (SEQ ID NO: 12)
DLAPQMLRELQETNAALQDVRELLRQQVKEITFLKNTLLEIWKAAK, (SEQ ID NO: 13)
DLAPQMLRELQETNAALQDVRELLRQQVKEITFLKNTLLEIWK, (SEQ ID NO: 14)
DLAPQMLRELQETNAALQDVRELLRQQVKEITFLKNT,
``` or (with full sequences below including His tag to show inclusion of NLS tag prior):

```
                                        (SEQ ID NO: 15)
MRGSPKKKRKVGGGGSHHHHHHHHGSACELAATATATATATATAACGDLAP
QMLRELQETNAALQDVRELLRQQVKEITFLKNTLLEIWKAAK, (SEQ ID NO: 16)
MRGSPKKKRKVGGGGSHHHHHHHHGSASELAATATATATATATAASGDLAP
QMLRELQETNAALQDVRELLRQQVKEITFLKNTLLEIWKAAK, (SEQ ID NO: 17)
MRGSPKKKRKVGGGGSHHHHHHHHGSACELAATATATATATATAACGDLAP
QMLRELQETNAALQDVRELLRQQVKEITFLKNTLLEIWK, (SEQ ID NO: 18)
MRGSPKKKRKVGGGGSHHHHHHHHGSASELAATATATATATATAASGDLAP
QMLRELQETNAALQDVRELLRQQVKEITFLKNTLLEIWK, (SEQ ID NO: 19)
MRGSPKKKRKVGGGGSHHHHHHHHDLAPQMLRELQETNAALQDVRELLRQQ
VKEITFLKNTLLEIWKAAK, (SEQ ID NO: 20)
MRGSPKKKRKVGGGGSHHHHHHHHDLAPQMLRELQETNAALQDVRELLRQQ
VKEITFLKNTLLEIWK, (SEQ ID NO: 21)
MRGSPKKKRKVGGGGSHHHHHHHHDLAPQMLRELQETNAALQDVRELLRQQ
VKEITFLKNT.
```

Other sequences provided herein as C sequences or ccCOMP sequences or variants thereof may also be used as $X_1$ block. The "kink" (included in some of the sequences above) may have the following sequence: LLEIWK (SEQ ID NO:36). The "kink" may connect the $X_1$ block to the $X_2$ block. The $X_1$ block may comprise, consist essentially of, or consist of any portion of any of the foregoing sequences.

$X_2$ block is a linking group, which may be referred to as a linker. Examples of linking groups include, but are not limited to: $(G_4S)_n$ (SEQ ID NO:22), $[EAAAK]_n$ (SEQ ID NO:176), $(EAAK)_n$ (SEQ ID NO:23), $(PAPAP)_n$ (SEQ ID NO:24), $A(EAAAK)_4ALEA(EAAAK)_4A$ (SEQ ID NO:25), AEAAAKEAAAKA (SEQ ID NO:26), $(Ala-Pro)_n$, VSQTSKLTRAETVFPDV (SEQ ID NO:27), PLGLWA (SEQ ID NO:28), RVLAEA (SEQ ID NO:29), EDVVCCSMSY (SEQ ID NO:30), GGIEGRGS (SEQ ID NO:31), TRHRQPRGWE (SEQ ID NO:32), AGNRVRRSVG (SEQ ID NO:33), RRRRRRRRR (SEQ ID NO:34), GFLG (SEQ ID NO:35), AAAKEAAAKEAAAK (SEQ ID NO:189), LE, $(G)_n$, or a disulfide bridge, where n is 1-50, including all integer values and ranges therebetween. Other examples of linkers include those provided in Table 1. In various examples, n is 1, 2, 3, 4, or 5. The $X_2$ block may comprise, consist essentially of, or consist of any portion of any of the foregoing sequences.

$X_3$ block is the binding domain. The binding domain binds to a target protein. The target protein is a protein to which binding is desired or intended, for example, in situations where reduction in the severity of infection caused by a microorganism exhibiting the target protein is desired. For example, the binding domain binds to coronaviruses having a spike protein. Non-limiting examples of binding domains include ACEBinder 1: (IEEQAKTFLDKFNHEAE-DLFYQS) (SEQ ID NO:37), ACEBinder 2 (LEEQYKT-FLDKFMHELEDLLYQL) (SEQ ID NO:38), and HIF1α-binder 1 (IEEQAKTFLDKFNGEELLRALDQVN) (SEQ ID NO:39). In various embodiments, HiF1α$_{BINDER}$ has the following sequence: LEEQAKTFLDKFNGEELL-RALQDQVN (SEQ ID NO:190) A non-limiting list of binding domains that display one or more alpha helical structures in the binding interface, including HIF1α-binder 1, can be found at the HippDB database at www.nvu.edu/projects/arora/hippdb, the sequences described therein are incorporated herein by reference as of the date of filing. Additional examples may include: HUMAN GLUTA-THIONE S-TRANSFERASE P1-1, COMPLEX WITH TER117, chains A or B (pdb: 1OGS) or ANTAGONIST HIV-1 GAG PEPTIDES WITH HLA B8-HIV-1 GAG PEP-TIDE—HUMAN IMMUNODEFICIENCY VIRUS 1 chains A, B, or C (pdb: 1AGB), the sequences of which are incorporated herein by reference from PDB (www.resb.org) as of the date of filing. The $X_3$ block may comprise, consist essentially of, or consist of any portion of any of the foregoing sequences.

Provided are various MAPs. The MAPs may include the sequences the sequence GSACELAATATATATATATAACG (SEQ ID NO:102) or GSASELAATATATATATATAASG (SEQ ID NO:103). Non-limiting examples of MAPs comprise, consist essentially of, or consist of the following:

| Linker | | Sequence | SEQ ID NO |
|---|---|---|---|
| ACE-MAP-1 | | | |
| NA | With Cys | MRGSHHHHHHGSACELAATATATATATATATAACGDL APQMLRELQETNAALQDVRELLRQQVKEITFLKNTL LEIWKAAAKEAAAKEAAAKIEEQAKTFLDKFNHEAE DLFYQS | 40 |
| | Without Cys | MRGSHHHHHHGSASELAATATATATATATATAASGDL APQMLRELQETNAALQDVRELLRQQVKEITFLKNTL LEIWKAAAKEAAAKEAAAKIEEQAKTFLDKFNHEAE DLFYQS | 41 |
| Rigid (EAAK)$_n$ (SEQ ID NO: 25) linker | With Cys | MRGSHHHHHHGSACELAATATATATATATATAACGDL APQMLRELQETNAALQDVRELLRQQVKEITFLKNTL LEIWKAAAK(EAAK)$_n$IEEQAKTFLDKFNHEAEDLFY QS | 42 |
| | Without Cys | MRGSHHHHHHGSASELAATATATATATATATAASGDL APQMLRELQETNAALQDVRELLRQQVKEITFLKNTL LEIWKAAAK(EAAK)$_n$IEEQAKTFLDKFNHEAEDLFY QS | 43 |
| Rigid (PAPAP)$_n$ (SEQ ID NO: 26) linker | With Cys | MRGSHHHHHHGSACELAATATATATATATATAACGDL APQMLRELQETNAALQDVRELLRQQVKEITFLKNTL LEIWKAAAK(PAPAP)$_n$IEEQAKTFLDKFNHEAEDLFY QS | 44 |
| | Without Cys | MRGSHHHHHHGSASELAATATATATATATATAASGDL APQMLRELQETNAALQDVRELLRQQVKEITFLKNTL LEIWKAAAK(PAPAP)$_n$IEEQAKTFLDKFNHEAEDLFY QS | 45 |
| Flexible linker (G$_4$S)$_n$ (SEQ ID NO: 24) | With Cys | MRGSHHHHHHGSACELAATATATATATATATAACGDL APQMLRELQETNAALQDVRELLRQQVKEITFLKNTL LEIWKAAAK(GGGGS)$_n$IEEQAKTFLDKFNHEAEDLFY QS | 46 |
| | Without Cys | MRGSHHHHHHGSASELAATATATATATATATAASGDL APQMLRELQETNAALQDVRELLRQQVKEITFLKNTL LEIWKAAAK(GGGGS)$_n$IEEQAKTFLDKFNHEAEDLFY QS | 47 |
| Flexible linker (AT)$_n$ | With Cys | MRGSHHHHHHGSACELAATATATATATATATAACGDL APQMLRELQETNAALQDVRELLRQQVKEITFLKNTL LEIWKAAAK(AT)$_n$IEEQAKTFLDKFNHEAEDLFYQS | 48 |
| | Without Cys | MRGSHHHHHHGSASELAATATATATATATATAASGDL APQMLRELQETNAALQDVRELLRQQVKEITFLKNTL LEIWKAAAK(AT)$_n$IEEQAKTFLDKFNHEAEDLFYQS | 49 |
| ACE-MAP-2 | | | |
| NA | With Cys | MRGSHHHHHHGSACELAATATATATATATATAACGD LAPQMLRELQETNAALQDVRELLRQQVKEITFLKN TLLEIWKAAKEAAKEAAAKLEEQYKTFLDKFMHE LEDLLYQL | 50 |
| | Without Cys | MRGSHHHHHHGSASELAATATATATATATATAASGD LAPQMLRELQETNAALQDVRELLRQQVKEITFLKN TLLEIWKAAKEAAKEAAAKLEEQYKTFLDKFMHE LEDLLYQL | 51 |
| Rigid (EAAAK)$_n$ (SEQ ID NO: 25)/ (EAAK)$_n$ (SEQ ID NO: 176) linker | With Cys | MRGSHHHHHHGSACELAATATATATATATATAACGD LAPQMLRELQETNAALQDVRELLRQQVKEITFLKN TLLEIWKAAK(EAAAK)$_n$LEEQYKTFLDKFMHELED LLYQL | 52 |
| | | MRGSHHHHHHGSACELAATATATATATATATAACGD LAPQMLRELQETNAALQDVRELLRQQVKEITFLKN TLLEIWKAAK(EAAK)$_n$LEEQYKTFLDKFMHELEDL LYQL | 177 |
| | Without Cys | MRGSHHHHHHGSASELAATATATATATATATAASGD LAPQMLRELQETNAALQDVRELLRQQVKEITFLKN TLLEIWKAAK(EAAAK)$_n$LEEQYKTFLDKFMHELED LLYQL | 53 |
| | | MRGSHHHHHHGSASELAATATATATATATATAASGD LAPQMLRELQETNAALQDVRELLRQQVKEITFLKN TLLEIWKAAK(EAAK)$_n$LEEQYKTFLDKFMHELEDL LYQL | 178 |
| Rigid (PAPAP)$_n$ (SEQ ID NO: 26) | With Cys | MRGSHHHHHHGSACELAATATATATATATATAACGD LAPQMLRELQETNAALQDVRELLRQQVKEITFLKN TLLEIWKAAK(PAPAP)$_n$LEEQYKTFLDKFMHELEDL LYQL | 54 |

| Linker | | Sequence | SEQ ID NO |
|---|---|---|---|
| linker | Without Cys | MRGSHHHHHHGSASELAATATATATATATATAASGD LAPQMLRELQETNAALQDVRELLRQQVKEITFLKN TLLEIWKAAK(PAPAP)$_n$LEEQYKTFLDKFMHELEDL LYQL | 55 |
| Flexible linker (G$_4$S)$_n$ (SEQ ID NO: 24) | With Cys | MRGSHHHHHHGSACELAATATATATATATATAACGD LAPQMLRELQETNAALQDVRELLRQQVKEITFLKN TLLEIWKAAK(GGGGS)$_n$LEEQYKTFLDKFMHELED LLYQL | 56 |
| | Without Cys | MRGSHHHHHHGSASELAATATATATATATATAASGD LAPQMLRELQETNAALQDVRELLRQQVKEITFLKN TLLEIWKAAK(GGGGS)$_n$LEEQYKTFLDKFMHELED LLYQL | 57 |
| Flexible linker (AT)$_n$ | With Cys | MRGSHHHHHHGSACELAATATATATATATATAACGD LAPQMLRELQETNAALQDVRELLRQQVKEITFLKN TLLEIWKAAK(AT)$_n$LEEQYKTFLDKFMHELEDLLY QL | 58 |
| | Without Cys | MRGSHHHHHHGSASELAATATATATATATATAASGD LAPQMLRELQETNAALQDVRELLRQQVKEITFLKN TLLEIWKAAK(AT)$_n$LEEQYKTFLDKFMHELEDLLY QL | 59 |
| HIF1α-MAP | | | |
| NA | With Cys | MRGSHHHHHHGSACELAATATATATATATATAACGD LAPQMLRELQETNAALQDVRELLRQQVKEITFLKNT LLEIWKAAKEAAKEAAAKIEEQAKTFLDKFNGEELL RALDQVN | 60 |
| | Without Cys | MRGSHHHHHHGSASELAATATATATATATATAASGDL APQMLRELQETNAALQDVRELLRQQVKEITFLKNTL LEIWKAAKEAAKEAAAKIEEQAKTFLDKFNGEELLR ALDQVN | 61 |
| Rigid (EAAK)$_n$ (SEQ ID NO: 25)/ (EAAAK)$_n$ (SEQ ID NO: 176) linker | With Cys | MRGSHHHHHHGSACELAATATATATATATATAACGD LAPQMLRELQETNAALQDVRELLRQQVKEITFLKNT LLEIWKAAK(EAAK)$_n$IEEQAKTFLDKFNGEELLRA LDQVN | 64 |
| | | MRGSHHHHHHGSACELAATATATATATATATAACGD LAPQMLRELQETNAALQDVRELLRQQVKEITFLKNT LLEIWKAAK(EAAK)$_n$IEEQAKTFLDKFNGEELLRAL DQVN | 179 |
| | Without Cys | MRGSHHHHHHGSASELAATATATATATATATAASGDL APQMLRELQETNAALQDVRELLRQQVKEITFLKNTL LEIWKAAK(EAAAK)$_n$IEEQAKTFLDKFNGEELLRAL DQVN | 65 |
| | | MRGSHHHHHHGSASELAATATATATATATATAASGDL APQMLRELQETNAALQDVRELLRQQVKEITFLKNTL LEIWKAAK(EAAK)$_n$IEEQAKTFLDKFNGEELLRALD QVN | 180 |
| Rigid (PAPAP)$_n$ (SEQ ID NO: 26) linker | With Cys | MRGSHHHHHHGSACELAATATATATATATATAACGD LAPQMLRELQETNAALQDVRELLRQQVKEITFLKNT LLEIWKAAK(PAPAP)$_n$IEEQAKTFLDKFNGEELLRAL DQVN | 66 |
| | Without Cys | MRGSHHHHHHGSASELAATATATATATATATAASGDL APQMLRELQETNAALQDVRELLRQQVKEITFLKNTL LEIWKAAK(PAPAP)$_n$IEEQAKTFLDKFNGEELLRALD QVN | 67 |
| Flexible linker (G$_4$S)$_n$ (SEQ ID NO: 24) | With Cys | MRGSHHHHHHGSACELAATATATATATATATAACGD LAPQMLRELQETNAALQDVRELLRQQVKEITFLKNT LLEIWKAAK(GGGGS)$_n$IEEQAKTFLDKFNGEELLRAL DQVN | 68 |
| | Without Cys | MRGSHHHHHHGSASELAATATATATATATATAASGDL APQMLRELQETNAALQDVRELLRQQVKEITFLKNTL LEIWKAAK(GGGGS)$_n$IEEQAKTFLDKFNGEELLRAL DQVN | 69 |
| Flexible linker (AT)$_n$ | With Cys | MRGSHHHHHHGSACELAATATATATATATATAACGD LAPQMLRELQETNAALQDVRELLRQQVKEITFLKNT LLEIWKAAK(AT)$_n$IEEQAKTFLDKFNGEELLRALDQ VN | 70 |

| Linker | | Sequence | SEQ ID NO |
|---|---|---|---|
| | Without Cys | MRGSHHHHHHGSASELAATATATATATATAASGDL APQMLRELQETNAALQDVRELLRQQVKEITFLKNTL LEIWKAAK(AT)ₙIEEQAKTFLDKFNGEELLRALDQV N | 71 |

HIF1α-MAP-2 (H-MAP2)

| Linker | | Sequence | SEQ ID NO |
|---|---|---|---|
| NA | With Cys | MRGSPKKKRKVGGGGSHHHHHHHGSACELAATA TATATATATAACGDLAPQMLRELQETNAALQDVRE LLRQQVKEITFLKNTLLEIWKAAKEAAKEAAAKIEE QAKTFLDKFNGEELLRALDQVN | 62 |
| | Without Cys | MRGSPKKKRKVGGGGSHHHHHHHGSASELAATA TATATATATAASGDLAPQMLRELQETNAALQDVRE LLRQQVKEITFLKNTLLEIWKAAKEAAKEAAAKIEE QAKTFLDKFNGEELLRALDQVN | 63 |
| Rigid (EAAAK)ₙ (SEQ ID NO: 25)/ (EAAK)ₙ (SEQ ID NO: 176) linker | With Cys | MRGSPKKKRKVGGGGSHHHHHHHGSACELAATA TATATATATAACGDLAPQMLRELQETNAALQDVRE LLRQQVKEITFLKNTLLEIWKAAK(EAAAK)ₙIEEQAK TFLDKFNGEELLRALDQVN | 163 |
| | | MRGSPKKKRKVGGGGSHHHHHHHGSACELAATA TATATATATAACGDLAPQMLRELQETNAALQDVRE LLRQQVKEITFLKNTLLEIWKAAK(EAAK)ₙIEEQAKT FLDKFNGEELLRALDQVN | 181 |
| | Without Cys | MRGSPKKKRKVGGGGSHHHHHHHGSASELAATA TATATATATAASGDLAPQMLRELQETNAALQDVRE LLRQQVKEITFLKNTLLEIWKAAK(EAAAK)ₙIEEQAK TFLDKFNGEELLRALDQVN | 164 |
| | | MRGSPKKKRKVGGGGSHHHHHHHGSASELAATA TATATATATAASGDLAPQMLRELQETNAALQDVRE LLRQQVKEITFLKNTLLEIWKAAK(EAAK)ₙIEEQAKT FLDKFNGEELLRALDQVN | 182 |
| Rigid (PAPAP)ₙ (SEQ ID NO: 26) linker | With Cys | MRGSPKKKRKVGGGGSHHHHHHHGSACELAATA TATATATATAACGDLAPQMLRELQETNAALQDVRE LLRQQVKEITFLKNTLLEIWKAAK(PAPAP)ₙIEEQAK TFLDKFNGEELLRALDQVN | 165 |
| | Without Cys | MRGSPKKKRKVGGGGSHHHHHHHGSASELAATA TATATATATAASGDLAPQMLRELQETNAALQDVRE LLRQQVKEITFLKNTLLEIWKAAK(PAPAP)ₙIEEQAK TFLDKFNGEELLRALDQVN | 166 |
| Flexible linker (G₄S)ₙ (SEQ ID NO: 24) | With Cys | MRGSPKKKRKVGGGGSHHHHHHHGSACELAATA TATATATATAACGDLAPQMLRELQETNAALQDVRE LLRQQVKEITFLKNTLLEIWKAAK(GGGGS)ₙIEEQAK TFLDKFNGEELLRALDQVN | 167 |
| | Without Cys | MRGSPKKKRKVGGGGSHHHHHHHGSASELAATA TATATATATAASGDLAPQMLRELQETNAALQDVRE LLRQQVKEITFLKNTLLEIWKAAK(GGGGS)ₙIEEQAK TFLDKFNGEELLRALDQVN | 168 |
| Flexible linker (AT)ₙ | With Cys | MRGSPKKKRKVGGGGSHHHHHHHGSACELAATA TATATATATAACGDLAPQMLRELQETNAALQDVRE LLRQQVKEITFLKNTLLEIWKAAK(AT)ₙIEEQAKTFL DKFNGEELLRALDQVN | 169 |
| | Without Cys | MRGSPKKKRKVGGGGSHHHHHHHGSASELAATA TATATATATAASGDLAPQMLRELQETNAALQDVRE LLRQQVKEITFLKNTLLEIWKAAK(AT)ₙIEEQAKTFL DKFNGEELLRALDQVN | 170 |

ACE-MAP-1 without cloning and/or His tag

| Linker | | Sequence | SEQ ID NO |
|---|---|---|---|
| NA | With Cys | GSACELAATATATATATATATAACGDLAPQMLRELQ ETNAALQDVRELLRQQVKEITFLKNTLLEIWKAAA KEAAAKEAAAKIEEQAKTFLDKFNHEAEDLFYQS | 72 |
| | Without Cys | GSASELAATATATATATATATAASGDLAPQMLRELQ ETNAALQDVRELLRQQVKEITFLKNTLLEIWKAAA KEAAAKEAAAKIEEQAKTFLDKFNHEAEDLFYQS | 73 |
| | Truncated | DLAPQMLRELQETNAALQDVRELLRQQVKEITFL KNTLLEIWKAAAKEAAAKEAAAKIEEQAKTFLDK FNHEAEDLFYQS | 104 |
| Rigid (EAAAK)ₙ (SEQ ID | With Cys | GSACELAATATATATATATATAACGDLAPQMLRELQ ETNAALQDVRELLRQQVKEITFLKNTLLEIWKAAA K(EAAAK)ₙIEEQAKTFLDKFNHEAEDLFYQS | 74 |

| Linker | | Sequence | SEQ ID NO |
|---|---|---|---|
| NO: 176) linker | Without Cys | GSASELAATATATATATATATAASGDLAPQMLRELQ ETNAALQDVRELLRQQVKEITFLKNTLLEIWKAAA K(EAAAK)ₙIEEQAKTFLDKFNHEAEDLFYQS | 75 |
| | Truncated | DLAPQMLRELQETNAALQDVRELLRQQVKEITFL KNTLLEIWKAAAK(EAAAK)ₙIEEQAKTFLDKFNHE AEDLFYQS | 105 |
| Rigid (PAPAP)ₙ (SEQ ID NO: 26) linker | With Cys | GSACELAATATATATATATATAACGDLAPQMLRELQ ETNAALQDVRELLRQQVKEITFLKNTLLEIWKAAA K(PAPAP)ₙIEEQAKTFLDKFNHEAEDLFYQS | 76 |
| | Without Cys | GSASELAATATATATATATATAASGDLAPQMLRELQ ETNAALQDVRELLRQQVKEITFLKNTLLEIWKAAA K(PAPAP)ₙIEEQAKTFLDKFNHEAEDLFYQS | 77 |
| | Truncated | DLAPQMLRELQETNAALQDVRELLRQQVKEITFL KNTLLEIWKAAAK(PAPAP)ₙIEEQAKTFLDKFNHE AEDLFYQS | 106 |
| Flexible linker (G₄S)ₙ (SEQ ID NO: 24) | With Cys | GSACELAATATATATATATATAACGDLAPQMLRELQ ETNAALQDVRELLRQQVKEITFLKNTLLEIWKAAA K(GGGGS)ₙIEEQAKTFLDKFNHEAEDLFYQS | 78 |
| | Without Cys | GSASELAATATATATATATATAASGDLAPQMLRELQ ETNAALQDVRELLRQQVKEITFLKNTLLEIWKAAA K(GGGGS)ₙIEEQAKTFLDKFNHEAEDLFYQS | 79 |
| | Truncated | DLAPQMLRELQETNAALQDVRELLRQQVKEITFL KNTLLEIWKAAAK(GGGGS)ₙIEEQAKTFLDKFNHE AEDLFYQS | 107 |
| Flexible linker (AT)ₙ | With Cys | GSACELAATATATATATATATAACGDLAPQMLRELQ ETNAALQDVRELLRQQVKEITFLKNTLLEIWKAAA K(AT)ₙIEEQAKTFLDKFNHEAEDLFYQS | 80 |
| | Without Cys | GSASELAATATATATATATATAASGDLAPQMLRELQ ETNAALQDVRELLRQQVKEITFLKNTLLEIWKAAA K(AT)ₙIEEQAKTFLDKFNHEAEDLFYQS | 81 |
| | Truncated | DLAPQMLRELQETNAALQDVRELLRQQVKEITFL KNTLLEIWKAAAK(AT)ₙIEEQAKTFLDKFNHEAED LFYQS | 108 |
| ACE-MAP-2 without cloning and/or His tag | | | |
| NA | With Cys | GSACELAATATATATATATATAACGDLAPQMLRE LQETNAALQDVRELLRQQVKEITFLKNTLLEIW KAAKEAAKEAAAKLEEQYKTFLDKFMHELEDL LYQL | 82 |
| | Without Cys | GSASELAATATATATATATATAASGDLAPQMLREL QETNAALQDVRELLRQQVKEITFLKNTLLEIWK AAKEAAKEAAAKLEEQYKTFLDKFMHELEDLL YQL | 83 |
| | Truncated | DLAPQMLRELQETNAALQDVRELLRQQVKEITF LKNTLLEIWKAAKEAAKEAAAKLEEQYKTFLD KFMHELEDLLYQL | 109 |
| Rigid (EAAK)ₙ (SEQ ID NO: 25)/ (EAAAK)ₙ (SEQ ID NO: 176) linker | With Cys | GSACELAATATATATATATATAACGDLAPQMLRE LQETNAALQDVRELLRQQVKEITFLKNTLLEIW KAAK(EAAAK)ₙLEEQYKTFLDKFMHELEDLLY QL | 84 |
| | | GSACELAATATATATATATATAACGDLAPQMLRE LQETNAALQDVRELLRQQVKEITFLKNTLLEIW KAAK(EAAK)ₙLEEQYKTFLDKFMHELEDLLYQL | 183 |
| | Without Cys | GSASELAATATATATATATATAASGDLAPQMLREL QETNAALQDVRELLRQQVKEITFLKNTLLEIWK AAK(EAAAK)ₙLEEQYKTFLDKFMHELEDLLYQL | 85 |
| | | GSASELAATATATATATATATAASGDLAPQMLREL QETNAALQDVRELLRQQVKEITFLKNTLLEIWK AAK(EAAK)ₙLEEQYKTFLDKFMHELEDLLYQL | 184 |
| | Truncated | DLAPQMLRELQETNAALQDVRELLRQQVKEITF LKNTLLEIWKAAK(EAAAK)ₙLEEQYKTFLDKFM HELEDLLYQL | 110 |
| | | DLAPQMLRELQETNAALQDVRELLRQQVKEITF LKNTLLEIWKAAK(EAAK)ₙLEEQYKTFLDKFMH ELEDLLYQL | 185 |
| Rigid (PAPAP)ₙ (SEQ ID NO: 26) | With Cys | GSACELAATATATATATATATAACGDLAPQMLRE LQETNAALQDVRELLRQQVKEITFLKNTLLEIW KAAK(PAPAP)ₙLEEQYKTFLDKFMHELEDLLYQ L | 86 |

-continued

| Linker | | Sequence | SEQ ID NO |
|---|---|---|---|
| linker | Without Cys | GSASELAATATATATATATATAASGDLAPQMLREL QETNAALQDVRELLRQQVKEITFLKNTLLEIW KAAK(PAPAP)$_n$LEEQYKTFLDKFMHELEDLLYQL | 87 |
| | Truncated | DLAPQMLRELQETNAALQDVRELLRQQVKEITF LKNTLLEIWKAAK(PAPAP)$_n$LEEQYKTFLDKFM HELEDLLYQL | 111 |
| Flexible linker (G$_4$S)$_n$ (SEQ ID NO: 24) | With Cys | GSACELAATATATATATATATAACGDLAPQMLRE LQETNAALQDVRELLRQQVKEITFLKNTLLEIW KAAK(GGGGS)$_n$LEEQYKTFLDKFMHELEDLLYQ L | 88 |
| | Without Cys | GSASELAATATATATATATATAASGDLAPQMLREL QETNAALQDVRELLRQQVKEITFLKNTLLEIWK AAK(GGGGS)$_n$LEEQYKTFLDKFMHELEDLLYQL | 89 |
| | Truncated | DLAPQMLRELQETNAALQDVRELLRQQVKEITF LKNTLLEIWKAAK(GGGGS)$_n$LEEQYKTFLDKFM HELEDLLYQL | 112 |
| Flexible linker (AT)$_n$ | With Cys | GSACELAATATATATATATATAACGDLAPQMLRE LQETNAALQDVRELLRQQVKEITFLKNTLLEIW KAAK(AT)$_n$LEEQYKTFLDKFMHELEDLLYQL | 90 |
| | Without Cys | GSASELAATATATATATATATAASGDLAPQMLREL QETNAALQDVRELLRQQVKEITFLKNTLLEIWK AAK(AT)$_n$LEEQYKTFLDKFMHELEDLLYQL | 91 |
| | Truncated | DLAPQMLRELQETNAALQDVRELLRQQVKEITF LKNTLLEIWKAAK(AT)$_n$LEEQYKTFLDKFMHEL EDLLYQL | 113 |
| HIF1α-MAP without cloning and/or His tag | | | |
| NA | With Cys | GSACELAATATATATATATATAACGDLAPQMLRELQ ETNAALQDVRELLRQQVKEITFLKNTLLEIWKAAK EAAKEAAAKIEEQAKTFLDKFNGEELLRALDQVN | 92 |
| | Without Cys | GSASELAATATATATATATATAASGDLAPQMLRELQ ETNAALQDVRELLRQQVKEITFLKNTLLEIWKAAK EAAKEAAAKIEEQAKTFLDKFNGEELLRALDQVN | 93 |
| | Truncated | DLAPQMLRELQETNAALQDVRELLRQQVKEITFL KNTLLEIWKAAKEAAKEAAAKIEEQAKTFLDKFN GEELLRALDQVN | 114 |
| Rigid (EAAK)$_n$ (SEQ ID NO: 25)/ (EAAAK)$_n$ (SEQ ID NO: 176) linker | With Cys | GSACELAATATATATATATATAACGDLAPQMLRELQ ETNAALQDVRELLRQQVKEITFLKNTLLEIWKAAK (EAAAK)$_n$IEEQAKTFLDKFNGEELLRALDQVN | 94 |
| | | GSACELAATATATATATATATAACGDLAPQMLRELQ ETNAALQDVRELLRQQVKEITFLKNTLLEIWKAAK (EAAK)$_n$IEEQAKTFLDKFNGEELLRALDQVN | 186 |
| | Without Cys | GSASELAATATATATATATATAASGDLAPQMLRELQ ETNAALQDVRELLRQQVKEITFLKNTLLEIWKAAK (EAAAK)$_n$IEEQAKTFLDKFNGEELLRALDQVN | 95 |
| | | GSASELAATATATATATATATAASGDLAPQMLRELQ ETNAALQDVRELLRQQVKEITFLKNTLLEIWKAAK (EAAK)$_n$IEEQAKTFLDKFNGEELLRALDQVN | 187 |
| | Truncated | DLAPQMLRELQETNAALQDVRELLRQQVKEITFL KNTLLEIWKAAK(EAAAK)$_n$IEEQAKTFLDKFNGEE LLRALDQVN | 115 |
| | | DLAPQMLRELQETNAALQDVRELLRQQVKEITFL KNTLLEIWKAAK(EAAK)$_n$IEEQAKTFLDKFNGEEL LRALDQVN | 188 |
| Rigid (PAPAP)$_n$ (SEQ ID NO: 26) linker | With Cys | GSACELAATATATATATATATAACGDLAPQMLRELQ ETNAALQDVRELLRQQVKEITFLKNTLLEIWKAAK (PAPAP)$_n$IEEQAKTFLDKFNGEELLRALDQVN | 96 |
| | Without Cys | GSASELAATATATATATATATAASGDLAPQMLRELQ ETNAALQDVRELLRQQVKEITFLKNTLLEIWKAAK (PAPAP)$_n$IEEQAKTFLDKFNGEELLRALDQVN | 97 |
| | Truncated | DLAPQMLRELQETNAALQDVRELLRQQVKEITFL KNTLLEIWKAAK(PAPAP)$_n$IEEQAKTFLDKFNGEEL LRALDQVN | 116 |
| Flexible linker (G$_4$S)$_n$ (SEQ ID NO: 24) | With Cys | GSACELAATATATATATATATAACGDLAPQMLRELQ ETNAALQDVRELLRQQVKEITFLKNTLLEIWKAAK (GGGGS)$_n$IEEQAKTFLDKFNGEELLRALDQVN | 98 |
| | Without Cys | GSASELAATATATATATATATAASGDLAPQMLRELQ ETNAALQDVRELLRQQVKEITFLKNTLLEIWKAAK (GGGGS)$_n$IEEQAKTFLDKFNGEELLRALDQVN | 99 |

| Linker | | Sequence | SEQ ID NO |
|---|---|---|---|
| | Truncated | DLAPQMLRELQETNAALQDVRELLRQQVKEITFL KNTLLEIWKAAK(GGGGS)$_n$IEEQAKTFLDKFNGEE LLRALDQVN | 117 |
| Flexible linker (AT)$_n$ | With Cys | GSACELAATATATATATATAACGDLAPQMLRELQ ETNAALQDVRELLRQQVKEITFLKNTLLEIWKAAK (AT)$_n$IEEQAKTFLDKFNGEELLRALDQVN | 100 |
| | Without Cys | GSASELAATATATATATATAASGDLAPQMLRELQ ETNAALQDVRELLRQQVKEITFLKNTLLEIWKAAK (AT)$_n$IEEQAKTFLDKFNGEELLRALDQVN | 101 |
| | Truncated | DLAPQMLRELQETNAALQDVRELLRQQVKEITFL KNTLLEIWKAAK(AT)$_n$IEEQAKTFLDKFNGEELLR ALDQVN | 118 |

The proteins may be expressed in a different vector that does not necessarily bear the N-terminal histidine tag or its linker to the $X_1$ block. Depending upon whether the sequence bears a N-terminal histidine tag and which vector is used for cloning, the N-terminal sequence of the polymer carrier can vary. Thus, in various examples, the MR-GSHHHHHH (SEQ ID NO:119) or MRGSHHHHHHGSASELAATATATATATATAASG (SEQ ID NO: 120) or MRGSHHHHHHGSASELAATATATATATATAA-CG (SEQ ID NO:121) or any portion of SEQ ID NOs:119-121 is optional in any of the aforementioned sequences. Further, any residual amino acids from expression and sequencing may also be deleted.

In various examples, a protein of the present disclosure has 75%, 80%, 85%, 90%, 91%, 92%, 93%, 94%, 95%, 96%, 97%, 98%, or 99% homology with any of the sequences described herein (including sequences with and without a His tag and/or sequence portions from a cloning vector) or may comprise, consist essentially of, or consist of any portion of any one of the sequences of the present disclosure. Proteins of the present disclosure may be longer than the sequences described herein and comprise the sequences described herein. The proteins may further comprise additional amino acids, which may naturally occurring amino acids, or may be a mixture of naturally occurring and non-naturally occurring amino acids.

The molecular weight of the proteins of the present disclosure can vary depending upon the number of blocks and the number of amino acids in the blocks. For example, the molecular weight can be from about 10,000 Da to about 150,000 Da as a self-assembled protein or 6,000 to 20,000 Da as a monomeric unit. For example, the molecular weight of the self-assembled protein can be about 62 kDa.

For expression of the proteins, the nucleic acid sequences encoding the carrier protein may be inserted into a recombinant vector, which may be plasmids, viruses or any other vehicle known in the art that has been manipulated by the insertion or incorporation of the nucleic acid sequences encoding the chimeric peptides of the invention. The recombinant vector typically contains an origin of replication, a promoter, as well as specific genes that allow phenotypic selection of the transformed cells. Vectors suitable for use in the present disclosure include, but are not limited to, the T7-based expression vector for expression in bacteria or viral vectors for expression in mammalian cells, baculovirus-derived vectors for expression in insect cells, and cauliflower mosaic virus (CaMV), tobacco mosaic virus (TMV), and other vectors.

The proteins of the present disclosure may be prepared via solid phase peptide synthesis (SPPS) using fluorenyl-methoxycarbonyl-based (Fmoc-based) chemistries or tert-butyloxycarbonyl (Boc) chemistries. The proteins may be prepared by a combination of SPPS and ligation techniques (e.g., native chemical ligation, Staudinger ligation, and the like).

The proteins of the present disclosure may be prepared via purification using a $Co^{2+}$ charged affinity chromatography column under denaturing conditions (i.e. 6 M urea in purification buffer) followed by a stepwise dialysis consisting first of a 3 M urea (or other denaturing agent) 5 L buffer bucket, followed by a 1.5 M urea, and 0.75 M Urea (in buffer). The dialysis may then be continued for six buckets in buffer. Following the protein may then be separated from remaining impurities using a size exclusion chromatography column in the monomeric or other oligomerization states.

Depending on the vector utilized, any of a number of suitable transcription and translation elements, including constitutive and inducible promoters, transcription enhancer elements, transcription terminators, etcetera, may be used in the expression vector. Such construction of expression vectors and the expression of genes in transfected cells can involve the use of molecular cloning techniques (for example, in vitro recombinant DNA techniques, synthetic techniques, and in vivo recombination/genetic recombination), bacterial systems for the expression of vectors, yeast systems with constitutive or inducible promoters, insect systems, prokaryotic and eukaryotic systems using transfection or co-transfections of DNA vectors, transgenic animals using for example viral infection, and embryonic stem cells. Methods and procedures for using and applying such vectors are widespread in publications and are known or easily obtainable by persons of ordinary skill in the art.

In one aspect, the present disclosure provides compositions suitable for delivering MAPs (e.g., ACE-MAPs and/or H-MAPs) to individuals. The compositions comprise the MAPs (e.g., ACE-MAPs and/or H-MAPs) disclosed herein in suitable carriers. Suitable carriers for use in such compositions are known in the art. Examples of suitable carriers for administration include water, saline solution, buffer solutions such as phosphate buffers, glycine solutions. Suitable carriers for in vitro use include all of the above and standard culturing media (e.g., DMEM and the like), with or without serum, such as fetal bovine serum or serum-free define media.

In one embodiment, suitable carriers include a diluent, adjuvant, excipient, or other vehicle with which the present complexes may be administered to an individual. The formulations may be in an injectable form (for administration via any of the standard injectable routes) to an individual. The individual may be a human being or a non-human animal. Some examples of materials which can serve as pharmaceutically-acceptable carriers include: sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The composition, if desired, can also contain minor amounts of wetting or emulsifying agents, or pH buffering agents. Some examples of compositions suitable for mixing with the agent can be found in: *Remington: The Science and Practice of Pharmacy* (2012) 22nd Edition, Philadelphia, PA Lippincott Williams & Wilkins. In one embodiment, the agent is substantially purified (e.g., substantially free from substances that limit its effect or produce undesired side-effects).

In an embodiment, the compositions may be formulated for topical, transdermal, or mucosal use. Such formulations include powders, sprays, ointments, pastes, creams, lotions, gels, solutions, patches and inhalants. The components may be mixed under sterile conditions with a pharmaceutically-acceptable carrier, and with any preservatives, buffers, or propellants which may be required. The ointments, pastes, creams and gels may contain additional excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Topical powders and sprays can also contain additional excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. In one embodiment, a 3D collagen based matrix may be used. In one embodiment, transdermal patches may be used. These have the added advantage of providing controlled delivery to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel. In one embodiment, the compositions are applied to dermal patches, bandages, gauges or other similar materials that can be directly applied to a desired area.

In one aspect, this disclosure provides a method of treating a SARS-CoV-2 infection or a severe (e.g., requiring hospitalization or virus-targeted medication) SARS-CoV-2 infection, also referred to herein as COVID-19 infection in a subject comprising administering to the subject an effective amount of a composition comprising one or more ACE-MAP proteins described herein. The composition may be administered once or multiple times, over a period of days, weeks or months. For example, the multiple doses of the composition may be administered with a suitable period in-between, such as days, weeks or months, and/or may be administered on an annual or any other periodic manner. The compositions may be delivered by any suitable route of administration, including oral, intraperitoneal, intramuscular and the like. Suitable dosages of the compositions may be administered to subjects who have contracted the SARS-COV-2 virus. The subjects may be symptomatic or asymptomatic. The therapeutic dosages may be combined with other therapies, including antibody therapy, steroids, anti-viral, anti-inflammatory and any other therapy.

In one aspect, this disclosure provides a method of preventing or reducing the severity of a SARS-CoV-2 infection in a subject comprising administering to the subject an effective amount of a composition comprising one or more ACE-MAP proteins described herein. The composition may be administered once or multiple times, typically over a period of days. The compositions may be delivered by any suitable route of administration, including oral, intraperitoneal, intramuscular and the like. Suitable dosages of the compositions may be administered to subjects who are considered to be at risk of contracting the SARS-COV-2 virus. Such subjects may include those who have come in contact with an infected individual (someone who has tested positive for COVID-19), or who are otherwise considered to be at a higher risk (e.g., immunocompromised individuals). For prophylactic use, the compositions may be administered to subjects who are symptomatic but testing as COVID negative, or who may be asymptomatic and COVID-testing negative. The prophylactic dosages may be combined with other prophylactic applications, such as vaccines and the like.

The present compositions can be effectively used for the prevention, treatment, reducing the severity of, or detection of different strains of SARS-COV-2. For example, the present proteins were found to be effective for the delta variant of the SARS-COV-2. In various examples, the present proteins and compositions may be used for prevention, treatment, reducing the severity of, or detection of alpha (e.g., B.1.1.7 and Q lineages), beta (e.g., B.1.351 and descendent lineages), delta (e.g., B.1.617.2 and AY lineages), gamma (e.g., P.1 and descendent lineages), epsilon (e.g., B.1.427 and B.1.429 lineages), eta (e.g., B.1.525), iota (e.g., B.1.526), kappa (e.g., B.1.617.1), 1.617.3, mu (e.g., B.1.621, B.1.621.1), and zeta (e.g., P.2).

The treatment dose of the composition may be in a range of $10^{-5}$ to $10^4$ µmol/kg/day (µmol of drug per kg body weight per day) including all $1 \times 10^{-6}$ µmol/kg/day values and ranges therebetween. For example, the dose comprises $1 \times 10^{-6}$ µmol/kg/day to $10^4$ µmol/kg/day of protein. In embodiments, the dose may comprise $1 \times 10^{-6}$ to $100 \times 10^{-6}$ µmol/kg/day (e.g., $1 \times 10^{-6}$ to $100^{-6}$) or $10^{-6}$ to $50 \times 10^{-6}$ µmol/kg/day (e.g., $10 \times 10^{-6}$ to $50 \times 10^{-6}$) or $5 \times 10^{-6}$ to $10^{-6}$ µmol/kg/day (e.g., $5 \times 10^{-6}$ to $10 \times 10^{-6}$) or $1 \times 10^{-6}$ to $10 \times 10^{-6}$ µmol/kg/day or about $5 \times 10^{-6}$ µmol/kg/day of protein.

In an aspect, the present disclosure provides a method for treating a subject in need of treatment that has or is suspected of having cancer, comprising administering to the subject an effective amount of a composition comprising one or more H-MAP proteins described herein. The composition may be administered once or multiple times, typically over a period of days. The compositions may be delivered by any suitable route of administration, including, but not limited to, parenteral, mucosal, topical, catheter-based, oral, intravenous, or transdermal means of delivery, or the like. Parenteral delivery can include, for example, subcutaneous, intravenous, intramuscular, intraperitoneal, intercranial, intra-arterial delivery, which may be injection into the tissue of an organ.

In various embodiments, the cancers are cancers associated with and/or affected by HIF1α, p53·mdm2, Bcl-xL/Bak, and the like.

Various cancers may be treated via a method of the present disclosure. Non-limiting examples of cancers include leukemia, lung cancer (e.g., non-small cell lung cancer), dermatological cancers, premalignant lesions of the upper digestive tract, malignancies of the prostate, malignancies of the brain, malignancies of the breast, colon cancer, solid tumors, melanomas, and the like, and combinations thereof.

A subject in need of treatment may be a human or non-human mammal. Non-limiting examples of non-human mammals include cows, pigs, mice, rats, rabbits, cats, dogs, other agricultural animal, pet, service animals, and the like.

The treatment dose of the composition may be in a range of $10^{-5}$ to $10^4$ μmol/kg/day (μmol of drug per kg body weight per day) including all $1\times10^{-6}$ μmol/kg/day values and ranges therebetween. For example, the dose comprises $1\times10^{-6}$ μmol/kg/day to $10^4$ μmol/kg/day of protein. In embodiments, the dose may comprise $1\times10^{-6}$ to $100\times10^{-6}$ μmol/kg/day (e.g., $1\times10^{-6}$ to $100^{-6}$) or $10^{-6}$ to $50\times10^{-6}$ μmol/kg/day (e.g., $10\times10^{-6}$ to $50\times10^{-6}$) or $5\times10^{-6}$ to $10^{-6}$ μmol/kg/day (e.g., $5\times10^{-6}$ to $10\times10^{-6}$) or $1\times10^{-6}$ to $10\times10^{-6}$ μmol/kg/day or about $5\times10^{-6}$ μmol/kg/day of protein.

In an aspect, the present disclosure provides a method for treating a subject in need of treatment that has or is suspected of having a disease or viral infection, comprising administering to the subject an effective amount of a composition comprising one or more MAP proteins described herein. The composition may be administered once or multiple times, typically over a period of days. The compositions may be delivered by any suitable route of administration, including, but not limited to, parenteral, mucosal, topical, catheter-based, oral, intravenous, or transdermal means of delivery, or the like. Parenteral delivery can include, for example, subcutaneous, intravenous, intramuscular, intraperitoneal, intercranial, intra-arterial delivery, which may be injection into the tissue of an organ.

Various diseases or viral infections may be affected by a method of the present disclosure. For example, any disease or viral infection that involves a protein-protein interaction that involves an alpha-helical epitope may be affected. An example of such a disease is Parkinson's Disease. Examples of viruses include, but are not limited to, HIV.

A subject in need of treatment may be a human or non-human mammal. Non-limiting examples of non-human mammals include cows, pigs, mice, rats, rabbits, cats, dogs, other agricultural animal, pet, service animals, and the like.

The treatment dose of the composition may be in a range of $10^{-5}$ to $10^4$ μmol/kg/day (μmol of drug per kg body weight per day) including all $1\times10^{-6}$ μmol/kg/day values and ranges therebetween. For example, the dose comprises $1\times10^{-6}$ μmol/kg/day to $10^4$ μmol/kg/day of protein. In embodiments, the dose may comprise $1\times10^{-6}$ to $100\times10^{-6}$ μmol/kg/day (e.g., $1\times10^{-6}$ to $100^{-6}$) or $10^{-6}$ to $50\times10^{-6}$ μmol/kg/day (e.g., $10\times10^{-6}$ to $50\times10^{-6}$) or $5\times10^{-6}$ to $10^{-6}$ μmol/kg/day (e.g., $5\times10^{-6}$ to $10\times10^{-6}$) or $1\times10^{-6}$ to $10\times10^{-6}$ μmol/kg/day or about $5\times10^{-6}$ μmol/kg/day of protein.

In an aspect, the present disclosure provides uses of ACE-TAP (MAP) in diagnostics.

During infection by SARS-CoV-2, the spike (S) protein on the virus surface recognizes the peptidase domain (PD) of the angiotensin-converting enzyme 2 (ACE 2) of the host (Yan et al., Science 2020, 367 (6485), 1444-1448). Specifically, the trimeric S protein undergoes a structural rearrangement that facilitates the fusion of the viral membrane to the host cell membrane, enabling the virus to inject its RNA (Wrapp et al., Science 2020, 367 (6483), 1260-1263). The S1 subunit receptor binding domain (RBD) can present itself in the up or down conformation via a hinge-like motion. In the up state, the receptor is accessible and able to interact with ACE 2. Structural studies reveal that the N-terminal alpha helix of ACE 2 receptor is critical to binding S1 RBD (Wrapp et al., Science 2020, 367 (6483), 1260-1263). The SARS-CoV-2 RBD·ACE 2 interface possesses 17 hydrogen bonds and 1 salt bridge (FIG. 1a). These molecular interactions are crucial for infection and therefore key to the development of POC tests.

Rather than relying on a PCR-based test that requires specialized equipment for identifying SARS-CoV-2 or detecting antibodies from individuals who have recovered, the present disclosure provides a lateral-flow approach that relies on protein-protein interactions between the SARS-CoV-2 S protein and ACE protein on human cells. The probes used for the present LFAs can be antibodies that recognize various protein markers/antigens or other antibodies. Because they employ capillary force on a polymeric strip with detection zones, they are: (i) easy-to-use; (ii) eliminate the need for specialized equipment; and (iii) carried out as a single step, reducing the amount of sample handling. For detection, the present disclosure uses multivalent molecules to tag Covid-19/shedding virus or to antibodies produced in response to recovery of infection. Furthermore, the present rapid tests can be used as at-home tests that do not require skilled laboratory personnel to perform which reduces the costs of the test and makes it widely accessible for low income communities.

Generally, LFA test strips contains a test pad as the function zone, and absorbance pad as the support. Test pads can be comprised of or predominantly comprised of nitrocellulose due to its excellent capillary properties and ease of immobilization. The absorbance pad can vary and in an embodiment, can comprise polyvinyl chloride and, optionally, filter paper. The immobilization of protein molecules is based on physical absorption. Dipping, drying and spraying can be used to functionalize the testing pad. For insoluble molecules or hydrophobic substrate, binder-assisted immobilization can be effective for radioactive or enzyme labels. Gold colloid test strips can also be used in LFAs, whereby antibodies can be directly linked to gold nanoparticles, which can be loaded onto the nitrocellulose substrate.

The present design relies on the self-assembly of a coiled-coil domain of the cartilage oligomeric matrix protein (C). In an embodiment, the disclosure provides a nanomaterials in which we fuse a part or the entirety of the ACE2 region that recognizes the spike proteins to produce ACE-tagged assembled protein (ACE-TAP). In an embodiment, the disclosure provides a nanomaterial in which we fuse a part or entirety of the receptor binding domain (RBD) of the COVID-19 S-protein to yield S-tagged assembled protein (S-TAP) as multivalent detectors for corona virus and human antibody respectively. (FIG. 13b). TAP proteins are made of protein blocks, which can be designed and varied iteratively for improved functionalities, including COMPcc or its variants, purification tags, protein linkers and interacting regions. The interacting regions can be part(s) or entirety of ACE2 or S-protein or any other sequence with the desired structure and function. Examples of sequences of some of the protein blocks that can be used in the present disclosure are shown in Table 1.

Figure 14:
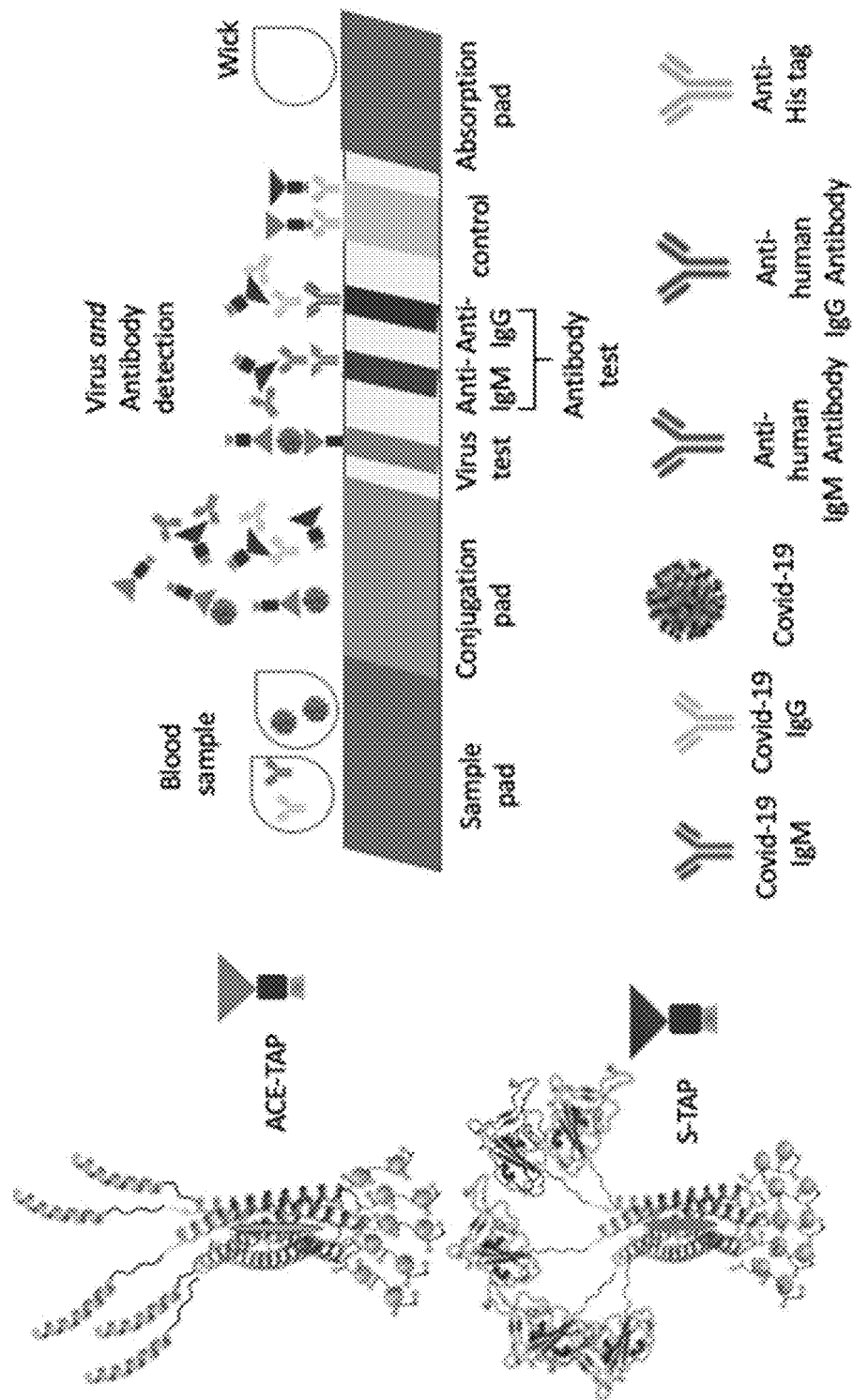
FIG. 14. ACE-TAP and S-TAP with colorimetric tag (curcumin and AuNPs) can be employed to bind Covid-19 and human antibodies (IgM or IgG), respectively, from biological samples. The virus test strip will have an untagged ACE-TAP immobilized to capture any tagged ACE-TAP bound to virus. The antibody test strip for IgM will have an anti-human IgM antibody and for IgG will have an anti-human IgG antibody. The control will bear an anti-His tag antibody to recognize unbound tagged ACE-TAP and S-TAP.
Figure 15:
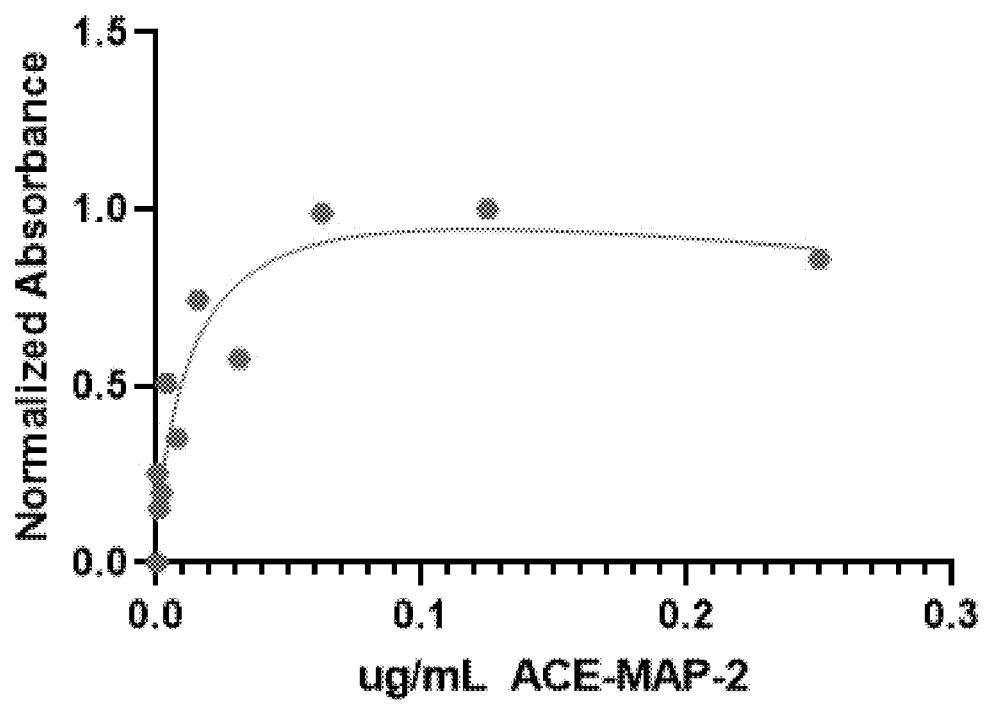
FIG. 15. ELISA fitted with total binding kinetics using Prism 7 (GraphPad) for ACE-MAP-2.
Figure 16:
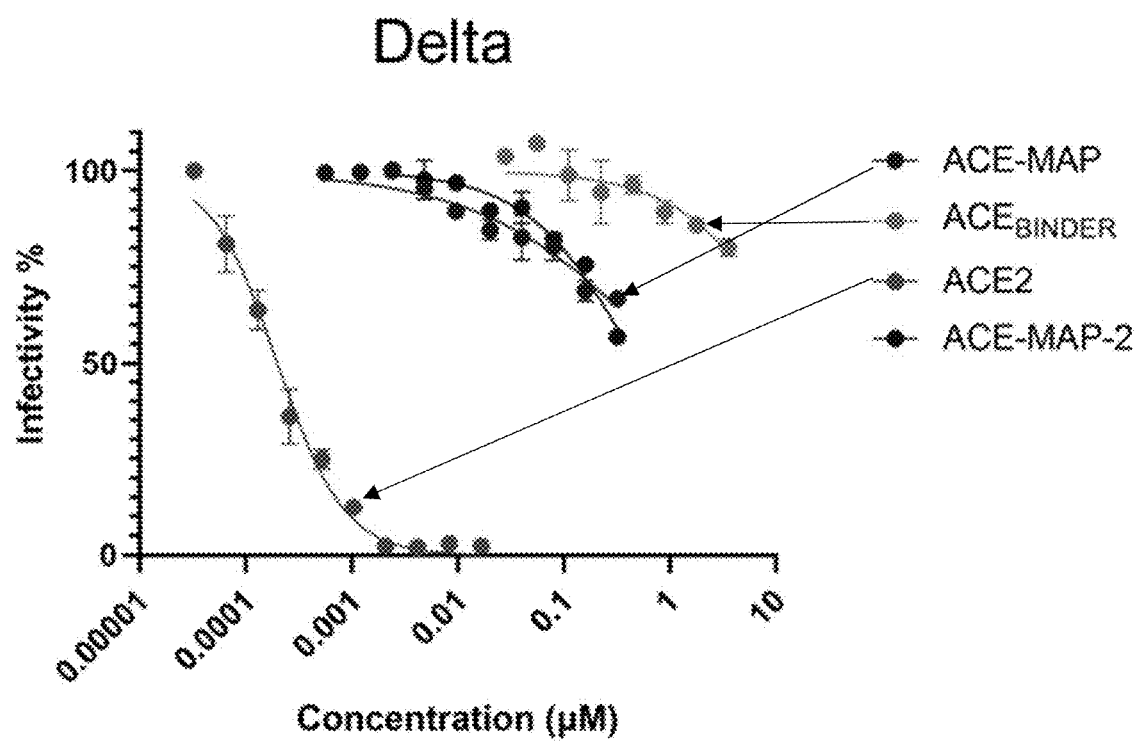
FIG. 16. Neutralization Data of ACE-MAP (ACE-TAP), $ACE_{BINDER}$, ACE2, and ACE-MAP-2 against Delta strain of SARS-CoV-2 virus with calculated IC50 values using inhibition binding kinetics in Prism 7 (GraphPad).
Figure 17:
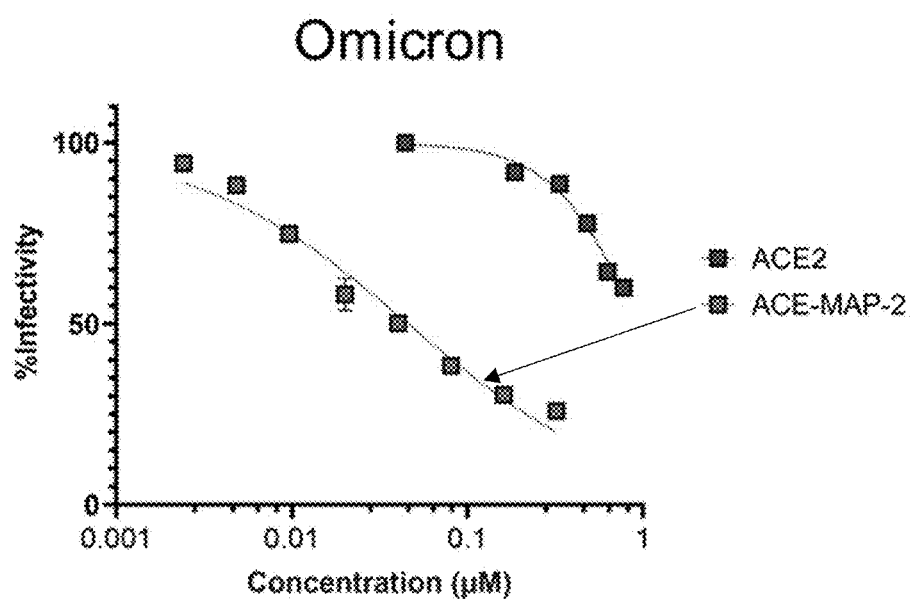
FIG. 17. Neutralization Data of ACE-MAP-2 and ACE2 against Omicron strain of SARS-CoV-2 virus.
Figure 18:
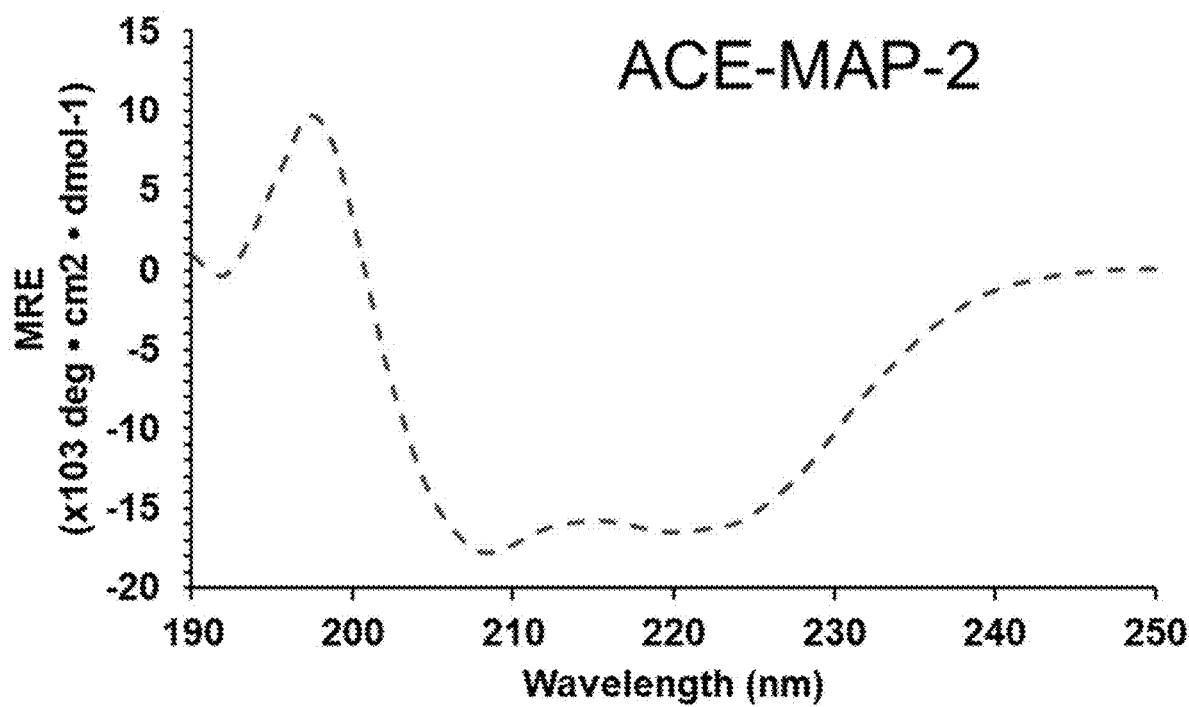
FIG. 18. Circular dichroism wavelength spectrum of ACE-MAP-2.

A multiplex lateral flow test strip (MLFTS) can be used as the detection format for the present LFA design. MLFTS can reduce production costs and improve detection efficiency by providing multiple test types on a single strip, each line containing immobilized antibodies or other binding partners that targets specific species. In an embodiment, the present MLFTS comprises, consists essentially of or consists of (i) sample pad where the sample blood or sputum or other biological sample is deposited; (ii) conjugation pad infused with ACE-TAP and S-TAP. The ACE-TAP or S-TAP are not immobilized to the conjugation pad. Rather, they are present to allow for binding to the virus or antibody and then move through the strip. The ACE-TAP and S-TAP may be physically adsorbed to the conjugation pad; (iii) a test pad with multiple lines to serve as virus, IgM, IgG antibodies and control tests; (iv) an adsorption pad; and (v) a back support or substrate (FIG. 14). The ACE-TAP and S-TAP are binding molecules that are specific the virus and the viral antibodies respectively. The test pad comprises immobilized thereto capture molecules which can capture bound virus-S-TAP complexes and bound [virus-antibody]-ACE-TAP complexes. The capture molecules may be antibodies or antigen binding fragments thereof. Examples of immobilization methods include, but are not limited to, physical adsorption (e.g., such as, for example, affinity binding through, for example, avidin and biotin, metal atoms and polyHis, and the like), entrapment, and covalent attachment/cross-linking. Methods utilizing covalent attachment/cross-linking include, but are not limited to, Michael-type reactions, thiol-ene reactions, click reactions, and the like. Other suitable covalent attachment/cross-linking reactions are known in the art.

The present MFLTS design can comprise cellulose-based materials. As the most abundant recyclable and commercially available biopolymer material for POC diagnostic tests, they have the advantage of low-cost, high thermal stability, porosity, sorption capabilities and biocompatibility. MLFTS produced with nitrocellulose membranes (NC), the key material for the test pads, and cellulose pads have been employed for numerous POC testing, including ZIKA and Covid-19 (Tsai et al., *Sci Rep* 2019, 9 (1), 15679). Pore size, porosity, surface groups' interaction between biomolecules and nanometals, and surface area of membrane pads can be modified to improve adsorption of ACE-TAP and S-TAP on test lines of immobilized biomolecules on substrate surface (analyte to pore ratio). For depositing the materials, inkjet printing (Taylor et al., *Journal of Power Sources* 2007, 171 (1), 101-106) and spraying assembly (Weng et al., *Advanced Functional Materials* 2018, 28 (44), 1803360) may be used. In an embodiment, inkjet printing can be applied to produce narrow test lines while spraying can be employed for the large area conjugation pads.

Figure 13:
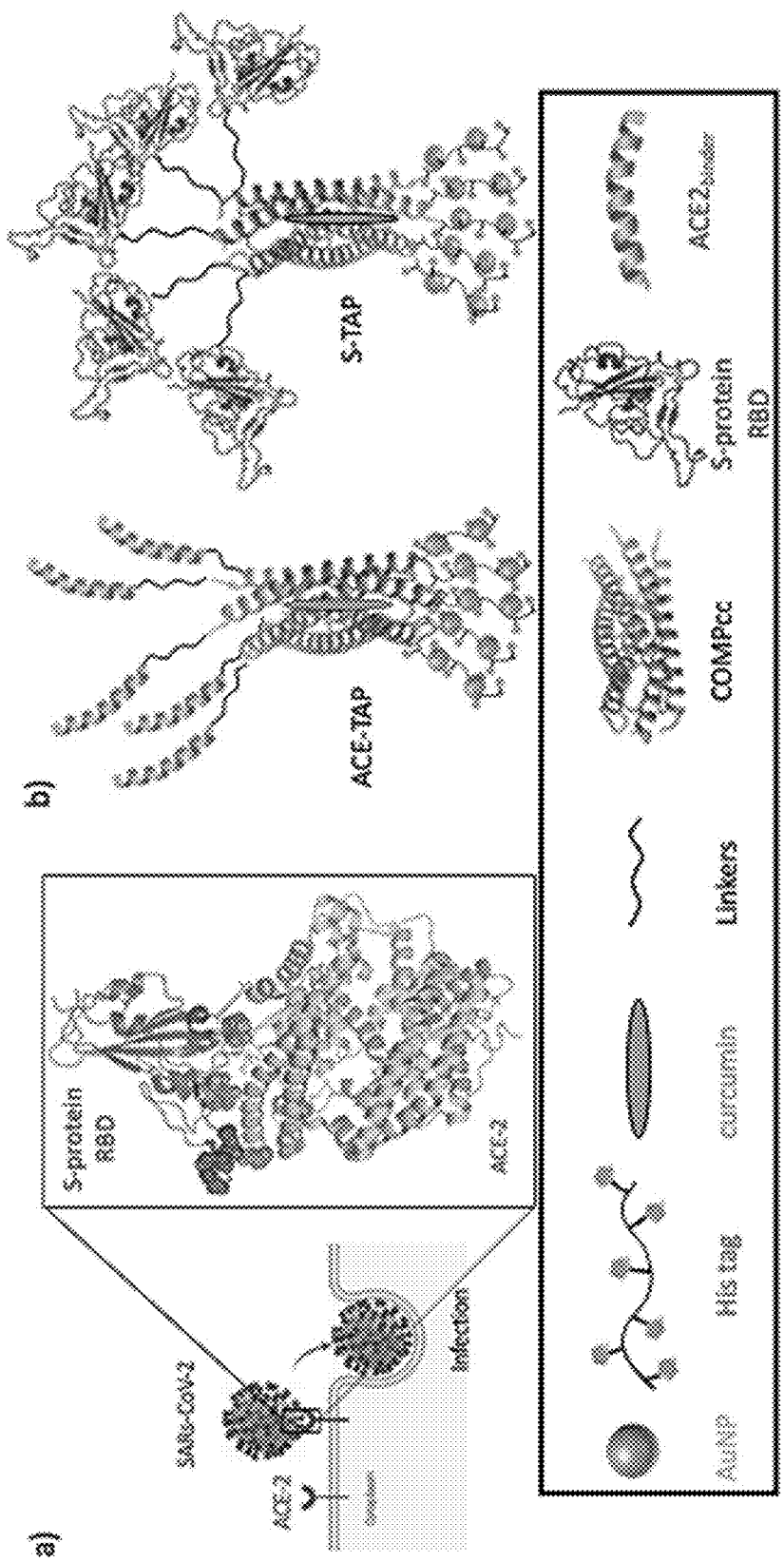
FIG. 13. a) SARS-CoV-2 S1 RBD bound to ACE2. L455, F486, N501 are critical to binding to ACE2 RBD. Dashes are the 17 hydrogen bonds, and dashes show the critical salt bridge in the interface (R439 of ACE2 to E329 of SARS-CoV-2 S1). b) The protein components of ACE-TAP and S-TAP assemblies. The S protein RBD and $ACE2_{binder}$ are fused to the C (COMPcc or ccCOMP) domain via linkers. C is able to encapsulate small molecule curcumin as well as detectable via fluorescence, while the His-tag can bind to gold nanoparticles.

In an embodiment, the coiled-coil domain of cartilage oligomeric matrix protein (ccCOMP, COMPcc, or C) fused to a variety of proteins can be used. C is an α-helical homopentamer, which forms a hydrophobic pore (7.3 nm×0.2-0.6 nm) capable of interacting with variety of small molecules (FIG. 13). Sequences and variants for C are disclosed in U.S. Pat. Nos. 8,790,709, 9,370,491, 9,453,060, 9,554,997, 9,777,041, and 10,463,752, the disclosures of which are incorporated herein by reference. The sequence of ccCOMP is:

(SEQ ID NO: 122)
GDLAPQMLRELQETNAALQDVRELLRQQVKEITFLKNTVMECDACGKLN
(wild type, wt).

Some variants are:

(SEQ ID NO: 123)
GDLAPQMLRELQETNAALQDVRELLRQQVKEITFLKNTVMESDASGKLN;

(SEQ ID NO: 124)
GDLAPQMLREAQETNAALQDVRELLRQQVKEITFLKNTVMESDASGKLN;

(SEQ ID NO: 125)
GDLAPQMLRELQEANAALQDVRELLRQQVKEITFLKNTVMESDASGKLN;

(SEQ ID NO: 126)
GDLAPQMLRELQETNAAAQDVRELLRQQVKEITFLKNTVMESDASGKLN;

(SEQ ID NO: 127)
GDLAPQMLRELQETNAALQDARELLRQQVKEITFLKNTVMESDASGKLN;

(SEQ ID NO: 128)
GDLAPQMLRELQETNAALQDVRELARQQVKEITFLKNTVMESDASGKLN;

(SEQ ID NO: 129)
GDLAPQMLRELQETNAALQDVRELLRQAVKEITFLKNTVMESDASGKLN;

(SEQ ID NO: 130)
GDLAPQMLRELQETNAALQDVRELLRQQVKEATFLKNTVMESDASGKLN;

(SEQ ID NO: 131)
GDLAPQMLRELQETNAALQDVRELLRQQVKEITFAKNTVMESDASGKLN;

(SEQ ID NO: 132)
GDLAPQMLRELQETNAALQDVRELLRQQVKEITFLKNTAMESDASGKLN;

(SEQ ID NO: 133)
GDLAPQMLRELQETNAALQDVRELLRQQVKEITFLKNTVMEADASGKLN.

Additional examples are provided in Table 1 below.

C can be engineered to exert specificity for target compounds. Using C, fusion molecules, termed herein as "tagged assembled protein" (TAP) can be generated in which the ACE or S proteins are engineered C-terminal to C yielding ACE-TAP and S-TAP, respectively. C harbors the ability to encapsulate small molecules and in an embodiment, a colorimetric marker can be entrapped/encapsulated for detection purposes. Colorimetric markers are known in the art. Examples include curcumin, Nile red, 4,4'-Dianilino-1,1'-Binaphthyl-5,5'-Disulfonic Acid, Dipotassium Salt, (Bis-ANS), 1-anilinonaphthalene-8-sulphonic acid (1,8-ANS), 8-anilino-1-naphthalene sulfonic acid (ANS), 5-dimethylaminonaphthalene-1-(N-2-aminoethyl)sulphonamide (DANSen), 1,6-Diphenyl-1,3,5-hexatriene, or 6-propionyl-2-(N,N-dimethylamino)naphthalene (PRODAN). For example, curcumin can be used as a colorimetric marker for detection. At the N-terminus, a hexahistidine can be integrated for purification and tagging with gold nanoparticles (AuNPs) for an added method of detection (FIG. 13). These multivalent nanomaterials can serve as biomolecular sensors akin to antibodies, however more sensitive due to multivalency for the detection of infection and immunity using serum, plasma, blood, saliva, sputum, spit, or tears.

MLFTS bearing ACE-TAP and S-TAP as the probes for detecting both Covid-19 virus and shed virus particles as well as antibodies in a single test. In an embodiment, the test will bear a sample pad, followed by a conjugation pad that contains the ACE-TAP and S-TAP bearing AuNPs. Downstream of the conjugation pad (in terms of the lateral flow), four detection strips bearing immobilized: ACE-TAP without AuNP for virus capture; anti-IgM for detection of the first antibody produced against Covid-19; anti-IgG for detection of the optimized antibody produced against Covid-19; and anti-His tag antibody for capturing free ACE-TAP and S-TAP bearing AuNPs (FIG. 14) can be used. The detection strips can be in any order. The substrate, conjugation chemistries and optical detection with design of the TAPs and binding sensitivity for ACE-2 and S proteins can be optimized. Materials can be immobilized using standard methods. Gold nanoparticles conjugated to COMPcc are described in U.S. Pat. No. 10,463,752, the description of which is incorporated herein by reference.

The TAP and MLFTS designs and integration are used in the present disclosure to produce an all-in-one cellulose-based test. Advantages for TAP include that the multifunctional protein-based nanomaterials can: 1) strongly bind to SARS-CoV-2 via the multivalent display of the ACE 2 sequence; 2) recognize and strongly bind to human serum antibodies via the multivalent display of the S sequence; 3) serve as a colorimetric tag via curcumin probe and AuNP binding; and 4) provide insight into sensitivity and selectivity of TAP surface display of proteins. Advantages for MLFTS design include that the inkjet/spray printing technology can be a universal method for fast protein loading where it can reach the detection limit of 25 mIU/mL.

Exemplary sequences for C (COMPcc) domain/variants, linkers (such as between S or ACE proteins and the C-terminal of COMPcc, interacting regions of S and ACE proteins for binding, are provided in Table 1 below.

TABLE 1

Sequence of protein blocks used in TAP proteins.

| | Protein Block | One-Letter Amino Acid Sequence |
|---|---|---|
| C block | COMPcc (PDB: 3v2p) | MDLAPQMLRELQETNAALQDVRELLRQQVKEITFLKNTV MECDAC (SEQ ID NO: 134) |
| | Q1 | VKEITFLKNTAPQMLRELQETNAALQDVRELLRQQ (SEQ ID NO: 135) |
| | Q2 | VKEITFLKNTAPQMLRELQETNAALQDVRELLRQQSKL (SEQ ID NO: 136) |
| | Q3 | GDLAPQMLRELQETNAALQDVRELLRQQVKEITFLKNTVM ECDACG (SEQ ID NO: 137) |
| | Q4 | GDLAPQMLRELQETNAALQDVRELLRQIVKEITFLKNTVM ECDACG (SEQ ID NO: 138) |
| | Q5 | GDLAPQMLRELQETNAALQDVRELLRQLVKEITFLKNTVM ECDACG (SEQ ID NO: 139) |
| Linkers | Kinked | LLEIWKAAAK(EAAAK)$_n$ , (n >= 2)(SEQ ID NO: 140) |
| | Rigid | LERYYKEAAK(EAAAK)$_n$ , (n >= 2) (SEQ ID NO: 141) |
| | Pro-rich1 | (XP)$_n$ |
| | N-domain1 | MRGSH$_6$GSACELA(AT)$_6$AACG (SEQ ID NO: 142) |
| | N-domain2 | LQA(AT)$_6$AVDKPIAASA (SEQ ID NO: 143) |
| | N-domain3 | MRGSH$_6$GSKPIAASA (SEQ ID NO: 144) |
| | A1 | LEGSGT (SEQ ID NO: 145) |
| | A2 | LEGSELA(AT)$_6$AACG (SEQ ID NO: 146) |
| | A3 | LQA(AT)$_6$AVDKPIAASA (SEQ ID NO: 147) |
| | Flexible1 | LQARGD(AT)$_4$AVDKPIAASA (SEQ ID NO: 148) |
| | Flexible3 | (GGGGS)$_n$ (SEQ ID NO: 22) |
| | Flexible4 | (G)$_n$ |
| | Flexible5 | A(E(A)$_3$K-E(A)$_3$K)A (SEQ ID NO: 25) |
| Interacting regions | S-protein (PDB: 6m17) | RVQPTESIVRFPNITNLCPFGEVFNATRFASVYAWNRKRISN CVADYSVLYNSASFSTFKCYGVSPTKLNDLCFTNVYADSF VIRGDEVRQIAPGQTGKIADYNYKLPDDFTGCVIAWNSNN LDSKVGGNYNYLYRLFRKSNLKPFERDISTEIYQAGSTPCN GVEGFNCYFPLQSYGFQPTNGVGYQPYRVVVLSFELLHAP ATVCGPKKSTNLVKNKCVNF (SEQ ID NO: 149) |
| | S-binder1 (PDB: 7c8w) | PNITNLCPFGEVFNATRFASVYAWNRKRISNCVADYSVLY NSASFSTFKCYGVSPTKLNDLCFTNVYADSFVIRGDEVRQI APGQTGKIADYNYKLPDDFTGCVIAWNSNNLDSKVGGNY NYLYRLFRKSNLKPFERDISTEIYQAGSTPCNGVEGFNCYFP LQSYGFQPTNGVGYQPYRVVVLSFELLHAPATVCGPKKST GTLE (SEQ ID NO: 150) |
| Interacting regions | S-binder2 (PDB: 6zcz) | TNLCPFGEVFNATRFASVYAWNRKRISNCVADYSVLYNSA SFSTFKCYGVSPTKLNDLCFTNVYADSFVIRGDEVRQIAPG QTGKIADYNYKLPDDFTGCVIAWNSNNLDSKVGGNYNYL YRLFRKSNLKPFERDISTEIYQAGSTPCNGVEGFNCYFPLQS YGFQPTNGVGYQPYRVVVLSFELLHAPATVCGKK (SEQ ID NO: 151) |
| | S-binder3 (PDB: 6vw1) | RVVPSGDVVRFPNITNLCPFGEVFNATKFPSVYAWERKKIS NCVADYSVLYNSTFFSTFKCYGVSATKLNDLCFSNVYADS FVVKGDDVRQIAPGQTGVIADYNYKLPDDFMGCVLAWNT RNIDATSTGNYNYKYRLFRKSNLKPFERDISTEIYQAGSTPC NGVEGFNCYFPLQSYGFQPTNGVGYQPYRVVVLSFELLNA PATVCGPKLSTDLIK (SEQ ID NO: 152) |
| | S-binder4 | IYQAGSTPCNGVEGFNCYFPLQSYGFQPTNGV (SEQ ID NO: 153) |

TABLE 1-continued

Sequence of protein blocks used in TAP proteins.

| Protein Block | One-Letter Amino Acid Sequence |
|---|---|
| S-binder5 | GDDVRQIAPGQTGVIADYNYKLPDDFM (SEQ ID NO: 154) |
| S-binder6 | NTRNIDATSTGNYNYKYRLFRKSNL (SEQ ID NO: 155) |
| S-binder7 | VVKGDDVRQIAPGQTGVIADYNYKLPDDFMGCVLAWNTR NIDATSTGNYNYKYRLFRKSNLKPFERDISTEIYQAGSTPCN GVEGFNCYFPLQSYGFQPTNGVGYQPYR (SEQ ID NO: 156) |
| S-binder8 (PDB: 6crv) | SDLDRCTTFDDVQAPNYTQHTSSMRGVYYPDEIFRSDTLY LTQDLFLPFYSNVTGFHTINHTFGNPVIPFKDGIYFAATEKS NVVRGWVFGSTMNNKSQSVIIINNSTNVVIRACNFELCDNP FFAVSKPMGTQTHTMIFDNAFNCTFEYISDAFSLDVSEKSG NFKHLREFVFKNKDGFLYVYKGYQPIDVVRDLPSGFNTLK PIFKLPLGINITNFRAILTAFSPAQDIWGTSAAAYFVGYLKPT TFMLKYDENGTITDAVDCSQNPLAELKCSVKSFEIDKGIYQ TSNFRVVPSGDVVRFPNITNLCPFGEVFNATKFPSVYAWER KKISNCVADYSVLYNSTFFSTFKCYGVSATKLNDLCFSNVY ADSFVVKGDDVRQIAPGQTGVIADYNYKLPDDFMGCVLA WNTRNIDATSTGNYNYKYRLRHGKLRPFERDISNVPFSPD GKPCTPPALNCYWPLNDYGFYTTTGIGYQPYRVVVLSFEL LNAPATVCGPKLSTDLIKNQCVNFNFNGLTGTGVLTPSSKR FQPFQQFGRDVSDFTDSVRDPKTSEILDISPCAFGGVSVITP GTNASSEVAVLYQDVNCTDVSTAIHADQLTPAWRIYSTGN NVFQTQAGCLIGAEHVDTSYECDIPIGAGICASYHTVSLLRS TSQKSIVAYTMSLGADSSIAYSNNTIAIPTNFSISITTEVMPV SMAKTSVDCNMYICGDSTECANLLLQYGSFCTQLNRALSG IAAEQDRNTREVFAQVKQMYKTPTLKYFGGFNFSQILPDPL KPTKRSFIEDLLFNKVTLADAGFMKQYGECLGDINARDLIC AQKFNGLTVLPPLLTDDMIAAYTAALVSGTATAGWTFGA GAALQIPFAMQMAYRFNGIGVTQNVLYENQKQIANQFNK AISQIQESLTTTSTALGKLQDVVNQNAQALNTLVKQLSSNF GAISSVLNDILSRLDPPEAEVQIDRLITGRLQSLQTYVTQQLI RAAEIRASANLAATKMSECVLGQSKRVDFCGKGYHLMSFP QAAPHGVVFLHVTYVPSQERNFTTAPAICHEGKAYFPREG VFVFNGTSWFITQRNFFSPQIITTDNTFVSGNCDVVIGIINNT VYDPLQPELDSFKEELDKYFKNHTSPDVDLGDISGINASVV NIQKEIDRLNEVAKNLNESLIDLQELGKYEQGSGYIPEAPRD GQAYVRKDGEWVLLSTFLGRSLEVLFQGPGHHHHHHHS AWSHPQFEK (SEQ ID NO: 157) |
| ACE-protein (PDB: 6m17) | MRSSSSWLLLSLVAVTAAWSHPQFEKQSTIEEQAKTFLDKF NHEAEDLFYQSSLASWNYNTNITEENVQNMNNAGDKWSA FLKEQSTLAQMYPLQEIQNLTVKLQLQALQQNGSSVLSED KSKRLNTILNTMSTIYSTGKVCNPDNPQECLLLEPGLNEIM ANSLDYNERLWAWESWRSEVGKQLRPLYEEYVVLKNEM ARANHYEDYGDYWRGDYEVNGVDGYDYSRGQLIEDVEH TFEEIKPLYEHLHAYVRAKLMNAYPSYISPIGCLPAHLLGD MWGRFWTNLYSLTVPFGQKPNIDVTDAMVDQAWDAQRIF KEAEKFFVSVGLPNMTQGFWENSMLTDPGNVQKAVCHPT AWDLGKGDFRILMCTKVTMDDFLTAHHEMGHIQYDMAY AAQPFLLRNGANEGFHEAVGEIMSLSAATPKHLKSIGLLSP DFQEDNETEINFLLKQALTIVGTLPFTYMLEKWRWMVFKG EIPKDQWMKKWWEMKREIVGVVEPVPHDETYCDPASLFH VSNDYSFIRYYTRTLYQFQFQEALCQAAKHEGPLHKCDISN STEAGQKLFNMLRLGKSEPWTLALENVVGAKNMNVRPLL NYFEPLFTWLKDQNKNSFVGWSTDWSPYADQSIKVRISLK SALGDKAYEWNDNEMYLFRSSVAYAMRQYFLKVKNQMI LFGEEDVRVANLKPRISFNFFVTAPKNVSDIIPRTEVEKAIR MSRSRINDAFRLNDNSLEFLGIQPTLGPPNQPPVSIWLIVFG VVMGVIVVGIVILIFTGIRDRKKKNKARSGENPYASIDISKG ENNPGFQNTDDVQTSF (SEQ ID NO: 158) |
| ACE-binder1 | IEEQAKTFLDKFNHEAEDLFYQS (SEQ ID NO: 159) |
| Interacting regions ACE-binder2

The present technology will aid in decreasing community spread of infection and will help mitigate the negative economic impacts of the COVID-19 pandemic. This will provide robust health information to individuals and the world alike so as to hone in contact tracing and prevent a second proliferation of the virus. Reducing spread will also decrease the acuity of COVID-19 cases and lessen the burden of a high influx of patients on the healthcare system and level the supply of high-demand life-saving equipment like respirators. This will be especially impactful in low resource communities where current testing technologies are unaffordable.

While the present disclosure provides specific reference to COVID-19 virus and antibodies, the present MLFTS can be used for detection of any virus and its antibodies in a single test.

The following Statements provide various embodiments of the present disclosure:

Statement 1. A protein comprising, consisting essentially of, or consisting of one or more $X_1$ blocks, $X_2$ blocks, and $X_3$ blocks, wherein the $X_1$ block is a coiled-coil domain, the $X_2$ block is a linker, and the $X_3$ block is a binding domain for a target protein.

Statement 2. The protein according to Statement 1, wherein the $X_1$ block comprises ccCOMP or GCN4.

Statement 3. A protein according to any one of Statements 1 or 2, wherein the protein binds to the receptor binding domain of the Spike protein of a coronavirus.

Statement 4. A protein according to any one of the preceding Statements, wherein the protein binds to the receptor binding domain of the Spike protein of SARS-CoV-2.

Statement 5. A protein according to any one of the preceding Statements, wherein the $X_1$, $X_2$, and $X_3$ blocks are oriented from the N to C-terminus as $(X_1)_a$-$(X_2)_b$-$(X_3)_c$ or $(X_3)_c$-$(X_2)_b$-$(X_1)_a$, wherein a, b, and c are the number of repeat units for the blocks.

Statement 6. A protein according to any one of the preceding Statements, wherein the $X_1$ block comprises, consists essentially of, or consists of the following sequence:

(SEQ ID NO: 3)
MRGSHHHHHHGSACELAATATATATATATAACGDLAPQMLRELQETNAAL
QDVRELLRQQVKEITFLKNTLLEIWKAAAK, (SEQ ID NO: 4)
MRGSHHHHHHGSASELAATATATATATATAASGDLAPQMLRELQETNAAL
QDVRELLRQQVKEITFLKNTLLEIWKAAAK, (SEQ ID NO: 5)
MRGSHHHHHHGSACELAATATATATATATAACGDLAPQMLRELQETNAAL
QDVRELLRQQVKEITFLKNTLLEIWK, (SEQ ID NO: 6)
MRGSHHHHHHGSASELAATATATATATATAASGDLAPQMLRELQETNAAL
QDVRELLRQQVKEITFLKNTLLEIWK, (SEQ ID NO: 172)
MRGSHHHHHHGSACELAATATATATATATAACGDLAPQMLRELQETNAAL
QDVRELLRQQVKEITFLKNT, (SEQ ID NO: 173)
MRGSHHHHHHGSASELAATATATATATATAASGDLAPQMLRELQETNAAL
QDVRELLRQQVKEITFLKNT, (SEQ ID NO: 8)
GSACELAATATATATATATAACGDLAPQMLRELQETNAALQDVRELLRQQ
VKEITFLKNTLLEIWKAAAK, (SEQ ID NO: 9)
GSASELAATATATATATATAASGDLAPQMLRELQETNAALQDVRELLRQQ
VKEITFLKNTLLEIWKAAAK, (SEQ ID NO: 10)
GSACELAATATATATATATAACGDLAPQMLRELQETNAALQDVRELLRQQ
VKEITFLKNTLLEIWK, (SEQ ID NO: 11)
GSASELAATATATATATATAASGDLAPQMLRELQETNAALQDVRELLRQQ
VKEITFLKNTLLEIWK, (SEQ ID NO: 174)
MRGSHHHHHHGSACELAATATATATATATAACGDLAPQMLRELQETNAAL
QDVRELLRQQVKEITFLKNTLLEIWK, (SEQ ID NO: 175)
MRGSHHHHHHGSASELAATATATATATATAASGDLAPQMLRELQETNAAL
QDVRELLRQQVKEITFLKNTLLEIWK, (SEQ ID NO: 12)
DLAPQMLRELQETNAALQDVRELLRQQVKEITFLKNTLLEIWKAAAK, (SEQ ID NO: 13)
DLAPQMLRELQETNAALQDVRELLRQQVKEITFLKNTLLEIWK, (SEQ ID NO: 14)
DLAPQMLRELQETNAALQDVRELLRQQVKEITFLKNT, or a sequence having at least 85% homology with any of the aforementioned sequences.

Statement 7. A protein according to any one of the preceding Statements, wherein $X_2$ comprises, consists essentially of, or consists of $(G_4S)_n$ (SEQ ID NO:22), $[EAAAK]_n$ (SEQ ID NO:176), $(EAAAK)_n$ (SEQ ID NO:23), $(PAPAP)_n$ (SEQ ID NO:24), A(EAAAK)$_4$ALEA(EAAAK)$_4$A (SEQ ID NO:25), AEAAAKEAAAKA (SEQ ID NO:26), (Ala-Pro)$_n$, VSQTSKLTRAETVFPDV (SEQ ID NO:27), PLGLWA (SEQ ID NO:28), RVLAEA (SEQ ID NO:29), EDVVCCSMSY (SEQ ID NO:30), GGIEGRGS (SEQ ID NO:31), TRHRQPRGWE (SEQ ID NO:32), AGNRVRRSVG (SEQ ID NO:33), RRRRRRRRR (SEQ ID NO:34), GFLG (SEQ ID NO:35), AAAKEAAAKEAAAK (SEQ ID NO:189), LE, $(G)_n$, or a disulfide bridge, or a sequence having at least 75% homology with any of the aforementioned sequences, where n is 1-50, including all integer values and ranges therebetween.

Statement 8. A protein according to any one of the preceding Statements, wherein $X_3$ comprises, consists essentially of, or consists of IEEQAKTFLDKFNHE-AEDLFYQS (SEQ ID NO:37), LEEQYKT-FLDKFMHELEDLLYQL (SEQ ID NO:38), IEEQAKTFLDKFNGEELLRALDQVN (SEQ ID NO:39), or a sequence having at least 85% homology with any of the aforementioned sequences.

Statement 9. A protein according to any one of the preceding Statements, wherein the molecule comprises, consists essentially of, or consists of one or more of the following sequences:

(SEQ ID NO: 40)
MRGSHHHHHHGSACELAATATATATATATATAACGDLAPQMLRELQETNAALQDVRE
LLRQQVKEITFLKNTLLEIWKAAAKEAAAKEAAAKIEEQAKTFLDKFNHEAEDLFYQ
S;

(SEQ ID NO: 41)
MRGSHHHHHHGSASELAATATATATATATATAASGDLAPQMLRELQETNAALQDVRE
LLRQQVKEITFLKNTLLEIWKAAAKEAAAKEAAAKIEEQAKTFLDKFNHEAEDLFYQ
S;

(SEQ ID NO: 42)
MRGSHHHHHHGSACELAATATATATATATATAACGDLAPQMLRELQETNAALQDVRE
LLRQQVKEITFLKNTLLEIWKAAAK(EAAAK)$_n$IEEQAKTFLDKFNHEAEDLFYQS;

(SEQ ID NO: 43)
MRGSHHHHHHGSASELAATATATATATATATAASGDLAPQMLRELQETNAALQDVRE
LLRQQVKEITFLKNTLLEIWKAAAK(EAAAK)$_n$IEEQAKTFLDKFNHEAEDLFYQS;

(SEQ ID NO: 44)
MRGSHHHHHHGSACELAATATATATATATATAACGDLAPQMLRELQETNAALQDVRE
LLRQQVKEITFLKNTLLEIWKAAAK(PAPAP)$_n$IEEQAKTFLDKFNHEAEDLFYQS;

(SEQ ID NO: 45)
MRGSHHHHHHGSASELAATATATATATATATAASGDLAPQMLRELQETNAALQDVRE
LLRQQVKEITFLKNTLLEIWKAAAK(PAPAP)$_n$IEEQAKTFLDKFNHEAEDLFYQS;

(SEQ ID NO: 46)
MRGSHHHHHHGSACELAATATATATATATATAACGDLAPQMLRELQETNAALQDVRE
LLRQQVKEITFLKNTLLEIWKAAAK(GGGGS)$_n$IEEQAKTFLDKFNHEAEDLFYQS;

(SEQ ID NO: 47)
MRGSHHHHHHGSASELAATATATATATATATAASGDLAPQMLRELQETNAALQDVRE
LLRQQVKEITFLKNTLLEIWKAAAK(GGGGS)$_n$IEEQAKTFLDKFNHEAEDLFYQS;

(SEQ ID NO: 48)
MRGSHHHHHHGSACELAATATATATATATATAACGDLAPQMLRELQETNAALQDVRE
LLRQQVKEITFLKNTLLEIWKAAAK(AT)$_n$IEEQAKTFLDKFNHEAEDLFYQS;

(SEQ ID NO: 49)
MRGSHHHHHHGSASELAATATATATATATATAASGDLAPQMLRELQETNAALQDVRE
LLRQQVKEITFLKNTLLEIWKAAAK(AT)$_n$IEEQAKTFLDKFNHEAEDLFYQS;

(SEQ ID NO: 50)
MRGSHHHHHHGSACELAATATATATATATATAACGDLAPQMLRELQETNAALQDVRE
LLRQQVKEITFLKNTLLEIWKAAAKEAAAKEAAAKLEEQYKTFLDKFMHELEDLLY
QL;

(SEQ ID NO: 51)
MRGSHHHHHHGSASELAATATATATATATATAASGDLAPQMLRELQETNAALQDVRE
LLRQQVKEITFLKNTLLEIWKAAKEAAKEAAAKLEEQYKTFLDKFMHELEDLLYQL;

(SEQ ID NO: 52)
MRGSHHHHHHGSACELAATATATATATATATAACGDLAPQMLRELQETNAALQDVRE
LLRQQVKEITFLKNTLLEIWKAAAK(EAAAK)$_n$LEEQYKTFLDKFMHELEDLLYQL;

(SEQ ID NO: 53)
MRGSHHHHHHGSASELAATATATATATATATAASGDLAPQMLRELQETNAALQDVRE
LLRQQVKEITFLKNTLLEIWKAAK(EAAAK)$_n$LEEQYKTFLDKFMHELEDLLYQL;

(SEQ ID NO: 54)
MRGSHHHHHHGSACELAATATATATATATATAACGDLAPQMLRELQETNAALQDVRE
LLRQQVKEITFLKNTLLEIWKAAK(PAPAP)$_n$LEEQYKTFLDKFMHELEDLLYQL;

(SEQ ID NO: 55)
MRGSHHHHHHGSASELAATATATATATATATAASGDLAPQMLRELQETNAALQDVRE
LLRQQVKEITFLKNTLLEIWKAAK(PAPAP)$_n$LEEQYKTFLDKFMHELEDLLYQL;

(SEQ ID NO: 56)
MRGSHHHHHHGSACELAATATATATATATATAACGDLAPQMLRELQETNAALQDVRE
LLRQQVKEITFLKNTLLEIWKAAK(GGGGS)$_n$LEEQYKTFLDKFMHELEDLLYQL;

(SEQ ID NO: 57)
MRGSHHHHHHGSASELAATATATATATATATAASGDLAPQMLRELQETNAALQDVRE
LLRQQVKEITFLKNTLLEIWKAAK(GGGGS)$_n$LEEQYKTFLDKFMHELEDLLYQL;

(SEQ ID NO: 58)
MRGSHHHHHHGSACELAATATATATATATATAACGDLAPQMLRELQETNAALQDVRE
LLRQQVKEITFLKNTLLEIWKAAK(AT)$_n$LEEQYKTFLDKFMHELEDLLYQL;

```
                                                  (SEQ ID NO: 59)
MRGSHHHHHHGSASELAATATATATATATATAASGDLAPQMLRELQETNAALQDVRE
LLRQQVKEITFLKNTLLEIWKAAK(AT)ₙLEEQYKTFLDKFMHELEDLLYQL;

(SEQ ID NO: 60)
MRGSHHHHHHGSACELAATATATATATATATAACGDLAPQMLRELQETNAALQDVRE
LLRQQVKEITFLKNTLLEIWKAAKEAAKEAAAKIEEQAKTFLDKFNGEELLRALDQV
N;

(SEQ ID NO: 61)
MRGSHHHHHHGSASELAATATATATATATATAASGDLAPQMLRELQETNAALQDVRE
LLRQQVKEITFLKNTLLEIWKAAKEAAKEAAAKIEEQAKTFLDKFNGEELLRALDQV
N;

(SEQ ID NO: 62)
MRGSPKKKRKVGGGGSHHHHHHHHGSACELAATATATATATATATAACGDLAPQML
RELQETNAALQDVRELLRQQVKEITFLKNTLLEIWKAAKEAAKEAAAKIEEQAKTFL
DKFNGEELLRALDQVN;

(SEQ ID NO: 63)
MRGSPKKKRKVGGGGSHHHHHHHHGSASELAATATATATATATATAASGDLAPQML
RELQETNAALQDVRELLRQQVKEITFLKNTLLEIWKAAKEAAKEAAAKIEEQAKTFL
DKFNGEELLRALDQVN (SEQ ID NO: 64)
MRGSHHHHHHGSACELAATATATATATATATAACGDLAPQMLRELQETNAALQDVRE
LLRQQVKEITFLKNTLLEIWKAAK(EAAAK)ₙIEEQAKTFLDKFNGEELLRALDQVN;

(SEQ ID NO: 65)
MRGSHHHHHHGSASELAATATATATATATATAASGDLAPQMLRELQETNAALQDVRE
LLRQQVKEITFLKNTLLEIWKAAK(EAAAK)ₙIEEQAKTFLDKFNGEELLRALDQVN;

(SEQ ID NO: 66)
MRGSHHHHHHGSACELAATATATATATATATAACGDLAPQMLRELQETNAALQDVRE
LLRQQVKEITFLKNTLLEIWKAAK(PAPAP)ₙIEEQAKTFLDKFNGEELLRALDQVN;

(SEQ ID NO: 67)
MRGSHHHHHHGSASELAATATATATATATATAASGDLAPQMLRELQETNAALQDVRE
LLRQQVKEITFLKNTLLEIWKAAK(PAPAP)ₙIEEQAKTFLDKFNGEELLRALDQVN;

(SEQ ID NO: 68)
MRGSHHHHHHGSACELAATATATATATATATAACGDLAPQMLRELQETNAALQDVRE
LLRQQVKEITFLKNTLLEIWKAAK(GGGGS)ₙIEEQAKTFLDKFNGEELLRALDQVN;

(SEQ ID NO: 69)
MRGSHHHHHHGSASELAATATATATATATATAASGDLAPQMLRELQETNAALQDVRE
LLRQQVKEITFLKNTLLEIWKAAK(GGGGS)ₙIEEQAKTFLDKFNGEELLRALDQVN;

(SEQ ID NO: 70)
MRGSHHHHHHGSACELAATATATATATATATAACGDLAPQMLRELQETNAALQDVRE
LLRQQVKEITFLKNTLLEIWKAAK(AT)ₙIEEQAKTFLDKFNGEELLRALDQVN;

(SEQ ID NO: 71)
MRGSHHHHHHGSASELAATATATATATATATAASGDLAPQMLRELQETNAALQDVRE
LLRQQVKEITFLKNTLLEIWKAAK(AT)ₙIEEQAKTFLDKFNGEELLRALDQVN;

(SEQ ID NO: 163)
MRGSPKKKRKVGGGGSHHHHHHHHGSACELAATATATATATATATAACGDLAPQML
RELQETNAALQDVRELLRQQVKEITFLKNTLLEIWKAAK(EAAAK)ₙIEEQAKTFLDKF
NGEELLRALDQVN;

(SEQ ID NO: 164)
MRGSPKKKRKVGGGGSHHHHHHHHGSASELAATATATATATATATAASGDLAPQML
RELQETNAALQDVRELLRQQVKEITFLKNTLLEIWKAAK(EAAAK)ₙIEEQAKTFLDKF
NGEELLRALDQVN;

(SEQ ID NO: 165)
MRGSPKKKRKVGGGGSHHHHHHHHGSACELAATATATATATATATAACGDLAPQML
RELQETNAALQDVRELLRQQVKEITFLKNTLLEIWKAAK(PAPAP)ₙIEEQAKTFLDKF
NGEELLRALDQVN;

(SEQ ID NO: 166)
MRGSPKKKRKVGGGGSHHHHHHHHGSASELAATATATATATATATAASGDLAPQML
RELQETNAALQDVRELLRQQVKEITFLKNTLLEIWKAAK(PAPAP)ₙIEEQAKTFLDKF
NGEELLRALDQVN;

(SEQ ID NO: 167)
MRGSPKKKRKVGGGGSHHHHHHHHGSACELAATATATATATATATAACGDLAPQML
RELQETNAALQDVRELLRQQVKEITFLKNTLLEIWKAAK(GGGGS)ₙIEEQAKTFLDKF
NGEELLRALDQVN;
```

(SEQ ID NO: 168)
MRGSPKKKRKVGGGGSHHHHHHHHGSASELAATATATATATATAASGDLAPQML
RELQETNAALQDVRELLRQQVKEITFLKNTLLEIWKAAK(GGGGS)ₙIEEQAKTFLDKF
NGEELLRALDQVN;

(SEQ ID NO: 169)
MRGSPKKKRKVGGGGSHHHHHHHHGSACELAATATATATATATAACGDLAPQML
RELQETNAALQDVRELLRQQVKEITFLKNTLLEIWKAAK(AT)ₙIEEQAKTFLDKFNGE
ELLRALDQVN;

(SEQ ID NO: 170)
MRGSPKKKRKVGGGGSHHHHHHHHGSASELAATATATATATATAASGDLAPQML
RELQETNAALQDVRELLRQQVKEITFLKNTLLEIWKAAK(AT)ₙIEEQAKTFLDKFNGE
ELLRALDQVN;

(SEQ ID NO: 72)
GSACELAATATATATATATAACGDLAPQMLRELQETNAALQDVRELLRQQVKEITF
LKNTLLEIWKAAKEAAKEAAAKIEEQAKTFLDKFNHEAEDLFYQS;

(SEQ ID NO: 73)
GSASELAATATATATATATAASGDLAPQMLRELQETNAALQDVRELLRQQVKEITFL
KNTLLEIWKAAAKEAAAKEAAAKIEEQAKTFLDKFNHEAEDLFYQS;

(SEQ ID NO: 74)
GSACELAATATATATATATAACGDLAPQMLRELQETNAALQDVRELLRQQVKEITF
LKNTLLEIWKAAAK(EAAAK)ₙIEEQAKTFLDKFNHEAEDLFYQS;

(SEQ ID NO: 75)
GSASELAATATATATATATAASGDLAPQMLRELQETNAALQDVRELLRQQVKEITFL
KNTLLEIWKAAAK(EAAAK)ₙIEEQAKTFLDKFNHEAEDLFYQS;

(SEQ ID NO: 76)
GSACELAATATATATATATAACGDLAPQMLRELQETNAALQDVRELLRQQVKEITF
LKNTLLEIWKAAAK(PAPAP)ₙIEEQAKTFLDKFNHEAEDLFYQS;

(SEQ ID NO: 77)
GSASELAATATATATATATAASGDLAPQMLRELQETNAALQDVRELLRQQVKEITFL
KNTLLEIWKAAAK(PAPAP)ₙIEEQAKTFLDKFNHEAEDLFYQS;

(SEQ ID NO: 78)
GSACELAATATATATATATAACGDLAPQMLRELQETNAALQDVRELLRQQVKEITF
LKNTLLEIWKAAAK(GGGGS)ₙIEEQAKTFLDKFNHEAEDLFYQS;

(SEQ ID NO: 79)
GSASELAATATATATATATAASGDLAPQMLRELQETNAALQDVRELLRQQVKEITFL
KNTLLEIWKAAAK(GGGGS)ₙIEEQAKTFLDKFNHEAEDLFYQS;

(SEQ ID NO: 80)
GSACELAATATATATATATAACGDLAPQMLRELQETNAALQDVRELLRQQVKEITF
LKNTLLEIWKAAAK(AT)ₙIEEQAKTFLDKFNHEAEDLFYQS;

(SEQ ID NO: 81)
GSASELAATATATATATATAASGDLAPQMLRELQETNAALQDVRELLRQQVKEITFL
KNTLLEIWKAAAK(AT)ₙIEEQAKTFLDKFNHEAEDLFYQS;

(SEQ ID NO: 82)
GSACELAATATATATATATAACGDLAPQMLRELQETNAALQDVRELLRQQVKEITF
LKNTLLEIWKAAKEAAKEAAAKLEEQYKTFLDKFMHELEDLLYQL;

(SEQ ID NO: 83)
GSASELAATATATATATATAASGDLAPQMLRELQETNAALQDVRELLRQQVKEITFL
KNTLLEIWKAAKEAAKEAAAKLEEQYKTFLDKFMHELEDLLYQL;

(SEQ ID NO: 84)
GSACELAATATATATATATAACGDLAPQMLRELQETNAALQDVRELLRQQVKEITF
LKNTLLEIWKAAK(EAAAK)ₙLEEQYKTFLDKFMHELEDLLYQL;

(SEQ ID NO: 85)
GSASELAATATATATATATAASGDLAPQMLRELQETNAALQDVRELLRQQVKEITFL
KNTLLEIWKAAK(EAAAK)ₙLEEQYKTFLDKFMHELEDLLYQL;

(SEQ ID NO: 86)
GSACELAATATATATATATAACGDLAPQMLRELQETNAALQDVRELLRQQVKEITF
LKNTLLEIWKAAK(PAPAP)ₙLEEQYKTFLDKFMHELEDLLYQL;

(SEQ ID NO: 87)
GSASELAATATATATATATAASGDLAPQMLRELQETNAALQDVRELLRQQVKEITFL
KNTLLEIWKAAK(PAPAP)ₙLEEQYKTFLDKFMHELEDLLYQL;

-continued (SEQ ID NO: 88)
GSACELAATATATATATATATAACGDLAPQMLRELQETNAALQDVRELLRQQVKEITF
LKNTLLEIWKAAK(GGGGS)„LEEQYKTFLDKFMHELEDLLYQL;

(SEQ ID NO: 89)
GSASELAATATATATATATATAASGDLAPQMLRELQETNAALQDVRELLRQQVKEITFL
KNTLLEIWKAAK(GGGGS)„LEEQYKTFLDKFMHELEDLLYQL;

(SEQ ID NO: 90)
GSACELAATATATATATATATAACGDLAPQMLRELQETNAALQDVRELLRQQVKEITF
LKNTLLEIWKAAK(AT)„LEEQYKTFLDKFMHELEDLLYQL;

(SEQ ID NO: 91)
GSASELAATATATATATATATAASGDLAPQMLRELQETNAALQDVRELLRQQVKEITFL
KNTLLEIWKAAK(AT)„LEEQYKTFLDKFMHELEDLLYQL;

(SEQ ID NO: 92)
GSACELAATATATATATATATAACGDLAPQMLRELQETNAALQDVRELLRQQVKEITF
LKNTLLEIWKAAKEAAKEAAAKIEEQAKTFLDKFNGEELLRALDQVN;

(SEQ ID NO: 93)
GSASELAATATATATATATATAASGDLAPQMLRELQETNAALQDVRELLRQQVKEITFL
KNTLLEIWKAAKEAAKEAAAKIEEQAKTFLDKFNGEELLRALDQVN;

(SEQ ID NO: 94)
GSACELAATATATATATATATAACGDLAPQMLRELQETNAALQDVRELLRQQVKEITF
LKNTLLEIWKAAK(EAAAK)„IEEQAKTFLDKFNGEELLRALDQVN;

(SEQ ID NO: 95)
GSASELAATATATATATATATAASGDLAPQMLRELQETNAALQDVRELLRQQVKEITFL
KNTLLEIWKAAK(EAAAK)„IEEQAKTFLDKFNGEELLRALDQVN;

(SEQ ID NO: 96)
GSACELAATATATATATATATAACGDLAPQMLRELQETNAALQDVRELLRQQVKEITF
LKNTLLEIWKAAK(PAPAP)„IEEQAKTFLDKFNGEELLRALDQVN;

(SEQ ID NO: 97)
GSASELAATATATATATATATAASGDLAPQMLRELQETNAALQDVRELLRQQVKEITFL
KNTLLEIWKAAK(PAPAP)„IEEQAKTFLDKFNGEELLRALDQVN;

(SEQ ID NO: 98)
GSACELAATATATATATATATAACGDLAPQMLRELQETNAALQDVRELLRQQVKEITF
LKNTLLEIWKAAK(GGGGS)„IEEQAKTFLDKFNGEELLRALDQVN;

(SEQ ID NO: 99)
GSASELAATATATATATATATAASGDLAPQMLRELQETNAALQDVRELLRQQVKEITFL
KNTLLEIWKAAK(GGGGS)„IEEQAKTFLDKFNGEELLRALDQVN;

(SEQ ID NO: 100)
GSACELAATATATATATATATAACGDLAPQMLRELQETNAALQDVRELLRQQVKEITF
LKNTLLEIWKAAK(AT)„IEEQAKTFLDKFNGEELLRALDQVN;

(SEQ ID NO: 101)
GSASELAATATATATATATATAASGDLAPQMLRELQETNAALQDVRELLRQQVKEITFL
KNTLLEIWKAAK(AT)„IEEQAKTFLDKFNGEELLRALDQVN;

(SEQ ID NO: 104)
DLAPQMLRELQETNAALQDVRELLRQQVKEITFLKNTLLEIWKAAAKEAAAKEAAA
KIEEQAKTFLDKFNHEAEDLFYQS;

(SEQ ID NO: 105)
DLAPQMLRELQETNAALQDVRELLRQQVKEITFLKNTLLEIWKAAAK(EAAAK)„IEE
QAKTFLDKFNHEAEDLFYQS;

(SEQ ID NO: 106)
DLAPQMLRELQETNAALQDVRELLRQQVKEITFLKNTLLEIWKAAAK(PAPAP)„IEEQ
AKTFLDKFNHEAEDLFYQS (SEQ ID NO: 107)
DLAPQMLRELQETNAALQDVRELLRQQVKEITFLKNTLLEIWKAAAK(GGGGS)„IEE
QAKTFLDKFNHEAEDLFYQS;

(SEQ ID NO: 108)
DLAPQMLRELQETNAALQDVRELLRQQVKEITFLKNTLLEIWKAAAK(AT)„IEEQAK
TFLDKFNHEAEDLFYQS;

(SEQ ID NO: 109)
DLAPQMLRELQETNAALQDVRELLRQQVKEITFLKNTLLEIWKAAKEAAKEAAAKL
EEQYKTFLDKFMHELEDLLYQL;

(SEQ ID NO: 110)
DLAPQMLRELQETNAALQDVRELLRQQVKEITFLKNTLLEIWKAAK(EAAAK)$_n$LEEQ
YKTFLDKFMHELEDLLYQL;

(SEQ ID NO: 111)
DLAPQMLRELQETNAALQDVRELLRQQVKEITFLKNTLLEIWKAAK(PAPAP)$_n$LEEQ
YKTFLDKFMHELEDLLYQL;

(SEQ ID NO: 112)
DLAPQMLRELQETNAALQDVRELLRQQVKEITFLKNTLLEIWKAAK(GGGGS)$_n$LEEQ
YKTFLDKFMHELEDLLYQL;

(SEQ ID NO: 113)
DLAPQMLRELQETNAALQDVRELLRQQVKEITFLKNTLLEIWKAAK(AT)$_n$LEEQYKT
FLDKFMHELEDLLYQL;

(SEQ ID NO: 114)
DLAPQMLRELQETNAALQDVRELLRQQVKEITFLKNTLLEIWKAAKEAAKEAAAKI
EEQAKTFLDKFNGEELLRALDQVN (SEQ ID NO: 115)
DLAPQMLRELQETNAALQDVRELLRQQVKEITFLKNTLLEIWKAAK(EAAAK)$_n$IEEQ
AKTFLDKFNGEELLRALDQVN;

(SEQ ID NO: 116)
DLAPQMLRELQETNAALQDVRELLRQQVKEITFLKNTLLEIWKAAK(PAPAP)$_n$IEEQA
KTFLDKFNGEELLRALDQVN;

(SEQ ID NO: 117)
DLAPQMLRELQETNAALQDVRELLRQQVKEITFLKNTLLEIWKAAK(GGGGS)$_n$IEEQ
AKTFLDKFNGEELLRALDQVN;
or (SEQ ID NO: 118)
DLAPQMLRELQETNAALQDVRELLRQQVKEITFLKNTLLEIWKAAK(AT)$_n$IEEQAKT
FLDKFNGEELLRALDQVN.

Statement 10. A multivalent target-binding oligomer (e.g., pentamer) formed by assembly of a plurality of (e.g., five) proteins according to any one of the preceding Statements.

Statement 11. A multivalent target-binding oligomer according to Statement 10, wherein the $X_1$ block comprises ccCOMP and the oligomer is a pentamer.

Statement 12. A multivalent target-binding oligomer according to Statement 10, wherein the $X_1$ block comprises GCN4 and the oligomer is a trimer or tetramer.

Statement 13. A multivalent target-binding pentamer according to any one of Statements 10-12, wherein the $X_1$ block comprises, consists essentially of, or consists of the following sequence:

(SEQ ID NO: 3)
MRGSHHHHHHGSACELAATATATATATATATAACGDLAPQMLRELQETNAAL
QDVRELLRQQVKEITFLKNTLLEIWKAAAK, (SEQ ID NO: 4)
MRGSHHHHHHGSASELAATATATATATATATAASGDLAPQMLRELQETNAAL
QDVRELLRQQVKEITFLKNTLLEIWKAAAK, (SEQ ID NO: 5)
MRGSHHHHHHGSACELAATATATATATATATAACGDLAPQMLRELQETNAAL
QDVRELLRQQVKEITFLKNTLLEIWK, (SEQ ID NO: 6)
MRGSHHHHHHGSASELAATATATATATATATAASGDLAPQMLRELQETNAAL
QDVRELLRQQVKEITFLKNTLLEIWK, (SEQ ID NO: 8)
GSACELAATATATATATATATAACGDLAPQMLRELQETNAALQDVRELLRQQ
VKEITFLKNTLLEIWKAAAK, (SEQ ID NO: 9)
GSASELAATATATATATATATAASGDLAPQMLRELQETNAALQDVRELLRQQ
VKEITFLKNTLLEIWKAAAK, (SEQ ID NO: 10)
GSACELAATATATATATATATAACGDLAPQMLRELQETNAALQDVRELLRQQ
VKEITFLKNTLLEIWK, (SEQ ID NO: 11)
GSASELAATATATATATATATAASGDLAPQMLRELQETNAALQDVRELLRQQ
VKEITFLKNTLLEIWK, (SEQ ID NO: 12)
DLAPQMLRELQETNAALQDVRELLRQQVKEITFLKNT, (SEQ ID NO: 13)
DLAPQMLRELQETNAALQDVRELLRQQVKEITFLKNT, (SEQ ID NO: 14)
DLAPQMLRELQETNAALQDVRELLRQQVKEITFLKNT, (SEQ ID NO: 15)
DLAPQMLRELQETNAALQDVRELLRQQVKEITFLKNT, or a sequence having at least 85% homology with any of the aforementioned sequences.

Statement 14. A multivalent target-binding pentamer according to any one of Statements 10-13, wherein $X_2$ comprises, consists essentially of, or consists of ((G$_4$S)$_n$ (SEQ ID NO:22), [EAAAK]$_n$, (SEQ ID NO:176), (EAAK)$_n$ (SEQ ID NO:23), (PAPAP)$_n$ (SEQ ID NO:24), A(EAAAK)$_4$ALEA(EAAAK)$_4$A (SEQ ID NO:25), AEAAAKEAAAKA (SEQ ID NO:26), (Ala-Pro)$_n$, VSQTSKLTRAETVFPDV (SEQ ID NO:27), PLGLWA (SEQ ID NO:28), RVLAEA (SEQ ID NO:29), EDVVCCSMSY (SEQ ID NO:30), GGIEGRGS (SEQ ID NO:31), TRHRQPRGWE (SEQ ID NO:32), AGNRVRRSVG (SEQ ID NO:33), RRRRRRRRR (SEQ ID NO:34), GFLG (SEQ ID NO:35), AAAKEAAAKEAAAK (SEQ ID NO:189), LE, (G)$_n$, or a disulfide bridge, or a sequence having at least 75% homology with any of the aforementioned sequences, where n is 1-50, including all integer values and ranges therebetween.

Statement 15. A multivalent target-binding pentamer according to any one of Statements 10-14, wherein $X_{3-5}$ comprises, consists essentially of, or consists of IEEQAKTFLDKFNHEAEDLFYQS (SEQ ID NO:37), LEEQYKTFLDKFMHELEDLLYQL (SEQ ID NO:38), IEEQAKTFLDKFNGEELLRALDQVN (SEQ ID NO:39), or a sequence having at least 85% homology with any of the aforementioned sequences.

Statement 16. A multivalent target-binding pentamer according to any one of Statements 10-15, wherein the molecule comprises, consists essentially of, or consists of one or more of the following sequences:

```
                                                  (SEQ ID NO: 40)
MRGSHHHHHHGSACELAATATATATATATAACGDLAPQMLRELQETNAALQDVRE
LLRQQVKEITFLKNTLLEIWKAAAKEAAAKEAAAKIEEQAKTFLDKFNHEAEDLFYQ
S;

(SEQ ID NO: 41)
MRGSHHHHHHGSASELAATATATATATATAASGDLAPQMLRELQETNAALQDVRE
LLRQQVKEITFLKNTLLEIWKAAAKEAAAKEAAAKIEEQAKTFLDKFNHEAEDLFYQ
S;

(SEQ ID NO: 42)
MRGSHHHHHHGSACELAATATATATATATAACGDLAPQMLRELQETNAALQDVRE
LLRQQVKEITFLKNTLLEIWKAAAK(EAAAK)ₙIEEQAKTFLDKFNHEAEDLFYQS;

(SEQ ID NO: 43)
MRGSHHHHHHGSASELAATATATATATATAASGDLAPQMLRELQETNAALQDVRE
LLRQQVKEITFLKNTLLEIWKAAAK(EAAAK)ₙIEEQAKTFLDKFNHEAEDLFYQS;

(SEQ ID NO: 44)
MRGSHHHHHHGSACELAATATATATATATAACGDLAPQMLRELQETNAALQDVRE
LLRQQVKEITFLKNTLLEIWKAAAK(PAPAP)ₙIEEQAKTFLDKFNHEAEDLFYQS;

(SEQ ID NO: 45)
MRGSHHHHHHGSASELAATATATATATATAASGDLAPQMLRELQETNAALQDVRE
LLRQQVKEITFLKNTLLEIWKAAAK(PAPAP)ₙIEEQAKTFLDKFNHEAEDLFYQS;

(SEQ ID NO: 46)
MRGSHHHHHHGSACELAATATATATATATAACGDLAPQMLRELQETNAALQDVRE
LLRQQVKEITFLKNTLLEIWKAAAK(GGGGS)ₙIEEQAKTFLDKFNHEAEDLFYQS;

(SEQ ID NO: 47)
MRGSHHHHHHGSASELAATATATATATATAASGDLAPQMLRELQETNAALQDVRE
LLRQQVKEITFLKNTLLEIWKAAAK(GGGGS)ₙIEEQAKTFLDKFNHEAEDLFYQS;

(SEQ ID NO: 48)
MRGSHHHHHHGSACELAATATATATATATAACGDLAPQMLRELQETNAALQDVRE
LLRQQVKEITFLKNTLLEIWKAAAK(AT)ₙIEEQAKTFLDKFNHEAEDLFYQS;

(SEQ ID NO: 49)
MRGSHHHHHHGSASELAATATATATATATAASGDLAPQMLRELQETNAALQDVRE
LLRQQVKEITFLKNTLLEIWKAAAK(AT)ₙIEEQAKTFLDKFNHEAEDLFYQS;

(SEQ ID NO: 50)
MRGSHHHHHHGSACELAATATATATATATAACGDLAPQMLRELQETNAALQDVRE
LLRQQVKEITFLKNTLLEIWKAAAKEAAAKEAAAKLEEQYKTFLDKFMHELEDLLYQL;

(SEQ ID NO: 51)
MRGSHHHHHHGSASELAATATATATATATAASGDLAPQMLRELQETNAALQDVRE
LLRQQVKEITFLKNTLLEIWKAAKEAAKEAAAKLEEQYKTFLDKFMHELEDLLYQL;

(SEQ ID NO: 52)
MRGSHHHHHHGSACELAATATATATATATAACGDLAPQMLRELQETNAALQDVRE
LLRQQVKEITFLKNTLLEIWKAAAK(EAAAK)ₙLEEQYKTFLDKFMHELEDLLYQL;

(SEQ ID NO: 53)
MRGSHHHHHHGSASELAATATATATATATAASGDLAPQMLRELQETNAALQDVRE
LLRQQVKEITFLKNTLLEIWKAAK(EAAAK)ₙLEEQYKTFLDKFMHELEDLLYQL;

(SEQ ID NO: 54)
MRGSHHHHHHGSACELAATATATATATATAACGDLAPQMLRELQETNAALQDVRE
LLRQQVKEITFLKNTLLEIWKAAK(PAPAP)ₙLEEQYKTFLDKFMHELEDLLYQL;

(SEQ ID NO: 55)
MRGSHHHHHHGSASELAATATATATATATAASGDLAPQMLRELQETNAALQDVRE
LLRQQVKEITFLKNTLLEIWKAAK(PAPAP)ₙLEEQYKTFLDKFMHELEDLLYQL;

(SEQ ID NO: 56)
MRGSHHHHHHGSACELAATATATATATATAACGDLAPQMLRELQETNAALQDVRE
LLRQQVKEITFLKNTLLEIWKAAK(GGGGS)ₙLEEQYKTFLDKFMHELEDLLYQL;
```

-continued (SEQ ID NO: 57)
MRGSHHHHHHGSASELAATATATATATATATAASGDLAPQMLRELQETNAALQDVRE
LLRQQVKEITFLKNTLLEIWKAAK(GGGGS)$_n$LEEQYKTFLDKFMHELEDLLYQL;

(SEQ ID NO: 58)
MRGSHHHHHHGSACELAATATATATATATATAACGDLAPQMLRELQETNAALQDVRE
LLRQQVKEITFLKNTLLEIWKAAK(AT)$_n$LEEQYKTFLDKFMHELEDLLYQL;

(SEQ ID NO: 59)
MRGSHHHHHHGSASELAATATATATATATATAASGDLAPQMLRELQETNAALQDVRE
LLRQQVKEITFLKNTLLEIWKAAK(AT)$_n$LEEQYKTFLDKFMHELEDLLYQL;

(SEQ ID NO: 60)
MRGSHHHHHHGSACELAATATATATATATATAACGDLAPQMLRELQETNAALQDVRE
LLRQQVKEITFLKNTLLEIWKAAKEAAKEAAAKIEEQAKTFLDKFNGEELLRALDQVN;

(SEQ ID NO: 61)
MRGSHHHHHHGSASELAATATATATATATATAASGDLAPQMLRELQETNAALQDVRE
LLRQQVKEITFLKNTLLEIWKAAKEAAKEAAAKIEEQAKTFLDKFNGEELLRALDQV
N;

(SEQ ID NO: 62)
MRGSPKKKRKVGGGGSHHHHHHHHGSACELAATATATATATATATAACGDLAPQML
RELQETNAALQDVRELLRQQVKEITFLKNTLLEIWKAAKEAAKEAAAKIEEQAKTFL
DKFNGEELLRALDQVN;

(SEQ ID NO: 63)
MRGSPKKKRKVGGGGSHHHHHHHHGSASELAATATATATATATATAASGDLAPQML
RELQETNAALQDVRELLRQQVKEITFLKNTLLEIWKAAKEAAKEAAAKIEEQAKTFL
DKFNGEELLRALDQVN (SEQ ID NO: 64)
MRGSHHHHHHGSACELAATATATATATATATAACGDLAPQMLRELQETNAALQDVRE
LLRQQVKEITFLKNTLLEIWKAAK(EAAAK)$_n$IEEQAKTFLDKFNGEELLRALDQVN;

(SEQ ID NO: 65)
MRGSHHHHHHGSASELAATATATATATATATAASGDLAPQMLRELQETNAALQDVRE
LLRQQVKEITFLKNTLLEIWKAAK(EAAAK)$_n$IEEQAKTFLDKFNGEELLRALDQVN;

(SEQ ID NO: 66)
MRGSHHHHHHGSACELAATATATATATATATAACGDLAPQMLRELQETNAALQDVRE
LLRQQVKEITFLKNTLLEIWKAAK(PAPAP)$_n$IEEQAKTFLDKFNGEELLRALDQVN;

(SEQ ID NO: 67)
MRGSHHHHHHGSASELAATATATATATATATAASGDLAPQMLRELQETNAALQDVRE
LLRQQVKEITFLKNTLLEIWKAAK(PAPAP)$_n$IEEQAKTFLDKFNGEELLRALDQVN;

(SEQ ID NO: 68)
MRGSHHHHHHGSACELAATATATATATATATAACGDLAPQMLRELQETNAALQDVRE
LLRQQVKEITFLKNTLLEIWKAAK(GGGGS)$_n$IEEQAKTFLDKFNGEELLRALDQVN;

(SEQ ID NO: 69)
MRGSHHHHHHGSASELAATATATATATATATAASGDLAPQMLRELQETNAALQDVRE
LLRQQVKEITFLKNTLLEIWKAAK(GGGGS)$_n$IEEQAKTFLDKFNGEELLRALDQVN;

(SEQ ID NO: 70)
MRGSHHHHHHGSACELAATATATATATATATAACGDLAPQMLRELQETNAALQDVRE
LLRQQVKEITFLKNTLLEIWKAAK(AT)$_n$IEEQAKTFLDKFNGEELLRALDQVN;

(SEQ ID NO: 71)
MRGSHHHHHHGSASELAATATATATATATATAASGDLAPQMLRELQETNAALQDVRE
LLRQQVKEITFLKNTLLEIWKAAK(AT)$_n$IEEQAKTFLDKFNGEELLRALDQVN;

(SEQ ID NO: 163)
MRGSPKKKRKVGGGGSHHHHHHHHGSACELAATATATATATATATAACGDLAPQML
RELQETNAALQDVRELLRQQVKEITFLKNTLLEIWKAAK(EAAAK)$_n$IEEQAKTFLDKF
NGEELLRALDQVN;

(SEQ ID NO: 164)
MRGSPKKKRKVGGGGSHHHHHHHHGSASELAATATATATATATATAASGDLAPQML
RELQETNAALQDVRELLRQQVKEITFLKNTLLEIWKAAK(EAAAK)$_n$IEEQAKTFLDKF
NGEELLRALDQVN;

(SEQ ID NO: 165)
MRGSPKKKRKVGGGGSHHHHHHHHGSACELAATATATATATATATAACGDLAPQML
RELQETNAALQDVRELLRQQVKEITFLKNTLLEIWKAAK(PAPAP)$_n$IEEQAKTFLDKF
NGEELLRALDQVN;

-continued (SEQ ID NO: 166)
MRGSPKKKRKVGGGGSHHHHHHHHGSASELAATATATATATATATAASGDLAPQML
RELQETNAALQDVRELLRQQVKEITFLKNTLLEIWKAAK(PAPAP)$_n$IEEQAKTFLDKF
NGEELLRALDQVN;

(SEQ ID NO: 167)
MRGSPKKKRKVGGGGSHHHHHHHHGSACELAATATATATATATATAACGDLAPQML
RELQETNAALQDVRELLRQQVKEITFLKNTLLEIWKAAK(GGGGS)$_n$IEEQAKTFLDKF
NGEELLRALDQVN;

(SEQ ID NO: 168)
MRGSPKKKRKVGGGGSHHHHHHHHGSASELAATATATATATATATAASGDLAPQML
RELQETNAALQDVRELLRQQVKEITFLKNTLLEIWKAAK(GGGGS)$_n$IEEQAKTFLDKF
NGEELLRALDQVN;

(SEQ ID NO: 169)
MRGSPKKKRKVGGGGSHHHHHHHHGSACELAATATATATATATATAACGDLAPQML
RELQETNAALQDVRELLRQQVKEITFLKNTLLEIWKAAK(AT)$_n$IEEQAKTFLDKFNGE
ELLRALDQVN;

(SEQ ID NO: 170)
MRGSPKKKRKVGGGGSHHHHHHHHGSASELAATATATATATATATAASGDLAPQML
RELQETNAALQDVRELLRQQVKEITFLKNTLLEIWKAAK(AT)$_n$IEEQAKTFLDKFNGE
ELLRALDQVN;

(SEQ ID NO: 72)
GSACELAATATATATATATATAACGDLAPQMLRELQETNAALQDVRELLRQQVKEITF
LKNTLLEIWKAAKEAAKEAAAKIEEQAKTFLDKFNHEAEDLFYQS;

(SEQ ID NO: 73)
GSASELAATATATATATATATAASGDLAPQMLRELQETNAALQDVRELLRQQVKEITFL
KNTLLEIWKAAKEAAKEAAAKIEEQAKTFLDKFNHEAEDLFYQS;

(SEQ ID NO: 74)
GSACELAATATATATATATATAACGDLAPQMLRELQETNAALQDVRELLRQQVKEITF
LKNTLLEIWKAAAK(EAAAK)$_n$IEEQAKTFLDKFNHEAEDLFYQS;

(SEQ ID NO: 75)
GSASELAATATATATATATATAASGDLAPQMLRELQETNAALQDVRELLRQQVKEITFL
KNTLLEIWKAAAK(EAAAK)$_n$IEEQAKTFLDKFNHEAEDLFYQS;

(SEQ ID NO: 76)
GSACELAATATATATATATATAACGDLAPQMLRELQETNAALQDVRELLRQQVKEITF
LKNTLLEIWKAAAK(PAPAP)$_n$IEEQAKTFLDKFNHEAEDLFYQS;

(SEQ ID NO: 77)
GSASELAATATATATATATATAASGDLAPQMLRELQETNAALQDVRELLRQQVKEITFL
KNTLLEIWKAAAK(PAPAP)$_n$IEEQAKTFLDKFNHEAEDLFYQS;

(SEQ ID NO: 78)
GSACELAATATATATATATATAACGDLAPQMLRELQETNAALQDVRELLRQQVKEITF
LKNTLLEIWKAAAK(GGGGS)$_n$IEEQAKTFLDKFNHEAEDLFYQS;

(SEQ ID NO: 79)
GSASELAATATATATATATATAASGDLAPQMLRELQETNAALQDVRELLRQQVKEITFL
KNTLLEIWKAAAK(GGGGS)$_n$IEEQAKTFLDKFNHEAEDLFYQS;

(SEQ ID NO: 80)
GSACELAATATATATATATATAACGDLAPQMLRELQETNAALQDVRELLRQQVKEITF
LKNTLLEIWKAAAK(AT)$_n$IEEQAKTFLDKFNHEAEDLFYQS;

(SEQ ID NO: 81)
GSASELAATATATATATATATAASGDLAPQMLRELQETNAALQDVRELLRQQVKEITFL
KNTLLEIWKAAAK(AT)$_n$IEEQAKTFLDKFNHEAEDLFYQS;

(SEQ ID NO: 82)
GSACELAATATATATATATATAACGDLAPQMLRELQETNAALQDVRELLRQQVKEITF
LKNTLLEIWKAAKEAAKEAAAKLEEQYKTFLDKFMHELEDLLYQL;

(SEQ ID NO: 83)
GSASELAATATATATATATATAASGDLAPQMLRELQETNAALQDVRELLRQQVKEITFL
KNTLLEIWKAAKEAAKEAAAKLEEQYKTFLDKFMHELEDLLYQL;

(SEQ ID NO: 84)
GSACELAATATATATATATATAACGDLAPQMLRELQETNAALQDVRELLRQQVKEITF
LKNTLLEIWKAAAK(EAAAK)$_n$LEEQYKTFLDKFMHELEDLLYQL;

(SEQ ID NO: 85)
GSASELAATATATATATATATAASGDLAPQMLRELQETNAALQDVRELLRQQVKEITFL
KNTLLEIWKAAAK(EAAAK)$_n$LEEQYKTFLDKFMHELEDLLYQL;

-continued (SEQ ID NO: 86)
GSACELAATATATATATATATAACGDLAPQMLRELQETNAALQDVRELLRQQVKEITF
LKNTLLEIWKAAK(PAPAP)„LEEQYKTFLDKFMHELEDLLYQL;

(SEQ ID NO: 87)
GSASELAATATATATATATATAASGDLAPQMLRELQETNAALQDVRELLRQQVKEITFL
KNTLLEIWKAAK(PAPAP)„LEEQYKTFLDKFMHELEDLLYQL;

(SEQ ID NO: 88)
GSACELAATATATATATATATAACGDLAPQMLRELQETNAALQDVRELLRQQVKEITF
LKNTLLEIWKAAK(GGGGS)„LEEQYKTFLDKFMHELEDLLYQL;

(SEQ ID NO: 89)
GSASELAATATATATATATATAASGDLAPQMLRELQETNAALQDVRELLRQQVKEITFL
KNTLLEIWKAAK(GGGGS)„LEEQYKTFLDKFMHELEDLLYQL;

(SEQ ID NO: 90)
GSACELAATATATATATATATAACGDLAPQMLRELQETNAALQDVRELLRQQVKEITF
LKNTLLEIWKAAK(AT)„LEEQYKTFLDKFMHELEDLLYQL;

(SEQ ID NO: 91)
GSASELAATATATATATATATAASGDLAPQMLRELQETNAALQDVRELLRQQVKEITFL
KNTLLEIWKAAK(AT)„LEEQYKTFLDKFMHELEDLLYQL;

(SEQ ID NO: 92)
GSACELAATATATATATATATAACGDLAPQMLRELQETNAALQDVRELLRQQVKEITF
LKNTLLEIWKAAKEAAKEAAAKIEEQAKTFLDKFNGEELLRALDQVN;

(SEQ ID NO: 93)
GSASELAATATATATATATATAASGDLAPQMLRELQETNAALQDVRELLRQQVKEITFL
KNTLLEIWKAAKEAAKEAAAKIEEQAKTFLDKFNGEELLRALDQVN;

(SEQ ID NO: 94)
GSACELAATATATATATATATAACGDLAPQMLRELQETNAALQDVRELLRQQVKEITF
LKNTLLEIWKAAK(EAAAK)„IEEQAKTFLDKFNGEELLRALDQVN;

(SEQ ID NO: 95)
GSASELAATATATATATATATAASGDLAPQMLRELQETNAALQDVRELLRQQVKEITFL
KNTLLEIWKAAK(EAAAK)„IEEQAKTFLDKFNGEELLRALDQVN;

(SEQ ID NO: 96)
GSACELAATATATATATATATAACGDLAPQMLRELQETNAALQDVRELLRQQVKEITF
LKNTLLEIWKAAK(PAPAP)„IEEQAKTFLDKFNGEELLRALDQVN;

(SEQ ID NO: 97)
GSASELAATATATATATATATAASGDLAPQMLRELQETNAALQDVRELLRQQVKEITFL
KNTLLEIWKAAK(PAPAP)„IEEQAKTFLDKFNGEELLRALDQVN;

(SEQ ID NO: 98)
GSACELAATATATATATATATAACGDLAPQMLRELQETNAALQDVRELLRQQVKEITF
LKNTLLEIWKAAK(GGGGS)„IEEQAKTFLDKFNGEELLRALDQVN;

(SEQ ID NO: 99)
GSASELAATATATATATATATAASGDLAPQMLRELQETNAALQDVRELLRQQVKEITFL
KNTLLEIWKAAK(GGGGS)„IEEQAKTFLDKFNGEELLRALDQVN;

(SEQ ID NO: 100)
GSACELAATATATATATATATAACGDLAPQMLRELQETNAALQDVRELLRQQVKEITF
LKNTLLEIWKAAK(AT)„IEEQAKTFLDKFNGEELLRALDQVN;

(SEQ ID NO: 101)
GSASELAATATATATATATATAASGDLAPQMLRELQETNAALQDVRELLRQQVKEITFL
KNTLLEIWKAAK(AT)„IEEQAKTFLDKFNGEELLRALDQVN;

(SEQ ID NO: 104)
DLAPQMLRELQETNAALQDVRELLRQQVKEITFLKNTLLEIWKAAAKEAAAKEAAA
KIEEQAKTFLDKFNHEAEDLFYQS;

(SEQ ID NO: 105)
DLAPQMLRELQETNAALQDVRELLRQQVKEITFLKNTLLEIWKAAAK(EAAAK)„IEE
QAKTFLDKFNHEAEDLFYQS;

(SEQ ID NO: 106)
DLAPQMLRELQETNAALQDVRELLRQQVKEITFLKNTLLEIWKAAAK(PAPAP)„IEEQ
AKTFLDKFNHEAEDLFYQS (SEQ ID NO: 107)
DLAPQMLRELQETNAALQDVRELLRQQVKEITFLKNTLLEIWKAAAK(GGGGS)„IEE
QAKTFLDKFNHEAEDLFYQS;

-continued (SEQ ID NO: 108)
DLAPQMLRELQETNAALQDVRELLRQQVKEITFLKNTLLEIWKAAAK(AT)ₙIEEQAK
TFLDKFNHEAEDLFYQS;

(SEQ ID NO: 109)
DLAPQMLRELQETNAALQDVRELLRQQVKEITFLKNTLLEIWKAAKEAAKEAAAKL
EEQYKTFLDKFMHELEDLLYQL;

(SEQ ID NO: 110)
DLAPQMLRELQETNAALQDVRELLRQQVKEITFLKNTLLEIWKAAK(EAAAK)ₙLEEQ
YKTFLDKFMHELEDLLYQL;

(SEQ ID NO: 111)
DLAPQMLRELQETNAALQDVRELLRQQVKEITFLKNTLLEIWKAAK(PAPAP)ₙLEEQ
YKTFLDKFMHELEDLLYQL;

(SEQ ID NO: 112)
DLAPQMLRELQETNAALQDVRELLRQQVKEITFLKNTLLEIWKAAK(GGGGS)ₙLEEQ
YKTFLDKFMHELEDLLYQL;

(SEQ ID NO: 113)
DLAPQMLRELQETNAALQDVRELLRQQVKEITFLKNTLLEIWKAAK(AT)ₙLEEQYKT
FLDKFMHELEDLLYQL;

(SEQ ID NO: 114)
DLAPQMLRELQETNAALQDVRELLRQQVKEITFLKNTLLEIWKAAKEAAKEAAAKI
EEQAKTFLDKFNGEELLRALDQVN (SEQ ID NO: 115)
DLAPQMLRELQETNAALQDVRELLRQQVKEITFLKNTLLEIWKAAK(EAAAK)ₙIEEQ
AKTFLDKFNGEELLRALDQVN;

(SEQ ID NO: 116)
DLAPQMLRELQETNAALQDVRELLRQQVKEITFLKNTLLEIWKAAK(PAPAP)ₙIEEQA
KTFLDKFNGEELLRALDQVN;

(SEQ ID NO: 117)
DLAPQMLRELQETNAALQDVRELLRQQVKEITFLKNTLLEIWKAAK(GGGGS)ₙIEEQ
AKTFLDKFNGEELLRALDQVN;
or (SEQ ID NO: 118)
DLAPQMLRELQETNAALQDVRELLRQQVKEITFLKNTLLEIWKAAK(AT)ₙIEEQAKT
FLDKFNGEELLRALDQVN.

Statement 17. A method for treatment of SARS-CoV-2 infection and/or cancer and/or a disease and/or a viral infection in a subject in need of treatment comprising administering to a subject in need of treatment a composition comprising a therapeutically effective amount of a multivalent target-binding pentamer according to any one of Statements 10-15.

Statement 18. A method according to Statement 17, wherein the subject in need of treatment is symptomatic or asymptomatic of the SARS-CoV-2 infection.

Statement 19. The method according to Statement 18, wherein the SARS-CoV-2 infection is caused by a SARS-CoV-2 variant alpha, beta, delta, gamma, epsilon, eta, iota, kappa, mu, and/or zeta.

Statement 20. A method of prevention or reducing the severity of SARS-CoV-2 infection comprising administering to a subject in need of prevention a composition comprising a therapeutically effective amount of a multivalent target-binding pentamer according to any one of Statements 10-15.

Statement 21. A method according to Statement 20, wherein the subject is at a risk of contracting the SARS-CoV-2 infection.

Statement 22. A method according to Statement 21, wherein the SARS-CoV-2 infection is caused by a SARS-CoV-2 variant alpha, beta, delta, gamma, epsilon, eta, iota, kappa, mu, and/or zeta.

Statement 23. A method of reducing the severity of an already contracted SARS-CoV-2 infection, or an expected SARS-CoV-2 infection comprising administering to the subject a composition comprising an effective amount of a multivalent target-binding pentamer according to any one of Statements 10-15.

Statement 24. A method according to Statement 23, wherein the SARS-CoV-2 infection is caused by a SARS-CoV-2 variant alpha, beta, delta, gamma, epsilon, eta, iota, kappa, mu, and/or zeta.

Statement 25. A test strip disposed on a substrate, wherein the test strip comprises: i) a sample application zone for deposition of a biological sample comprising virus and/or antibodies; ii) a conjugation zone, wherein the conjugation zone comprises adsorbed binding molecules that specifically bind to the virus or the antibodies in the biological sample; iii) a capture zone comprising capture molecules immobilized to the substrate in the zone to separately and distinctly capture the virus bound to virus-specific binding molecule and the antibodies bound to antibody-specific binding molecules, and optionally unbound capture molecules; and iv) optionally an absorption zone for removal of fluid, wherein the sample application zone, the conjugation zone, and the capture zone are in a path of liquid flow over the substrate such that during a test run, a liquid will flow distally and sequentially through the sample application zone, the conjugation zone, the capture zone and the absorption zone.

Statement 26. A test strip according to Statement 25, wherein the virus is SARS-CoV-2 and the antibodies are against SARS-CoV-2.

Statement 27. A test strip according to Statements 25 or 26, wherein the virus-specific binding molecule is S-TAP and antibody-specific binding molecule is ACE-TAP.

Statement 28. A test strip according to any one of Statements 25-27, wherein separate sub-zones are present, each separate sub-zone comprising immobilized capture molecules to only capture ACE-TAP, S-TAP, IgG, IgM or IgA.

Statement 29. A test strip according to any one of Statements 25-28, wherein a sub-zone of the capture zone is a control zone which comprises immobilized capture molecules to only capture unbound ACE-TAP and unbound S-TAP.

Statement 30. A method of detecting the presence of SARS-CoV-2 virus, antibody directed to SARS-CoV-2 or both simultaneously, comprising: i) depositing a biological liquid sample obtained from an individual suspected of currently having or being previously exposed to SARS-CoV-2 virus on the sample application zone of the test strip according to any one of Statements 25-29, ii) allowing the liquid sample to flow over the test strip in a direction from the sample deposition zone to the absorption zone in such a manner that if virus or antibodies are present, a detectable signal at the specific test strip is observed.

Statement 31. A method according to Statement 30, wherein the biological liquid sample may be undiluted sample obtained from an individual or may be diluted with a suitable liquid, such as buffer or saline.

Statement 32. A method according to Statements 30 or 31, wherein the biological liquid sample is blood, plasma, serum, any fraction of blood, saliva, mucous sample, urine, tears, sweat or any other liquid sample from a biological system.

Statement 33. A method according to any one of Statements 30-33, wherein the individual is a human.

Statement 34. A SARS-CoV-2 virus binding molecule or SARS-CoV-2 antibody binding molecule comprising: i) COMPcc peptide; ii) ACE binder region protein or peptide or S-binder region peptide, which are C-terminal to the COMPcc peptide; iii) a hexahistidine tag, which is N-terminal to the COMPcc peptide; and iv) optionally, gold nanoparticles integrated to the hexahistidine tag.

Statement 35. A SARS-CoV-2 virus binding molecule according to Statement 34, further comprising a detectable molecule in the pore of COMPcc.

Statement 36. A SARS-CoV-2 virus binding molecule according to Statements 34 or 35, wherein the detectable molecule is a colorimetric molecule.

Statement 37. A SARS-CoV-2 virus binding molecule according to any one of Statements 34-36, wherein the colorimetric molecule is curcumin, Nile red, 4,4'-Dianilino-1,1'-Binaphthyl-5,5'-Disulfonic Acid, Dipotassium Salt, (Bis-ANS), 1-anilinonaphthalene-8-sulphonic acid (1,8-ANS), 8-anilino-1-naphthalene sulfonic acid (ANS), 5-dimethylaminonaphthalene-1-(N-2-aminoethyl)sulphonamide (DANSen), 1,6-Diphenyl-1,3,5-hexatriene, or 6-propionyl-2-(N,N-dimethylamino)naphthalene (PRODAN).

Statement 38. A SARS-CoV-2 virus binding molecule according to any one of Statements 34-37, wherein the sequence of COMPcc peptide, the ACE-binder region, the S-binder region is selected from one of the listed sequences in Table 1 or disclosed herein.

The following examples are provided as illustrative examples and are not intended to be restrictive in any way.

Example 1

Described are the results of an ACE2 fused, multivalent assembled protein (ACE-MAP) where the N-terminal alpha helix ($ACE_{BINDER}$) is joined with a computationally designed kinked linker to C leading to high binding affinity of SARS-CoV-2 RBD for future applications as a biosensor or therapeutic. ACE-MAP joins only one other reported thermostable antibody-mimics with picomolar binding affinity to the SARS-CoV-2 RBD as a potential therapeutic for COVID-19.

Chemically competent AFIQ E. coli cells were gifted from David Tirrell at California Institute of Technology. ACE-MAP/pQE30 plasmid was cloned and purchased from Eurofins. Bacto-tryptone, sodium chloride, yeast extract, tryptic soy agar, ampicillin, chloramphenicol, sodium phosphate dibasic anhydrous ($Na_2HPO_4$), sodium hydroxide (NaOH), dextrose monohydrate (D-glucose), magnesium sulfate, calcium chloride ($CaCl_2$)), manganese chloride tetrahydrate ($MnCl_2 \cdot 4H_2O$), cobaltous chloride hexahydrate ($CoCl_2 \cdot 6H_2O$), isopropyl β-D-1-thiogalactopyranoside (IPTG), Pierce bicinchoninic acid (BCA) assay kit, Pierce snakeskin dialysis tubing 3.5 K MWCO, sodium dodecyl sulfate, Pierce C18 tips with 10 μL bed, bissulfosuccinimidyl suberrate ($BS^3$), ascorbic acid, Immulon 4 HBX ninety-six well plates, Nunc ninety-six well plates, Dulbecco's Modified Eagle medium (DMEM), Nunc EasYFlask Cell Culture Flasks, Quant-iT PicoGreen dsDNA Assay Kit, IL-6 Mouse ELISA Kit, Pierce High Capacity Endotoxin Removal Spin Columns, and ELISA wash buffer (30×) were acquired from Thermo Fisher Scientific. The twenty naturally occurring amino acids, thiamine hydrochloride (vitamin B), dimethylsulfoxide (DMSO), and 3,3',5,5'-tetramethylbenzidine (TMB) were purchased from Sigma Aldrich. Hydrochloric acid (HCl), Coomassie® Brilliant Blue G-250, and milk powder (non-fat, skimmed) were purchased from VWR. HiTrap Q HP 5 mL columns for protein purification were purchased from GE Healthcare Life Sciences. Macrosep and Microsep Advance Centrifugal Devices 3K molecular weight cutoff (MWCO) and 0.2 μm syringe filters were purchased from PALL. Acrylamide/bis solution (30%) 29:1, Mini Trans-Blot filer paper, Trans-Blot Transfer Medium (nitrocellulose membrane), and natural polypeptide sodium dodecyl sulphate-polyacrylamide gel electrophoresis (SDS-PAGE) standard were purchased from Bio-Rad, and Dulbecco's phosphate buffered saline were purchased from ATCC.

Figure 7:
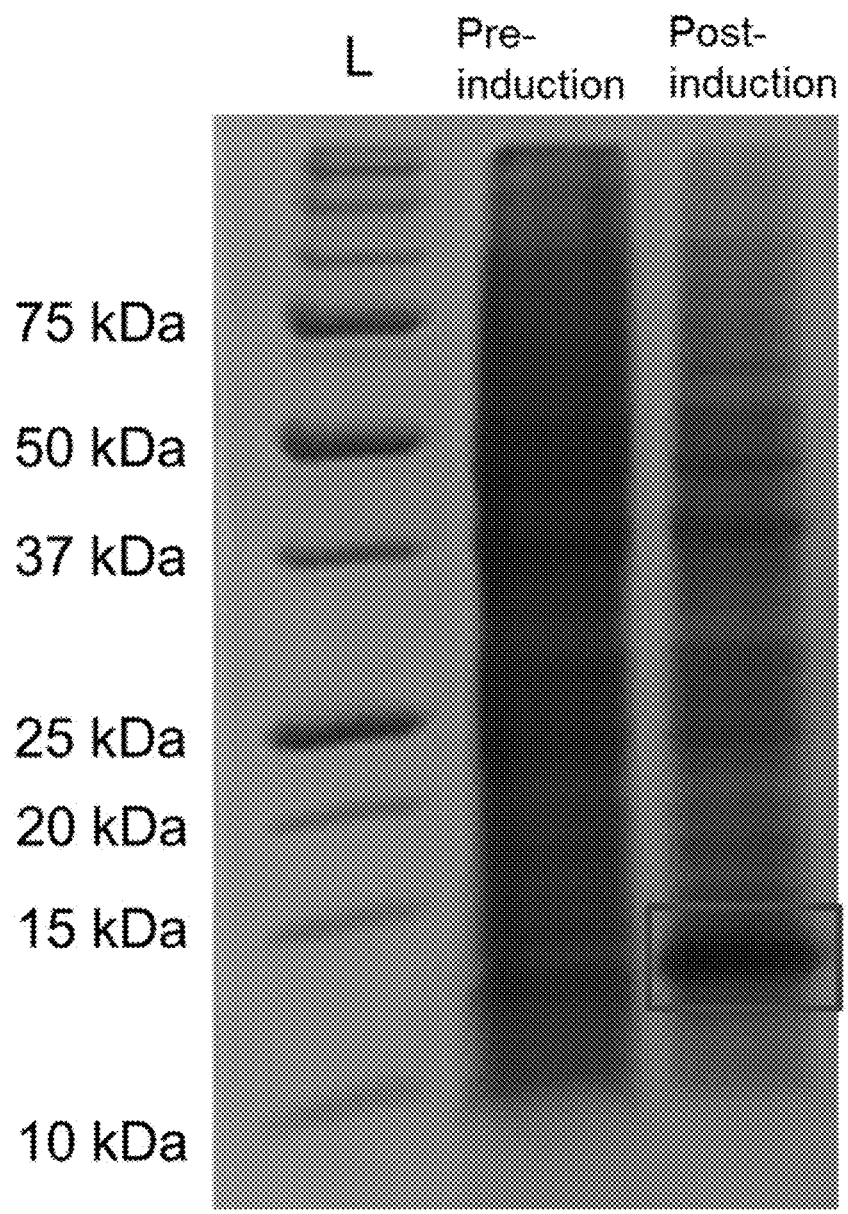
FIG. 7. 12% SDS-PAGE for expression of ACE-MAP. Overexpression observed at expected molecular weight (12.4 kDa) for ACE-MAP post-induction with IPTG. L: protein ladder.

ACE-MAP protein was expressed in phenylalanine auxotrophic AFIQ E. coli cells. pQE30/ACE-MAP plasmid was transformed via heat shock in chemically competent AFIQ cells. Transformed cells were grown for 14-16 hours at 37° C. on tryptic soy agar plates containing 200 μg/mL ampicillin and 35 μg/mL chloramphenicol. A single colony was inoculated in 16 mL supplemented M9 minimal medium (0.5 M $Na_2HPO_4$, 0.22 M $KH_2PO_4$, 0.08 M NaCl, and 0.18 M $NH_4Cl$) containing all 20 natural amino acids (100 μg/mL), ampicillin (200 μg/mL), chloramphenicol (35 μg/mL), vitamin B (35 μg/mL), D-glucose (100 μg/mL), magnesium sulfate (1 mM), calcium chloride (0.1 mM), and trace metals (0.02% v/v) and incubated at 37° C. and 350 rpm for 16 hours. Following, 8 mL of the starter culture was added to 200 mL of supplemented M9 medium and incubated at 37° C. and 350 rpm until the optical density at 600 nm ($OD_{600}$) reached 0.7. Protein expression was induced with 200 μg/mL IPTG and incubated at 37° C. and 350 rpm for 3 hours. After the expression, cells were harvested by centrifugation at 5000×g at 4° C. for 20 minutes in an Avanti J-25 centrifuge (Beckman Coulter) and stored at −20° C. until purification. Expression of ACE-MAP was confirmed via 12% SDS-PAGE (FIG. 7).

Figure 8:
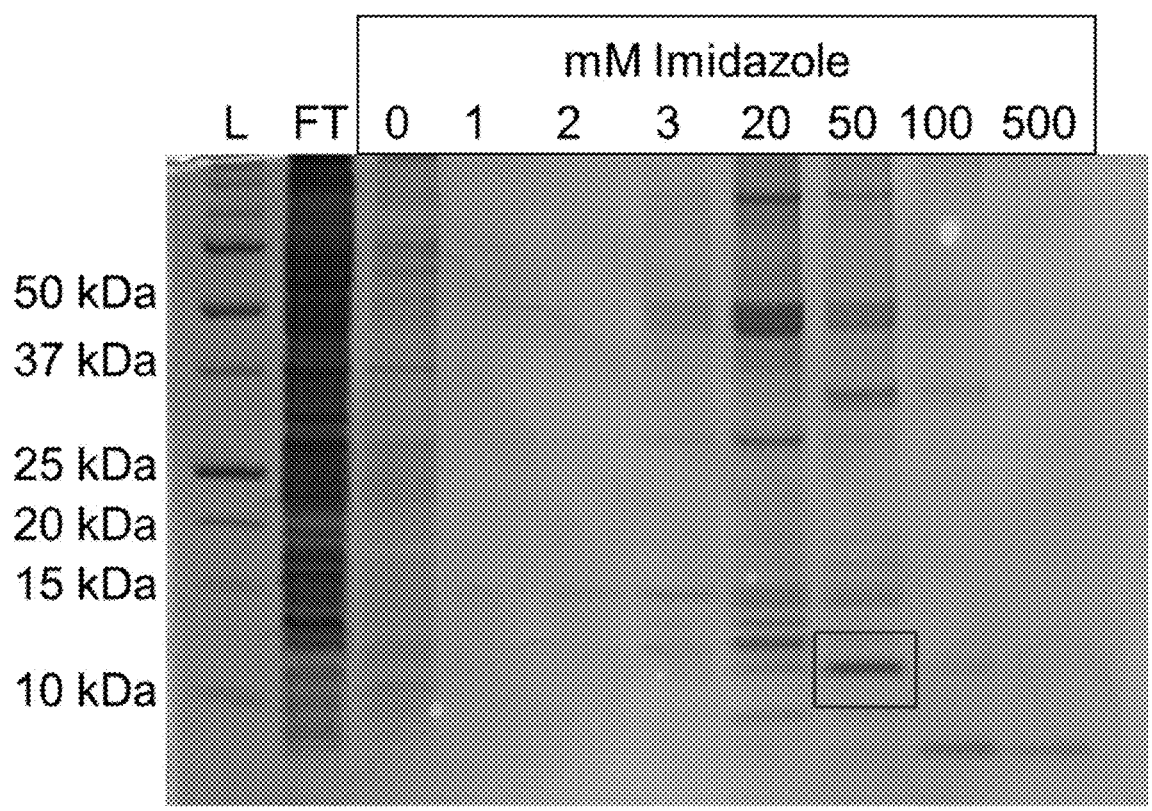
FIG. 8. 12% SDS-PAGE analysis for the purification of ACE-MAP using cobalt-charged IMAC. Different fractions of ACE-MAP were eluted using a concentration gradient of imidazole ranging from 0 M to 50 mM. L: protein ladder, FT: flow through. Protein collected at 10 mM for further purification using SEC column in FPLC.
Figure 9:
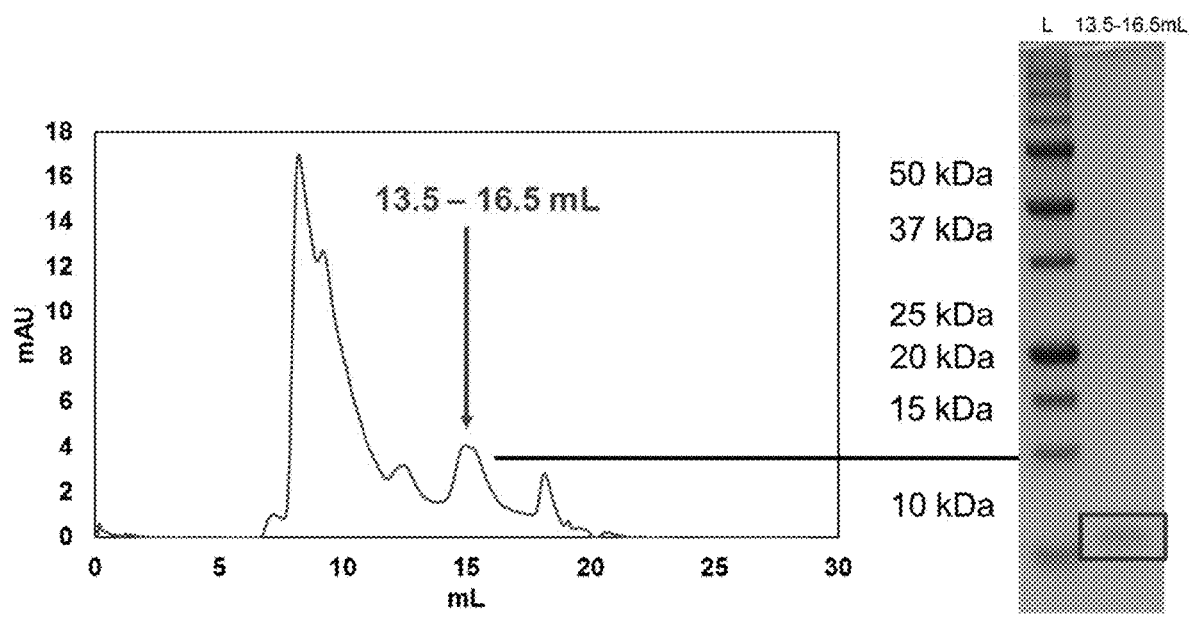
FIG. 9. FPLC chromatograph for purification of ACE-MAP using SEC column and resulting pure fraction shown by SDS-PAGE analysis.

Cell pellets were thawed and resuspended in Buffer A (50 mM Tris HCl, 250 mM NaCl, 6M urea, pH 8.0). Cells were lysed via Q500 probe sonicator (QSonica) at 65% amplitude, pulse on for 5 seconds and off for 30 seconds for a total of 2 minutes. The lysed cells were centrifuged at 11,000×g for 45 min at 4° C. to remove cell debris (Beckman Coulter). The supernatant was removed and purified using a syringe-pump driven IMAC Q Sepharose high performance 5 mL column (HiTrap Q HP 5, GE Health Sciences) charged with $CoCl_2$. Protein was eluted from the column using a gradient (0-100%) of Buffer B (50 mM Tris HCl, 250 mM NaCl, 6 M urea, 500 mM imidazole, pH 8.0) (FIG. 8). Elutions with pure protein were removed and dialyzed using a 3.5 kDa MWCO tubing at 4° C. Dialysis was performed using a step-wise decrease of urea from (three buckets from 3 M to 0.75 M urea) succeeded by six buckets with 0 M urea. The protein elutions were then concentrated to 1.5 mL using 3 kDa MWCO Macrosep and Microsep Advance centrifugal devices (Pall Corporation) at 2,000×g. Following, 500 μL volumes were injected into a Fast Purification Liquid Chromatography (FPLC, AKTA pure, GE Healthcare) using a Superdex 75 10/300 GL Size Exclusion Chromatography (SEC) column (GE Healthcare). Protein was eluted using phosphate buffered saline (PBS) pH 7.4. Pure fractions were determined using a 12% SDS-PAGE (FIG. 8) and protein concentration was determined using a bicinchoninic acid (BCA) assay with a standard curve based on bovine serum albumin concentrations.

The plasmid used for protein expression and purification of SARS-CoV-2 RBD was constructed by insertion of a secretion signal, the coding sequence of a 5A tag, RBD, and a 6×His tag into an expression vector pVRC8400 (kindly provided by the Vaccine Research Center, National institute of Health). The gene construct was codon optimized for mammalian cell expression and synthesized by GenScript. The plasmid was transiently transfected into HEK293S cells for 5 days. Cell supernatants were filtered through 0.22-μm filters, loaded onto Ni-nitrilotriacetic acid (NTA) beads, and proteins were eluted with 600 mM imidazole. The elution was then dialyzed in PBS, flash frozen and stored at −80° C.

Secondary structure of ACE-MAP was measured using the Jasco J-815 CD spectrometer with a PTC-423S single position Peltier temperature control system. Wavelength scans of ACE-MAP (10 μM) were performed from 195 to 250 nm at 1 nm step sizes. Temperature scans were performed from 25° C. to 85° C. at 1° C. step sizes. The mean residue ellipticity (MRE) and melting temperature ($T_m$) were calculated as described in previous studies. The secondary structure content (α-helicity, β-content, and unordered structure) was predicted with CONTIN/LL software.

Addition of 3 mM bis(sulfosuccinimidyl) suberate ($BS^3$) to a 10 μM concentration of ACE-MAP in PBS pH 7.4 was performed for chemical crosslinking to assess oligomerization. The reaction was allowed to incubate at room temperature and 300 rpm for 3 hours in the dark on an Eppendorf Thermomixer C. The reaction was then quenched using 25 mM Tris HCl at pH 7.5 and sampled into a 12% SDS-PAGE and oligomerization was confirmed using Western Blot analysis. To detect and analyze the oligomer bands, Amersham Imager 680 and corresponding analysis software (Cytiva Life Sciences) were used to detect and analyze relative intensities of oligomer bands.

The ELISA protocol was adapted from previously established protocols. A ninety-six well plate was coated overnight at 4° C. with 50 μL per well of a 2 μg/mL solution of SARS-CoV-2 RBD. The next morning, the coating solution was removed and 100 μL per well of 3% non-fat milk prepared in PBS with 0.1% Tween 20 (TPBS) was added to the plate at room temperature (RT) for 2 hours as blocking solution. The blocking solution was removed and 100 μL of serial dilutions of ACE-MAP, C, and ACE2 proteins were added to the plates for 2 hours at RT. The plates were washed three times at 200 μL volumes using 0.1% TPBS. Approximately 100 μL of a 1:3000 anti-Histag horseradish peroxidase (HRP) conjugated secondary antibody (Sino Biological) was prepared in 0.1% TPBS and added to each well for 1 hour. Plates were then washed three times with 200 μL of 1×ELISA wash buffer (Thermo Scientific) and then air dried in a hood. While drying, TMB solution was prepared as described by Sigma Aldrich protocol. 1 mg/mL TMB was prepared in DMSO and then added to 0.05 mM citrate-phosphate buffer with 0.01% hydrogen peroxide (0.01%). Once completely dry, 100 μL of 3,3',5,5'-tetramethylbenzidine (TMB) solution was added to the plates for 10 minutes. To quench the reaction, 50 μL of 3M HCl was added to the plates. Absorbance at OD450 was immediately read using a microplate reader (BioTek Synergy H1).

RAW 264.7 Mouse Macrophage cell line were incubated in DMEM media (Thermofisher). The adherent cells were grown to 70-80% confluence in a flask incubated at 37° C. ACE-MAP was simultaneously subjected to Endotoxin Removal using Pierce High Capacity Endotoxin Removal Spin Columns (Thermofisher). 10,000 cells were then diluted in serial dilutions of ACE-MAP (starting at 500 ng/uL) in 200 μL of DMEM and plated on three 96-well plates. For three days, cells were harvested from each plate at 24, 48, and 72 hour time points and counted using Quant-iT PicoGreen dsDNA Assay Kit (Thermofisher). Mouse IL-6 was detected using Invitrogen IL-6 Mouse ELISA Kit (Thermofisher). Mouse IL-6 concentration was calculated from a Mouse IL-6 standard curve (Thermofisher) and normalized to the control-relative cell count.

Initial structure of C protein was taken from PDBID 3V2P and the 23-residue "binder protein" was taken from residues 21-44 of chain B in PDB 6M17, which was shown to have micromolar affinity to SARS-CoV-2 RBD. In order to fuse the C and binder protein, a series of linker proteins consisting of $[EAAAK]_n$ (SEQ ID NO:176), (n=3, 4, 5) motif were designed computationally using Rosetta (data not shown). Initial monomeric structure of ACE-MAP was made in PyMOL (Schrodinger). Using the symmetry information taken from PDBID 3V2P and Rosetta's symmetric modeling protocol a pentameric structure was produced and relaxed with FastRelax and REF2015 score function. The first five residues in the linker region were manually designed to provide a kink at the junction of C domain and linker, which provided an opening for binding to multiple S-RBDs (FIG. 1). To further improve the chance of ACE-MAP·S-RBD interaction, different lengths of the linker sequence were modeled to ensure that the residues involved in ACE2 binding (Q24, T27, K31, E35, D38, Y41) were on the outer surface of ACE-MAP. A linker sequence with 20 residues (n=4) was chosen that provides adequate length and bend to accommodate multiple S-RBDs.

Figure 2:
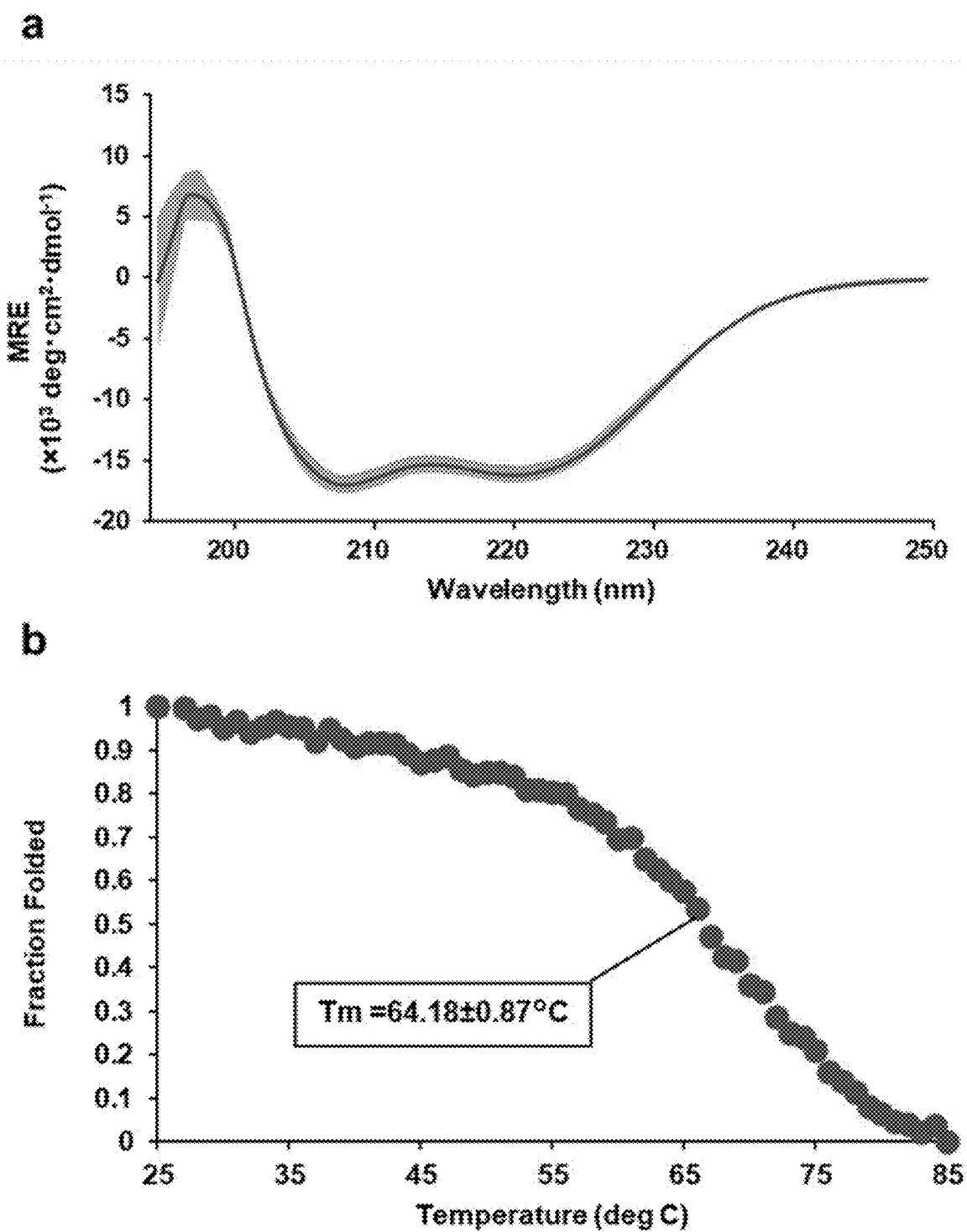
FIG. 2. Circular dichroism of ACE-MAP. a) Wavelength scan of ACE-MAP performed at 25° C. Dark band–average MRE. Light shadow–±standard deviation from average MRE. b) Calculated curve from representative ACE-MAP sample data of relative fraction folded using MRE at 222 nm wavelength from 25° C. to 85° C.

Structural studies of ACE-MAP were performed via circular dichroism spectroscopy. Wavelength scans performed at 25° C. revealed a double-minima of −17,000±700 deg·cm²·dmol⁻¹ 208 nm and −16,000±600 deg·cm²·dmol⁻¹ at 222 nm indicative of helical conformation (FIG. 2a). Analysis via CONTIN illustrated secondary structure of 50.2±2.0% helical content. Relative to the parent C, which was reported to possess 70% helicity, a loss in structure was observed due to the addition of the linker and $ACE_{BINDER}$, which was previously reported with a predicted helicity of 6%. To determine the stability of ACE-MAP, a temperature scan was carried out from 25° C. to 85° C. While the parent C demonstrated a melting temperature of at 60° C., ACE-MAP revealed an increase in stability with a $T_m$ of 64.18±0.87° C., which showed a slight increase in thermostability relative to C (FIG. 2b).

Figure 3:
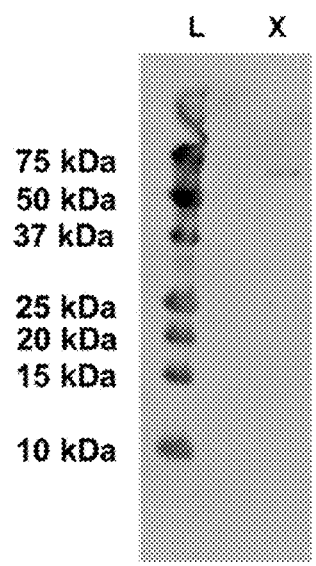
FIG. 3. Western blot from 12% SDS-PAGE of ACE-MAP after $BS^3$ crosslinking (x). Image Analysis reveals intensity is approximately 62.2 kDa molecular weight corresponding to a pentamer self-assembly.

To assess the extent of n-oligomerization due to the coiled-coil domain, BS³ crosslinking of ACE-MAP was employed. After running the sample on a 12% SDS-PAGE, the gel was subjected to western blot analysis and imaged (FIG. 3). Corresponding analysis software was used to quantify the band position and purity revealing a single protein band at approximately 62 kDa indicating n-oligomerization of n=5 (pentamer) only.

Figure 4:
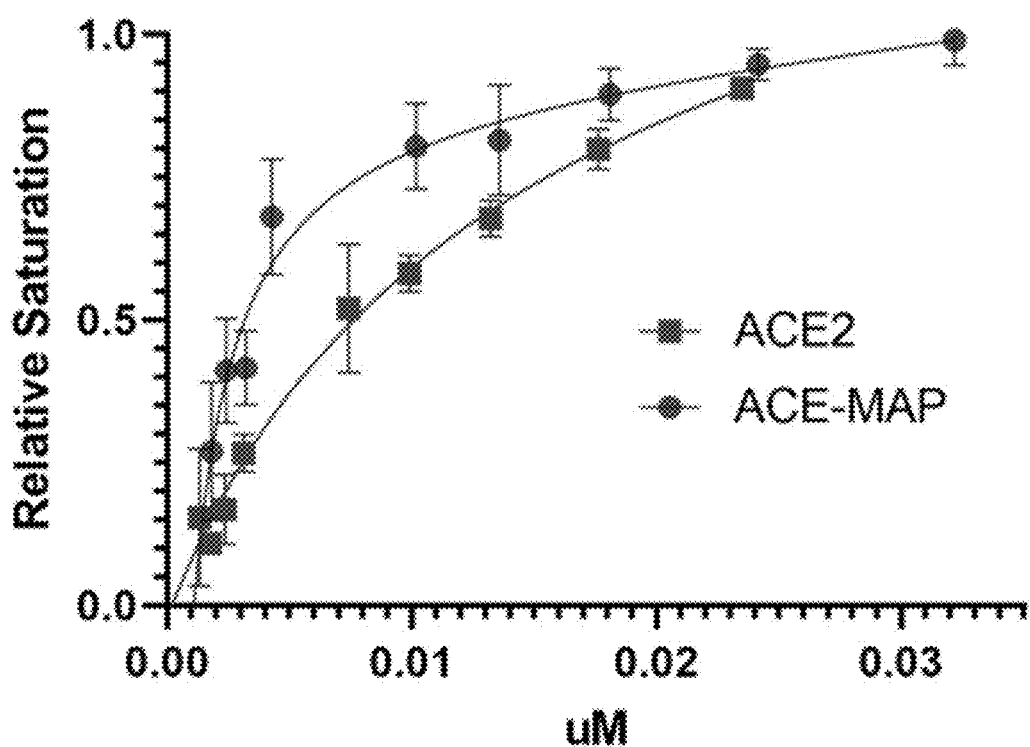
FIG. 4. ELISA fitted with Total Binding Kinetics using Prism 7 (GraphPad) for ACE-MAP vs ACE2 as a function.
Figure 10:
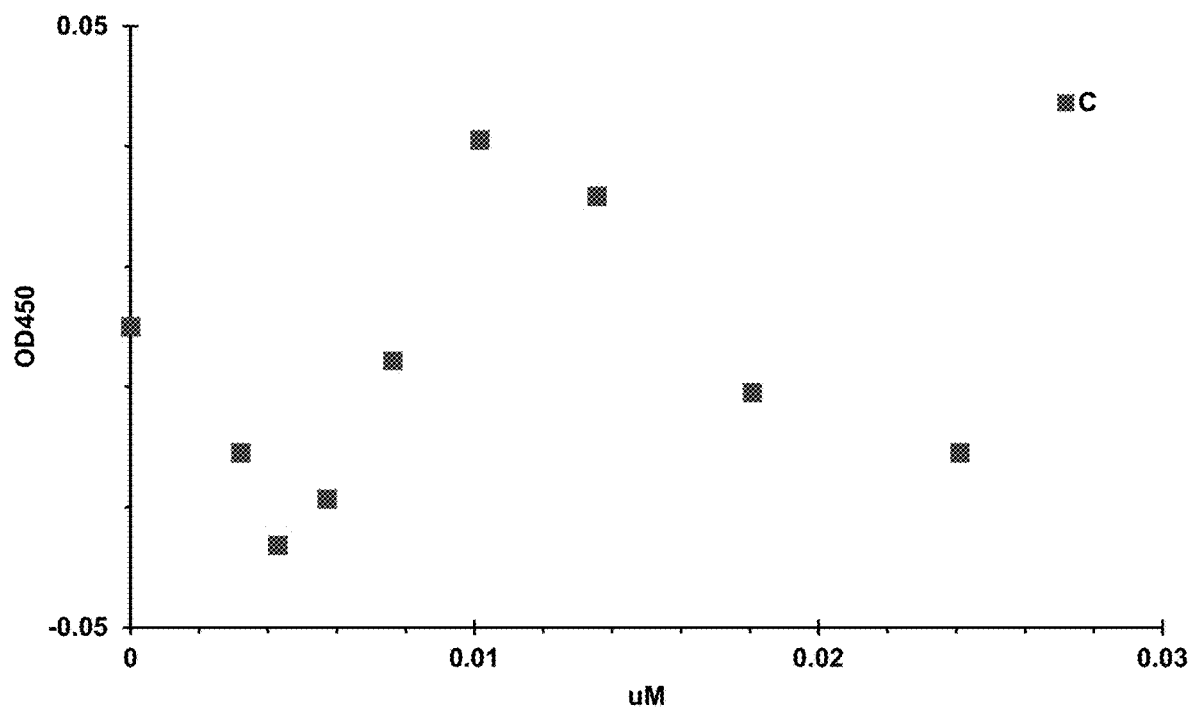
FIG. 10. Representative ELISA data for C against SARS-COV-2 RBD (background subtracted).
Figure 11:
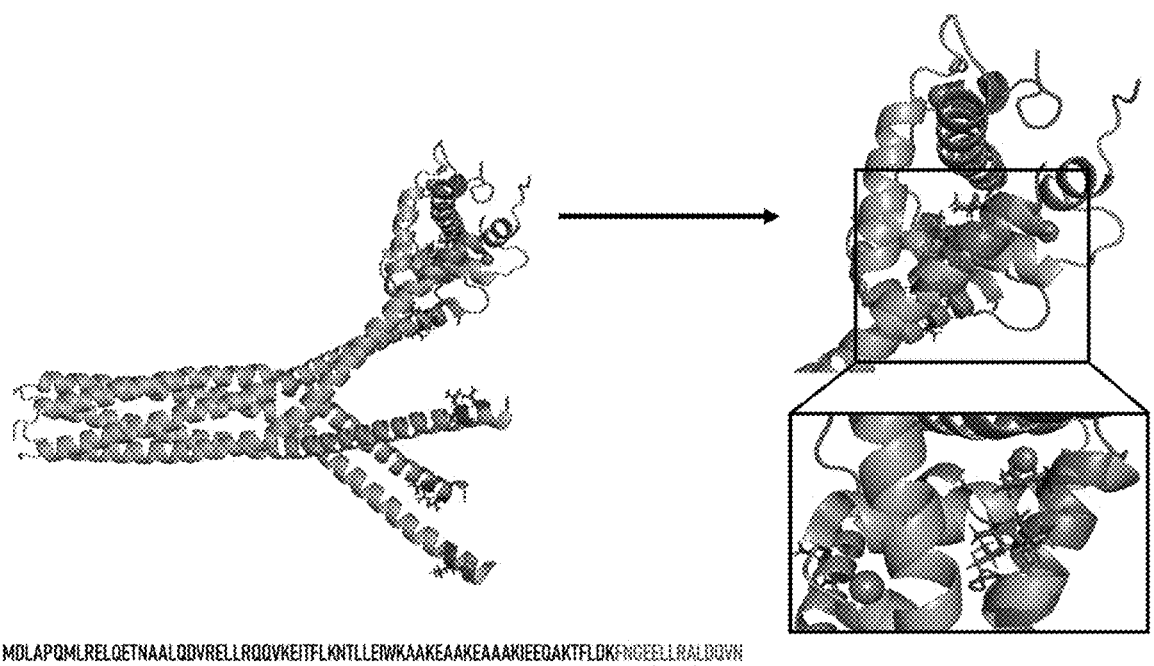
FIG. 11. HIF1α-MAP structure in complex showing HIF1α-MAP and critical binding sites of the HIF1α helical binder (entire region includes IEEQAKTFLDKFNGEELLRALQDVN (SEQ ID NO:1)) shown in complex with its target, CBP/p300. The sequence shown at the bottom is MDLAPQMLRELQETNAALQD VRELLRQQVKEITFL-KNTLLEIWKAAKEAAKEAAAKIEEQAKTFLDKFNG-EELLRAL DQVN (SEQ ID NO: 171).
Figure 12:
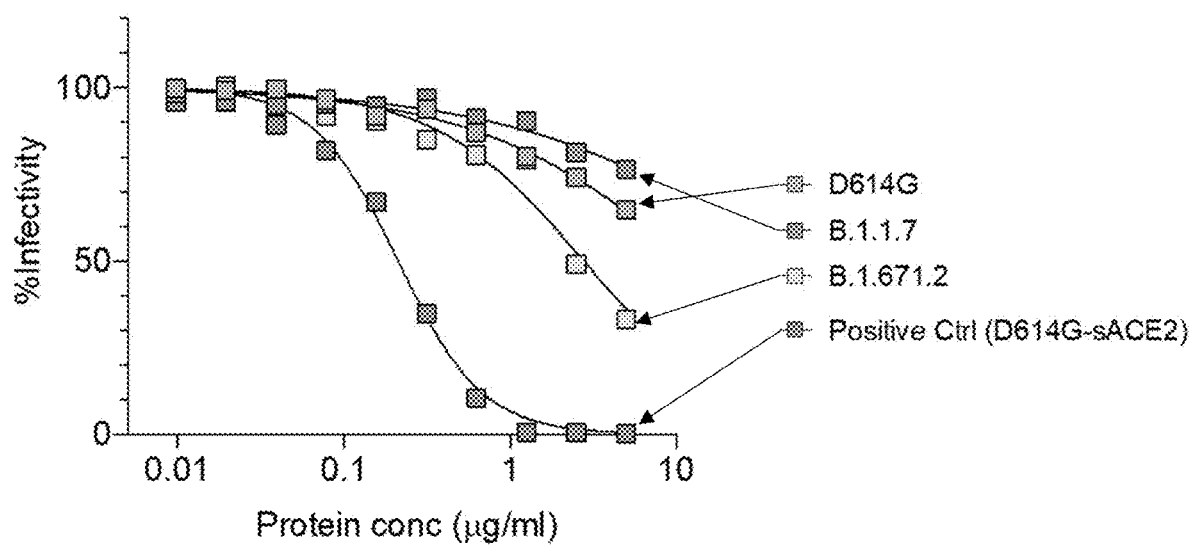
FIG. 12. Neutralization Data of ACE-MAP-1 against SARS-CoV-2 Virus.

The binding affinity of ACE-MAP was tested against SARS-CoV-2 RBD as described previously (FIG. 4). Total binding saturation kinetics were used to determine the maximum saturation ($B_{max}$) and binding affinities ($K_d$) values. ACE-MAP exhibited a $K_d$ of 620 pM. As a negative control, no detectable binding was observed for the parent protein, C (FIG. 10). When compared to full length ACE2 which possessed a $K_d$ of 11.7 nM, ACE-MAP was 19-fold better at binding SARS-CoV-2 RBD. The affinity of ACE-MAP was 620 pM compared to previously designed binders to SARS-CoV-2 RBD ranging from 970 nM to 100 pM. ACE-MAP-2 was similarly tested against SARS-CoV-2 RBD. Total binding saturation kinetics reveal a $K_d$ of 250 pM. When compared to full length ACE2, ACE-MAP-2 is near 50-fold better at binding SARS-CoV-2 RBD.

Figure 5:
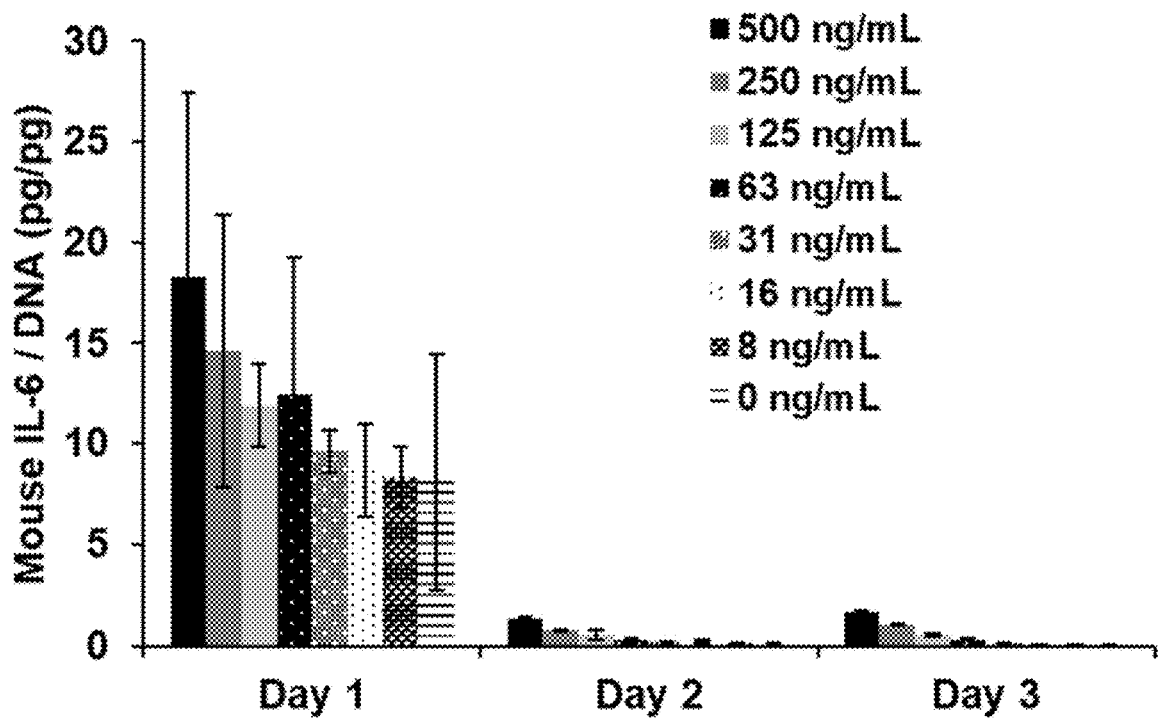
FIG. 5. Mouse IL-6 concentration elicited from Mouse M15MA cells after incubation with ACE-MAP at serial dilutions from 500 ng/mL in DMEM media for 1, 2, and 3 days normalized per DNA concentration.
Figure 6:
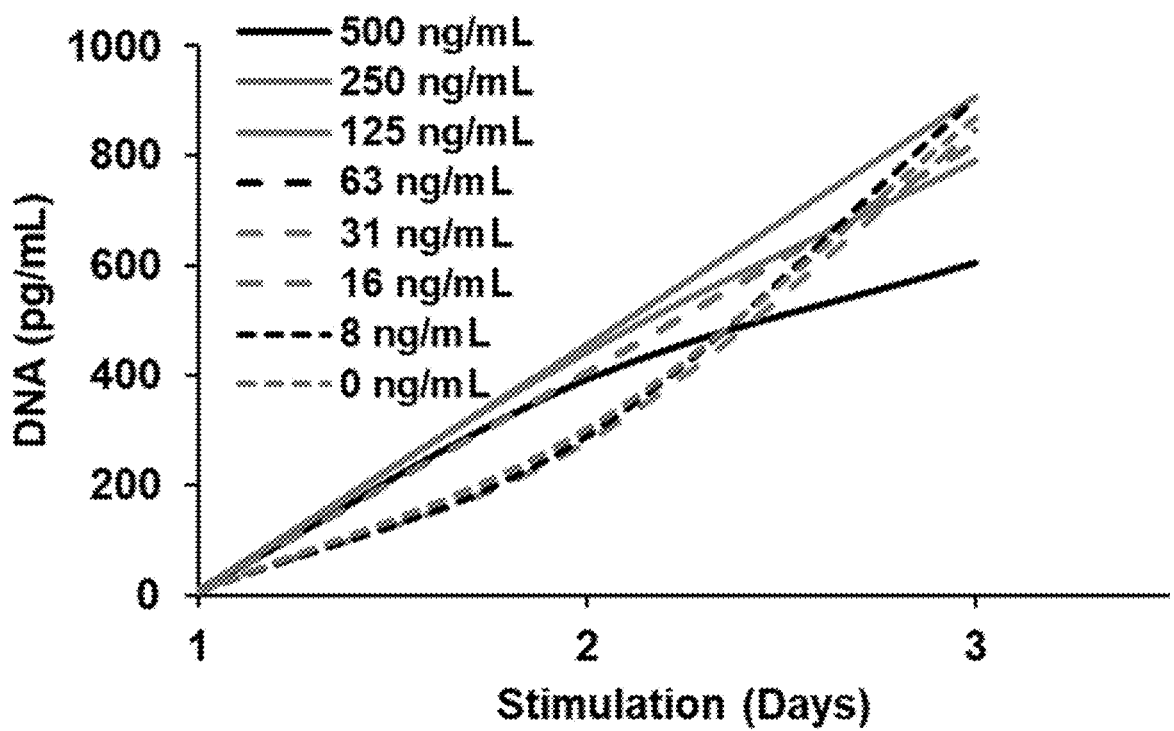
FIG. 6. DNA Concentration measured after Quant-iT PicoGreen dsDNA Assay Kit for 1, 2, and 3 days stimulation with ACE-MAP.

The elicited immune response of ACE-MAP to RAW 264.7 cells were tested for IL-6 concentration each day for three days (FIG. 5) to gauge further therapeutic candidacy. After each day, DNA (pg/mL) was measured using Quant-iT PicoGreen dsDNA Assay Kit (FIG. 6). Mouse IL-6 response at 100 ng/mL and sensitivity limits of ACE-MAP were calculated using the best-fit polynomial and the weighted population standard deviation of its nearest neighbor data points. An unpaired t-test was used to calculate the statistical significance of Mouse IL-6 concentration as compared to the control (0 ng/mL ACE-MAP, RAW 264.7 cells in DMEM).

Typically, overnight to 48-hour incubation of cells after stimulation of the test protein is used to assay early phase cytokine response for immunogenicity and IL-6 has been shown to be a viable analog biomarker for presence of an immune response. ACE-MAP appears to trigger an acute immune response (<20 pg IL-6/pg dsDNA) after one day stimulation of RAW 264.7 cells (FIG. 5) that did not affect cell proliferation in the following days (FIG. 6). While this immune response appeared present, it was not statistically significant at any of the tested ACE-MAP concentrations used to stimulate the cells after one day when compared to the control using an unpaired t-test.

A coiled-coil self-assembled fusion protein capable of binding to SARS-CoV-2 RBD at picomolar affinity is described herein. Its characterization has revealed insights into the utility of multivalent alpha-helical binders for this and future coronavirus variants. Several proteins and antibodies have been recently generated to bind to SARS-CoV-2 RBD. These proteins tend to use either mammalian expression systems and/or be >140 kDa. The protein binders that have been computationally designed to increase the avidity to SARS-CoV-2 based on ACE2 possess $K_d$ values ranging from 970 nM to 100 pM. E. coli expression systems have the unparalleled advantage of low cost, rapid growth, and good productivity; however, it is a host that is out of reach for many recombinant proteins >60 kDa, and especially antibodies, that require post-translational modifications. While ACE-MAP exhibits picomolar binding affinity to SARS-CoV-2 RBD like antibodies, it can be expressed in E. coli and is significantly smaller in size-12 kDa as a monomer (62 kDa as a pentamer). The present approach described herein fundamentally differs from such prior work as the tethering or multivalency is part of the design from the onset.

The present protein ACE-MAP can be used as a non-immunogenic therapeutic. ACE-MAP demonstrates insignificant immune response until Day 3 of incubation at the recommended FDA sensitivity of 100 ng/mL, the lowest concentration at which a therapeutic may be associated with clinical events, with p-values of 0.44, 0.06, and 0.001 for Day 1, Day 2, and Day 3, respectively using an unpaired t-test with the control. This reveals the benefit of using ACE-MAP as a protein therapeutic platform.

Notably, the fusion of $ACE_{BINDER}$ by a kinked linker has resulted in a similarly thermostable protein relative to its C counterpart. In comparison, C with all cysteine residues (C48 and C54) mutated to serines (denoted as $C^{SS}$) reduces the melting temperature of $C^{SS}$ to 45° C. Thus, despite the reduced helical secondary structure, likely due to the kinked region of ACE-MAP reducing the fraction of coiled-coil structure contribution, ACE-MAP maintains a $T_m$ higher than $C^{SS}$ and a $T_m$ more characteristic to wild-type C. Interchain disulfide-bond formation is a property only characteristic of a parallel n=5 oligomer revealing that similarly ACE-MAP is likely to exist in the pentameric coiled-coil conformation. In addition to the pentamerization after BS³ crosslinking, we deduce that the multivalency created by ACE-MAP through oligomerization of the C domain is responsible for the increased binding affinity in comparison to $ACE_{BINDER}$ and ACE2. Also of importance, is that that the strong alpha-helical structure of C may lend itself as a scaffold that stabilizes the $ACE_{BINDER}$ region to become functional against the SARS-CoV-2 RBD. The structural data shown here elucidates this picture well with previous helical content prediction of the $ACE_{BINDER}$ domain noted to be just 6% and optimization of the domain's helicity only creates a modest improvement in binding affinity. The picomolar binding affinity and stability at high temperatures bodes well for future studies into its applications as a stable biosensor or therapeutic.

Using a modified helical binder in ACE-MAP-2 results in improved performance over predecessor ACE-MAP-1 in binding affinity against SARS-CoV-2 RBD. Most significantly the modifications resulted in no change to the biosynthesis process and boasts the interchangeability of the $ACE_{BINDER}$ region to scaffold other binders for SARS-CoV-2 or even other targets such as HIF1α-MAP. Where the ACE-MAP-2 binding domain ($ACE_{BINDER}$) alone shows a 15-fold improvement over ACE2, ACE-MAP-2 results in a 50-fold improvement over ACE2 also signifying the effect of its multivalency in amplifying the ability to bind SARS-CoV-2 RBD.

ACE-MAP was biosynthesized, a small binder protein against SARS-CoV-2 RBD. ACE-MAP may be used as a neutralizing therapeutic or diagnostic protein for immunoassay testing. Fusion of $ACE_{BINDER}$ to C was shown via a computationally designed kinked linker has created a protein with increased thermostability compared to C and increased binding affinity through multivalency compared to just the ACE$_{BINDER}$ region as previously reported. ACE-MAP furthermore shows the utility of generating a PDM utilizing multivalency as the source of high affinity without further design techniques. The increased efficacy of the protein, low immunogenicity, and thermostability at room temperature indicates the utility of simple multivalent fusions. The high avidity of ACE-MAP to SARS-CoV-2 RBD by utilizing its target receptor, ACE2, reveals that ACE-MAP may be useful in a variety of rapid testing applications especially among the growing concern for SARS-CoV-2 mutant escape.

Example 2

The following example provides description of using the proteins of the present disclosure.

FIGS. 13 and 14 provide an example of a design of the present MLFTS. From left to right in the figure indicating the direction of the flow of fluids, are shown: sample pad (which may be termed a sample application zone) on which a biological sample which may comprise an COVID-19 virus or an antibody thereto, are deposited; a conjugation pad (which may be termed a conjugation zone), where the ACE-TAP and the S-TAP probes are allowed to binding to the virus or the antibodies from the sample, a series of test strips comprising virus test, antibody test (which may be different strips for different Igs, such as IgM, IgG, IgA etc.), a control test (collectively, a capture zone), and an absorption pad so the fluid and materials run to the end of the strip. The absorption pad may be considered a wick.

As an example, blood (via finger prick) and/or sputum or spit or tear sample can be directly applied or collected and applied to the sample pad. The capillary force driving the fluids will determine how long it will incubate with the components. In general, it may take 15 minutes to process and detect results. No washing is needed since the flow occurs via capillary force.

Example 3

The following example provides description of using the proteins of the present disclosure.

The PDM requires oxopiperazine functionalization and the binding affinity of the HIF1α OHM provides a 14-fold decrease in its ability to bind to p300. The reduced sensitivity of the PDM to its target is expected for a mimetic. For these reasons, the HIF1α CTAD represents a desirable candidate for incorporation into the MAP design to create HIF1α-MAP. Instead of imbuing structure through a post-expression chemical bond, the MAP is hypothesized to imbue the critical residues with the necessary alpha-helical secondary structure and thus provide it functionality to bind to p300. It was not expected that this strategy would provide an increased binding affinity or capability of reducing tumor volume should it have just been a function of an alpha-helical scaffold in comparison to the OHM PDM strategy. However, in addition to the MAP scaffold being of a multivalent self-assembly, it is hypothesized it would result in an improvement to the binding affinity.

Figure 24:
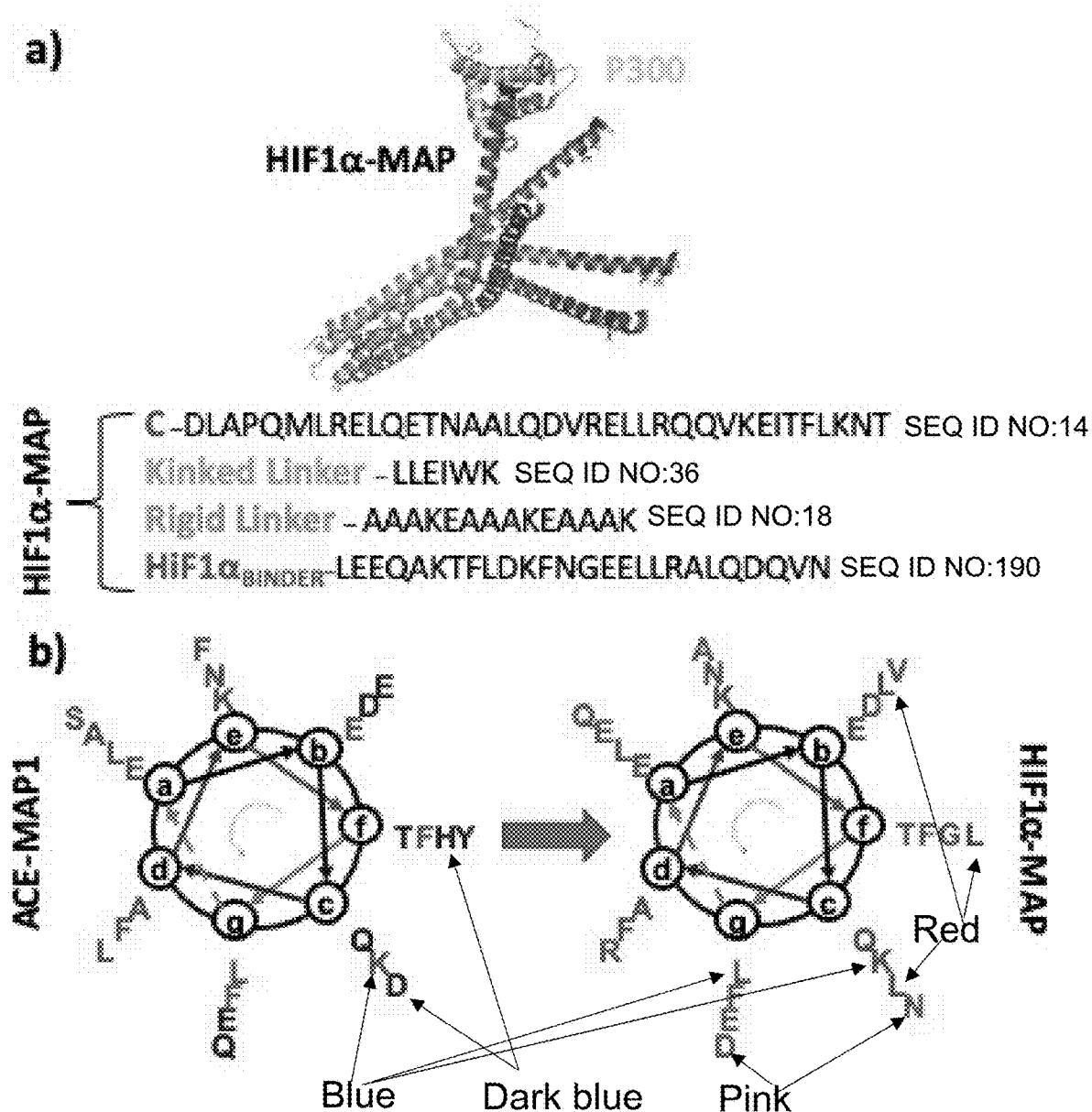
FIG. 24. a) Design of HIF1α-MAP based on ACE-MAP1 where the $ACE_{BINDER}$ and $HIF1α_{BINDER}$ are appended onto the MAP template (C+kinked+rigid linkers). b) Helical wheel diagram comparison of binder regions of HIF1α-MAP and ACE-MAP1, which shows the residues present on each face of the helix. Blue is the ACE-MAP1 sequence (dark blue are critical residues to binding). Pink is HIF1α sequence (all red are the critical residues involved in the interface). Pink and red are not in ACE-MAP1. Dark blue is not in HIFα-MAP.

Described is a scaffold that is inherently multivalent through the self-assembly of helical coiled-coils, which stabilize the helical structure of an immediately fused PPI recognition sequence as a rational approach to PDM stabilization. The multivalency of the protein provides a jump start in the race to increased affinity before undergoing its own evolutionary process, affinity maturation, to become a highly sensitive protein binder to a specific target. In this approach, a coiled-coil domain is used to not only induce α-helicity and structure to present the proper epitope for PPI, but also, it self-assembles into a multivalent pentamer that improves affinity rivaling that of the native protein of which the design is based—a deficit of current PDM strategies. Employing a scaffold based on the coiled-coil domain of cartilage oligomeric matrix protein (C), to the present disclosure provides new fusions or "multivalent assembled protein" (MAP) in which the helix bearing the crucial recognition residues is engineered C-terminal to C (FIG. 24). This new strategy for PDM will benefit from small size, low-cost E. coli expression system in addition to its improved binding. Should the multivalency lead to improved binding affinities and inhibition of a viral competitor, the MAP would act as a potential inexpensive therapeutic. In contrast to most PDMs and therapeutic antibodies, MAPs will also require no post-translational modifications or chemical bonding or crosslinking to stabilize its structure or interface due to its self-assembly. By using a coiled-coil scaffold as a general PDM with the PPI recognition sequence that is fused to the C-terminus, it offers a mix-and-match system of protein binders saving valuable research and development time for a hosts of disease targets including virus and cancer. Most critically, MAPs will provide a basis for α-helical PDM improvement that relies on multivalency and stabilization through direct fusion of PPI recognition sequence in contrast to the distinct and individual research approaches required by previous rationale design methods for PDMs.

Innovation: PDMs have increasingly shown to be desirable candidates for the development of therapeutics that target PPIs. While they can show efficacy in binding their targets, the domains are both designed for a specific target and do not heavily improve on the binding affinity of the native complex. These deficiencies are buoyed by the current approaches to PDM design that include phenotypic or target-based screenings, and structure-based designs such as fragment-based design. These design approaches are inherently restrictive and are tailored for a specific PPI. To emphasize the advantage of facile research and development for PDMs, an emphasis must be made on creating more recyclable design strategies. Thus, the present disclosure provides has several innovations:

- This disclosure offers a ready-to-go pathway towards development of improved α-helical PDMs by a simple multivalent design approach anchored in self-assembly. This creates a broad layout for the development of numerous PDMs with helical interfaces that include the recognition and inhibition of virus binding domains as well as the regulation of factors involved in the proliferation of cancer or wound healing.
- This disclosure creates a relatively small protein capable of PPI mimicry that requires zero post-translational modifications of chemical alterations to stabilize the domain.
- The self-assembly of MAPs produces multivalent scaffolds for its PPI recognition sequence facilitating improved binding affinity over its parent and full-length binding protein. The improvement of a PDM over its native interfacial protein has not yet been overcome from a completely rational and recyclable design method.
- The development of the proposed MAPs has the potential to elucidate the PPIs targeted by assessing the importance of residues and features involved in the interaction through binding affinity assays and structural characterization.

For MAPs that show significant improvement over the binding affinity of its native protein, there will be potential for exploration of the protein as a therapeutic.

Described herein is a new strategy for the design of multivalent assemblies that can stabilize the helical epitope bearing the PPI recognition sequence with affinities that rival or exceed those of the natural protein on which the design was based. While several strategies have been explored as PDMs, all of them focus on the design of a monomeric scaffold that can be later tethered as a dimer or multimer to improve affinities. Although each of these strategies produced molecules that bind proteins, they still are unable to bind with affinities as strong as the natural parent protein.

Figure 23:
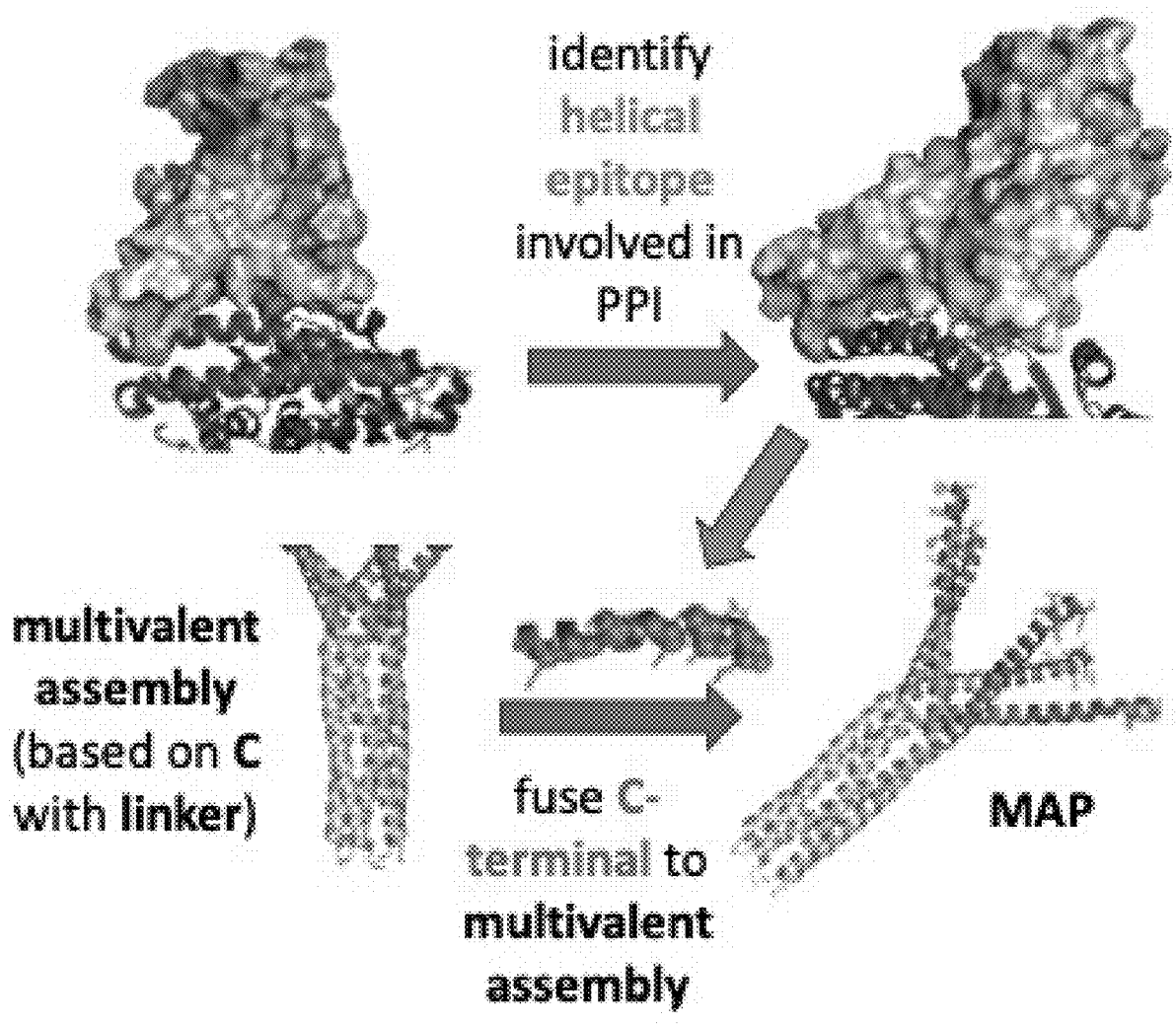
FIG. 23. Multivalent approach for targeting PPIs. Top: identify helical epitope and hotspot residues at the interface and fuse the "PPI recognition sequence" C-terminal to multivalent assembly based on the pentameric coiled-coil C with linker to produce multivalent assembled protein (MAP).

Multivalent Approach for targeting PPIs. The present disclosure differs from other methods. Rather than focusing on designing a monomeric scaffold to target the PPI, multivalency is integrated at the onset of the design where a multimeric coiled-coil is employed to stabilize the helical epitope (FIG. 23). Cartilage oligomeric matrix protein (C) is an α-helical homopentamer, which forms a hydrophobic pore (7.3 nm×0.2-0.6 nm) capable of interacting with a variety of small molecules. C can be engineered to exert specificity for target compounds. Employing C as the scaffold, generate new fusions, termed "multivalent assembled protein" (MAP) in which the PPI recognition sequence is engineered C-terminal to C.

HIF1α has been the subject of recent research in PPIs because of the high percentage of α-helicity at the interface for multiple binding interfaces and when inhibited by helix mimetics, has shown to reduce tumor growth in animal models. Recently, key residues of the C-terminal transactivation (CTAD, aa 786-826) of HIF1α that interact with the cysteine-histidine rich 1 (CH1) domain of the coactivator protein p300 has been mimicked into an effective PDM using the oxopiperazine helix mimetics (OHM) strategy. OHMs employ chemical conjugation of the nitrogen atoms in neighboring backbone amides with an ethylene bridge to create a chiral scaffold to maintain a structure and thus function akin to proteins. This simple design uses just the twelve CTAD residues with a binding affinity of up to 530 nM—as compared to the full length CTAD of HIF1α with a binding affinity of 38 nM by tryptophan fluorescence assay. The OHM PDM significantly reduces HIF activity and down-regulated the expression of hypoxia-inducible genes and in vivo experiments reduces tumor volume by approximately 50%. The use of a PDM is well validated for the HIF1α·p300 complex, however, the PDM requires oxopiperazine functionalization and the binding affinity of the HIF1α OHM provides a 14-fold decrease in its ability to bind to p300. The reduced sensitivity of the PDM to its target is expected for a mimetic, which is inherently reductive from its native inspiration. For these reasons, the HIF1α CTAD represents a desirable candidate for incorporation into the MAP design to create HIF1α-MAP. Instead of imbuing structure through a post-expression chemical bond, the MAP would be expected to inherently imbue the critical residues with the necessary α-helical secondary structure and thus provide it functionality to bind to p300. It was not expected that this strategy would provide an increased binding affinity or capability of reducing tumor volume should it have just been a function of an α-helical scaffold in comparison to the OHM PDM strategy. However, in addition to the MAP scaffold being of a multivalent self-assembly, it is hypothesized an improvement to the binding affinity would occur.

Based on the preliminary data suggesting C and its kinked linker as a conduit for improved binding via multivalency and α-helical scaffolding, a 13-mer α-helical binding domain derived from HIF1α was be grafted to the solvent-exposed residues ACE-MAP to create HIF1α-MAP. Analogs of short α-helices of HIF1α have been shown to bind p300 and inhibit its binding to HIF1α, making the complex not only important for the research of in vivo modulation of hypoxia-inducible signaling but for validation of the MAP assemblies for binding domain flexibility.

To develop a first iteration of HIF1α-MAP, the ACE-MAP1/SARS-CoV-2 RBD scaffold was used as a rational starting pose in PyMOL (FIG. 24a). Hot spot residues of the N-terminal α-helix of ACE to the SARS-CoV-2 RBD were used as an indicator to the solvent exposed and critical positions in the interface possessed by ACE-MAP1. The critical residues of HIF1α were identified to be L141, L142, and L145 (PDB code: 1L8C) in the b, c, and f helical wheel positions of the α-helix making them solvent exposed to the p300 targets (FIG. 24b). Similarly, the b, c, and f positions of the N-terminal α-helix of ACE2 that had the high combination hydrogen bonding with the SARS-CoV-2 RBD was E37, D38, and Y41. Thus, the twelve CTAD HIF1α residues used in the OHM PDM strategy were overlaid onto the contacts that allowed the analogous b, c, and f residues to align which provided the expectation of the highest probability of contact based on the solvent exposure and contacts of ACE-MAP1 (FIG. 24).

Figure 25:
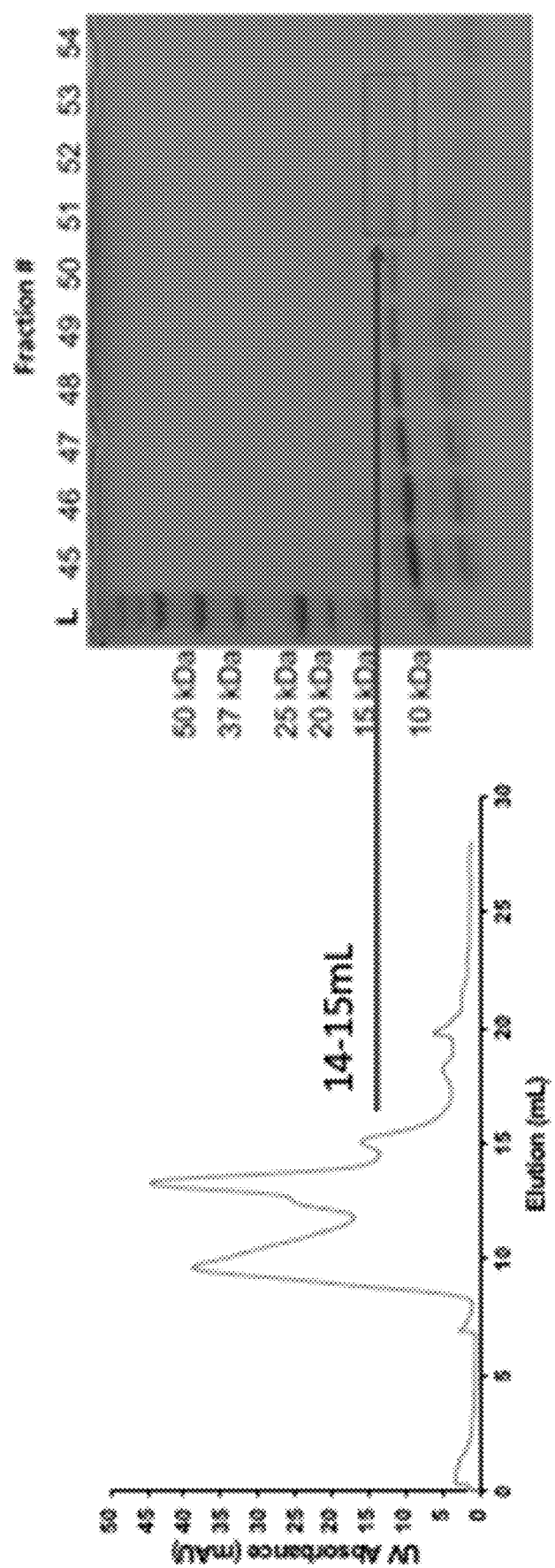
FIG. 25. FPLC chromatograph for purification of HIF1α-MAP1 using SEC column and resulting pure fraction shown by SDS-PAGE analysis.

HIF1α-MAP genetic sequence was constructed and cloned into PQE30. The resulting PQE-HIF1α-MAP1 was expressed in AFIQ E. coli cells. As described in the prior aim, cell pellets were thawed and resuspended in Buffer A and lysed via Q500 probe sonicator. The lysed cells were centrifuged and supernatant purified using a syringe-pump driven IMAC Q Sepharose high performance 5 mL charged with $CoCl_2$. Protein was eluted using the same gradient (0-100%) of Buffer B. Elutions bearing pure protein were removed and dialyzed as before. The elutions will be then purified via SEC column on FPLC and HIF1α-MAP concentration was determined (FIG. 25).

Figure 19:
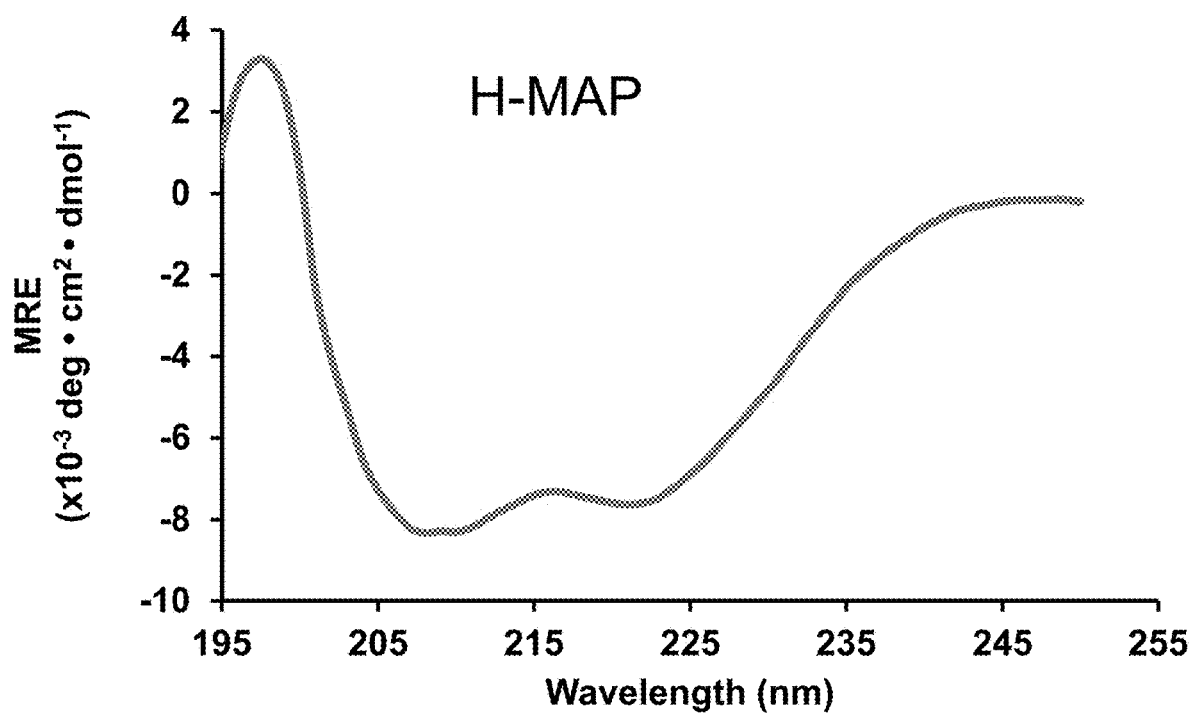
FIG. 19. Circular dichroism wavelength spectrum of HIF1α-MAP (H-MAP).
Figure 20:
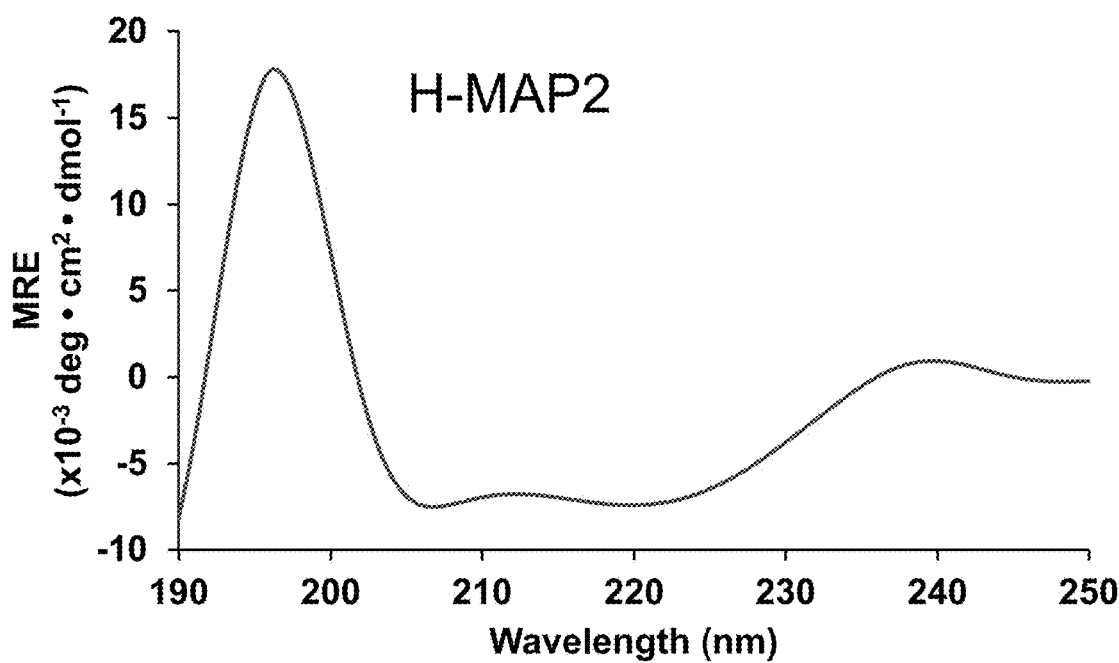
FIG. 20. Circular dichroism wavelength spectrum of H-MAP2 with sequence: MRGSPKKKRKVGGGGSHH-HHHHHHGSACELAATATATATATATAACGD LAPQML-RELQETNAALQDVRELLRQQVKEITFLKNTLLEIWK-AAKEAAKEAAAKIEE QAKTFLDKFNGEELLRALDQ-VN (SEQ ID NO:2).
Figure 21:
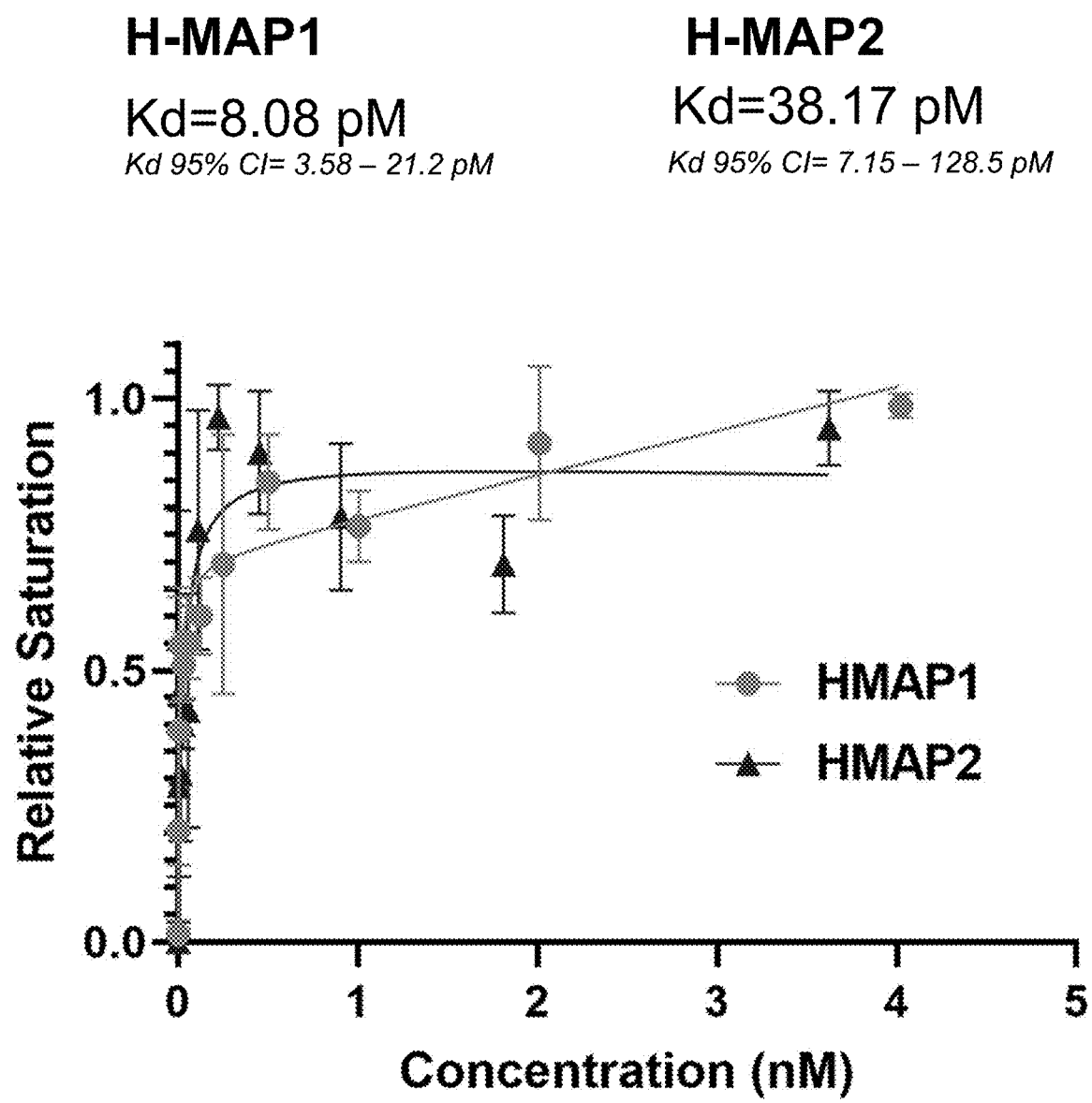
FIG. 21. H-MAP1 (H-MAP) and H-MAP2 ELISA fitted with total binding kinetics using Prism 7 (GraphPad) with calculated binding affinities as an average of three independent trials.
Figure 22:
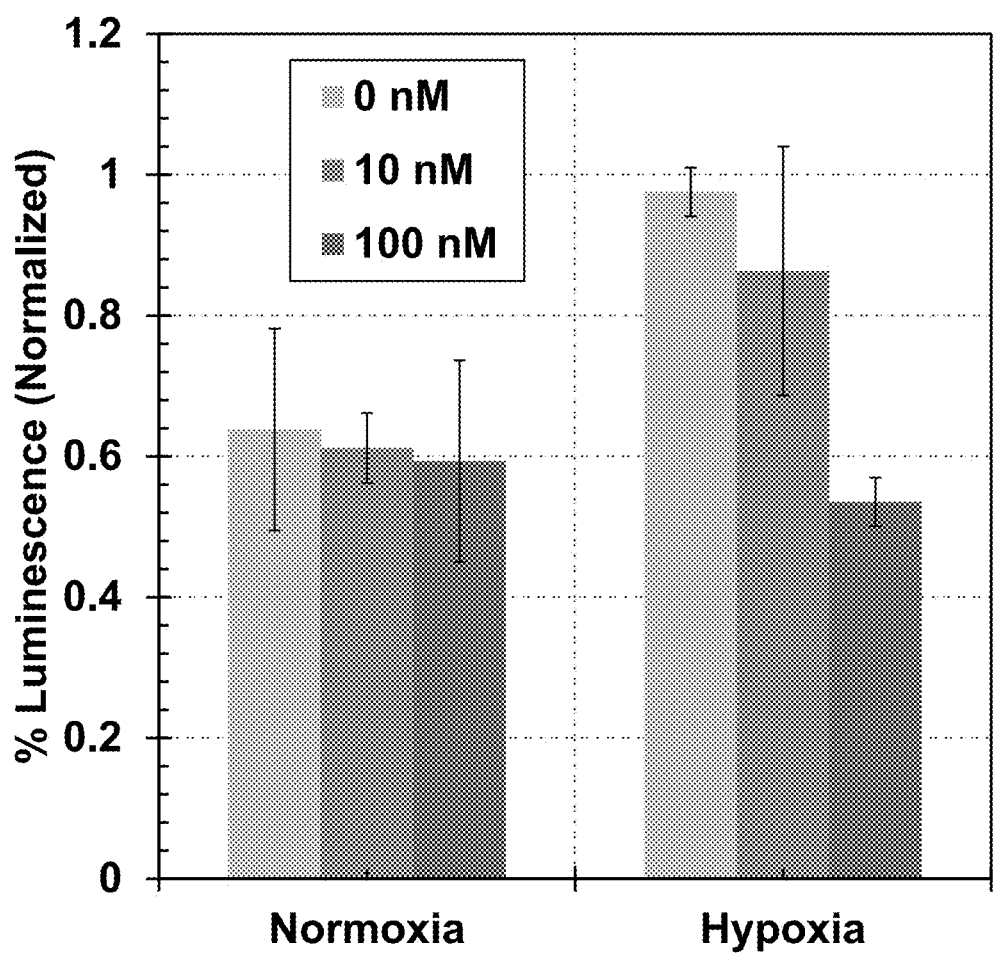
FIG. 22. H-MAP2 added at increasing final concentrations to MDA-MB-231-Luciferase cells in which increasing concentrations show inhibitions of HIF1α in hypoxic conditions induced by a final concentration of 100 μM $CoCl_2$. Results are normalized to maximum luciferase intensity of two independent trials.

Surprisingly, HIF1α-MAP-1 (H-MAP-1) revealed a high affinity with a $K_d$ of 8.08 pM to p300 in comparison to native HIF1α ($K_d$=380 pM) protein with a 47-fold improvement (FIG. 21). CD structural analysis of HIF1α-MAP reveals similarly α-helical protein secondary structure to ACE-MAP1 and ACE-MAP2 indicating that the MAP scaffold provides HIF1α-MAP with proper α-helicity that would be necessary for binding p300 (FIG. 19). Wavelength scans performed at 25° C. revealed a double-minima of −15,000 deg·cm$^2$·dmol$^{-1}$ at 208 nm and −13,000 deg·cm$^2$·dmol$^{-1}$ at 222 nm indicative of α-helical conformation (FIG. 19). Analysis via CONTIN revealed a secondary structure of 49.6% helical content, consistent with the those of ACE-MAP1 and ACE-MAP2. We will further characterize the HIF1α-MAP1 and iterative HIF1α-MAP designs as described in the following section. For example, to increase the likelihood of translocation to the nucleus, HIF1α-MAP-2 (H-MAP-2) was designed by addition of nuclear localization sequence, PKKKRKV (SEQ ID NO:7), at the N-terminus. The addition of the sequences resulting in a slight loss in binding affinity where H-MAP-2 exhibits a $K_d$ of 38.2 pM (FIG. 21) Wavelength scans performed at 25° C. revealed a double-minima of −11,000 deg·cm$^2$·dmol$^{-1}$ at 208 nm and −11,000 deg·cm$^2$·dmol$^{-1}$ at 222 nm indicative of α-helical conformation (FIG. 19). To test the ability of HIF1α-MAPs to modulate hypoxia-inducible signaling, HIF1α-MAP-2 was incubated with triple negative breast cancer cell line, MDA-MB-231, stably transfected a construct to express firefly luciferase under normoxic and hypoxic (induced with final concentration 100 μM $CoCl_2$) conditions. Increasing concentrations of HIF1α-MAP-2 exhibited decreased expression of luciferase after normalizing by protein concentration as measured by BCA assay indicating the ability for HIF1α-MAPs to downregulate hypoxia-inducible gene expression (FIG. 19).

While the present invention has been described through illustrative embodiments, routine modification will be apparent to those skilled in the art and such modifications are intended to be within the scope of this disclosure.

```
                              SEQUENCE LISTING

Sequence total quantity: 190
SEQ ID NO: 1            moltype = AA   length = 25
FEATURE                 Location/Qualifiers
source                  1..25
                        mol_type = protein
                        organism = synthetic construct
SEQUENCE: 1
IEEQAKTFLD KFNGEELLRA LQDVN                                                25

SEQ ID NO: 2            moltype = AA   length = 127
FEATURE                 Location/Qualifiers
source                  1..127
                        mol_type = protein
                        organism = synthetic construct
SEQUENCE: 2
MRGSPKKKRK VGGGGSHHHH HHHHGSACEL AATATATATA TATAACGDLA PQMLRELQET          60
NAALQDVREL LRQQVKEITF LKNTLLEIWK AAKEAAKEAA AKIEEQAKTF LDKFNGEELL         120
RALDQVN                                                                  127

SEQ ID NO: 3            moltype = AA   length = 79
FEATURE                 Location/Qualifiers
source                  1..79
                        mol_type = protein
                        organism = synthetic construct
SEQUENCE: 3
MRGSHHHHHH GSACELAATA TATATATATA ACGDLAPQML RELQETNAAL QDVRELLRQQ          60
VKEITFLKNT LLEIWKAAK                                                       79

SEQ ID NO: 4            moltype = AA   length = 79
FEATURE                 Location/Qualifiers
source                  1..79
                        mol_type = protein
                        organism = synthetic construct
SEQUENCE: 4
MRGSHHHHHH GSASELAATA TATATATATA ASGDLAPQML RELQETNAAL QDVRELLRQQ          60
VKEITFLKNT LLEIWKAAK                                                       79

SEQ ID NO: 5            moltype = AA   length = 76
FEATURE                 Location/Qualifiers
source                  1..76
                        mol_type = protein
                        organism = synthetic construct
SEQUENCE: 5
MRGSHHHHHH GSACELAATA TATATATATA ACGDLAPQML RELQETNAAL QDVRELLRQQ          60
VKEITFLKNT LLEIWK                                                          76

SEQ ID NO: 6            moltype = AA   length = 76
FEATURE                 Location/Qualifiers
source                  1..76
                        mol_type = protein
                        organism = synthetic construct
SEQUENCE: 6
MRGSHHHHHH GSASELAATA TATATATATA ASGDLAPQML RELQETNAAL QDVRELLRQQ          60
VKEITFLKNT LLEIWK                                                          76

SEQ ID NO: 7            moltype = AA   length = 7
FEATURE                 Location/Qualifiers
source                  1..7
                        mol_type = protein
                        organism = synthetic construct
SEQUENCE: 7
PKKKRKV                                                                     7

SEQ ID NO: 8            moltype = AA   length = 69
FEATURE                 Location/Qualifiers
source                  1..69
                        mol_type = protein
                        organism = synthetic construct
SEQUENCE: 8
GSACELAATA TATATATATA ACGDLAPQML RELQETNAAL QDVRELLRQQ VKEITFLKNT          60
```

```
                                          -continued

LLEIWKAAK                                                                   69

SEQ ID NO: 9           moltype = AA  length = 69
FEATURE                Location/Qualifiers
source                 1..69
                       mol_type = protein
                       organism = synthetic construct
SEQUENCE: 9
GSASELAATA TATATATATA ASGDLAPQML RELQETNAAL QDVRELLRQQ VKEITFLKNT    60
LLEIWKAAK                                                           69

SEQ ID NO: 10          moltype = AA  length = 66
FEATURE                Location/Qualifiers
source                 1..66
                       mol_type = protein
                       organism = synthetic construct
SEQUENCE: 10
GSACELAATA TATATATATA ACGDLAPQML RELQETNAAL QDVRELLRQQ VKEITFLKNT    60
LLEIWK                                                              66

SEQ ID NO: 11          moltype = AA  length = 66
FEATURE                Location/Qualifiers
source                 1..66
                       mol_type = protein
                       organism = synthetic construct
SEQUENCE: 11
GSASELAATA TATATATATA ASGDLAPQML RELQETNAAL QDVRELLRQQ VKEITFLKNT    60
LLEIWK                                                              66

SEQ ID NO: 12          moltype = AA  length = 46
FEATURE                Location/Qualifiers
source                 1..46
                       mol_type = protein
                       organism = synthetic construct
SEQUENCE: 12
DLAPQMLREL QETNAALQDV RELLRQQVKE ITFLKNTLLE IWKAAK                   46

SEQ ID NO: 13          moltype = AA  length = 43
FEATURE                Location/Qualifiers
source                 1..43
                       mol_type = protein
                       organism = synthetic construct
SEQUENCE: 13
DLAPQMLREL QETNAALQDV RELLRQQVKE ITFLKNTLLE IWK                      43

SEQ ID NO: 14          moltype = AA  length = 37
FEATURE                Location/Qualifiers
source                 1..37
                       mol_type = protein
                       organism = synthetic construct
SEQUENCE: 14
DLAPQMLREL QETNAALQDV RELLRQQVKE ITFLKNT                             37

SEQ ID NO: 15          moltype = AA  length = 93
FEATURE                Location/Qualifiers
source                 1..93
                       mol_type = protein
                       organism = synthetic construct
SEQUENCE: 15
MRGSPKKKRK VGGGGSHHHH HHHHGSACEL AATATATATA TAAACGDLA PQMLRELQET    60
NAALQDVREL LRQQVKEITF LKNTLLEIWK AAK                                 93

SEQ ID NO: 16          moltype = AA  length = 93
FEATURE                Location/Qualifiers
source                 1..93
                       mol_type = protein
                       organism = synthetic construct
SEQUENCE: 16
MRGSPKKKRK VGGGGSHHHH HHHHGSASEL AATATATATA TAASGDLA PQMLRELQET     60
NAALQDVREL LRQQVKEITF LKNTLLEIWK AAK                                 93

SEQ ID NO: 17          moltype = AA  length = 90
FEATURE                Location/Qualifiers
source                 1..90
                       mol_type = protein
                       organism = synthetic construct
SEQUENCE: 17
MRGSPKKKRK VGGGGSHHHH HHHHGSACEL AATATATATA TAAACGDLA PQMLRELQET    60
NAALQDVREL LRQQVKEITF LKNTLLEIWK                                     90
```

```
SEQ ID NO: 18            moltype = AA  length = 90
FEATURE                  Location/Qualifiers
source                   1..90
                         mol_type = protein
                         organism = synthetic construct
SEQUENCE: 18
MRGSPKKKRK VGGGGSHHHH HHHHGSASEL AATATATATA TATAASGDLA PQMLRELQET   60
NAALQDVREL LRQQVKEITF LKNTLLEIWK                                    90

SEQ ID NO: 19            moltype = AA  length = 70
FEATURE                  Location/Qualifiers
source                   1..70
                         mol_type = protein
                         organism = synthetic construct
SEQUENCE: 19
MRGSPKKKRK VGGGGSHHHH HHHHDLAPQM LRELQETNAA LQDVRELLRQ QVKEITFLKN   60
TLLEIWKAAK                                                          70

SEQ ID NO: 20            moltype = AA  length = 67
FEATURE                  Location/Qualifiers
source                   1..67
                         mol_type = protein
                         organism = synthetic construct
SEQUENCE: 20
MRGSPKKKRK VGGGGSHHHH HHHHDLAPQM LRELQETNAA LQDVRELLRQ QVKEITFLKN   60
TLLEIWK                                                             67

SEQ ID NO: 21            moltype = AA  length = 61
FEATURE                  Location/Qualifiers
source                   1..61
                         mol_type = protein
                         organism = synthetic construct
SEQUENCE: 21
MRGSPKKKRK VGGGGSHHHH HHHHDLAPQM LRELQETNAA LQDVRELLRQ QVKEITFLKN   60
T                                                                   61

SEQ ID NO: 22            moltype = AA  length = 5
FEATURE                  Location/Qualifiers
source                   1..5
                         mol_type = protein
                         organism = synthetic construct
REGION                   5
                         note = The entire sequence can be repeated 1 to 50 times.
SEQUENCE: 22
GGGGS                                                               5

SEQ ID NO: 23            moltype = AA  length = 4
FEATURE                  Location/Qualifiers
source                   1..4
                         mol_type = protein
                         organism = synthetic construct
REGION                   4
                         note = The entire sequence may be repeated 1 to 50 times
SEQUENCE: 23
EAAK                                                                4

SEQ ID NO: 24            moltype = AA  length = 5
FEATURE                  Location/Qualifiers
source                   1..5
                         mol_type = protein
                         organism = synthetic construct
REGION                   5
                         note = The entire sequence may be repeated 1 to 50 times
SEQUENCE: 24
PAPAP                                                               5

SEQ ID NO: 25            moltype = AA  length = 46
FEATURE                  Location/Qualifiers
source                   1..46
                         mol_type = protein
                         organism = synthetic construct
SEQUENCE: 25
AEAAAKEAAA KEAAAKEAAA KALEAEAAAK EAAAKEAAAK EAAAKA                  46

SEQ ID NO: 26            moltype = AA  length = 12
FEATURE                  Location/Qualifiers
source                   1..12
                         mol_type = protein
```

-continued

```
SEQUENCE: 26
AEAAAKEAAA KA                                                            12

SEQ ID NO: 27         moltype = AA  length = 17
FEATURE               Location/Qualifiers
source                1..17
                      mol_type = protein
                      organism = synthetic construct
SEQUENCE: 27
VSQTSKLTRA ETVFPDV                                                       17

SEQ ID NO: 28         moltype = AA  length = 6
FEATURE               Location/Qualifiers
source                1..6
                      mol_type = protein
                      organism = synthetic construct
SEQUENCE: 28
PLGLWA                                                                    6

SEQ ID NO: 29         moltype = AA  length = 6
FEATURE               Location/Qualifiers
source                1..6
                      mol_type = protein
                      organism = synthetic construct
SEQUENCE: 29
RVLAEA                                                                    6

SEQ ID NO: 30         moltype = AA  length = 10
FEATURE               Location/Qualifiers
source                1..10
                      mol_type = protein
                      organism = synthetic construct
SEQUENCE: 30
EDVVCCSMSY                                                               10

SEQ ID NO: 31         moltype = AA  length = 8
FEATURE               Location/Qualifiers
source                1..8
                      mol_type = protein
                      organism = synthetic construct
SEQUENCE: 31
GGIEGRGS                                                                  8

SEQ ID NO: 32         moltype = AA  length = 10
FEATURE               Location/Qualifiers
source                1..10
                      mol_type = protein
                      organism = synthetic construct
SEQUENCE: 32
TRHRQPRGWE                                                               10

SEQ ID NO: 33         moltype = AA  length = 10
FEATURE               Location/Qualifiers
source                1..10
                      mol_type = protein
                      organism = synthetic construct
SEQUENCE: 33
AGNRVRRSVG                                                               10

SEQ ID NO: 34         moltype = AA  length = 9
FEATURE               Location/Qualifiers
source                1..9
                      mol_type = protein
                      organism = synthetic construct
SEQUENCE: 34
RRRRRRRRR                                                                 9

SEQ ID NO: 35         moltype = AA  length = 4
FEATURE               Location/Qualifiers
source                1..4
                      mol_type = protein
                      organism = synthetic construct
SEQUENCE: 35
GFLG                                                                      4

SEQ ID NO: 36         moltype = AA  length = 6
FEATURE               Location/Qualifiers
source                1..6
```

```
                        mol_type = protein
                        organism = synthetic construct
SEQUENCE: 36
LLEIWK                                                                      6

SEQ ID NO: 37           moltype = AA   length = 23
FEATURE                 Location/Qualifiers
source                  1..23
                        mol_type = protein
                        organism = synthetic construct
SEQUENCE: 37
IEEQAKTFLD KFNHEAEDLF YQS                                                  23

SEQ ID NO: 38           moltype = AA   length = 23
FEATURE                 Location/Qualifiers
source                  1..23
                        mol_type = protein
                        organism = synthetic construct
SEQUENCE: 38
LEEQYKTFLD KFMHELEDLL YQL                                                  23

SEQ ID NO: 39           moltype = AA   length = 25
FEATURE                 Location/Qualifiers
source                  1..25
                        mol_type = protein
                        organism = synthetic construct
SEQUENCE: 39
IEEQAKTFLD KFNGEELLRA LDQVN                                                25

SEQ ID NO: 40           moltype = AA   length = 113
FEATURE                 Location/Qualifiers
source                  1..113
                        mol_type = protein
                        organism = synthetic construct
SEQUENCE: 40
MRGSHHHHHH GSACELAATA TATATATATA ACGDLAPQML RELQETNAAL QDVRELLRQQ          60
VKEITFLKNT LLEIWKAAAK EAAAKEAAAK IEEQAKTFLD KFNHEAEDLF YQS                113

SEQ ID NO: 41           moltype = AA   length = 113
FEATURE                 Location/Qualifiers
source                  1..113
                        mol_type = protein
                        organism = synthetic construct
SEQUENCE: 41
MRGSHHHHHH GSASELAATA TATATATATA ASGDLAPQML RELQETNAAL QDVRELLRQQ          60
VKEITFLKNT LLEIWKAAAK EAAAKEAAAK IEEQAKTFLD KFNHEAEDLF YQS                113

SEQ ID NO: 42           moltype = AA   length = 108
FEATURE                 Location/Qualifiers
source                  1..108
                        mol_type = protein
                        organism = synthetic construct
REGION                  81..85
                        note = The sequence of residues 81 to 85 can be repeated 1
                        to 50 times
SEQUENCE: 42
MRGSHHHHHH GSACELAATA TATATATATA ACGDLAPQML RELQETNAAL QDVRELLRQQ          60
VKEITFLKNT LLEIWKAAAK EAAAKIEEQA KTFLDKFNHE AEDLFYQS                      108

SEQ ID NO: 43           moltype = AA   length = 108
FEATURE                 Location/Qualifiers
source                  1..108
                        mol_type = protein
                        organism = synthetic construct
REGION                  81..85
                        note = The sequence of residues 81 to 85 may be repeated 1
                        to 50 times
SEQUENCE: 43
MRGSHHHHHH GSASELAATA TATATATATA ASGDLAPQML RELQETNAAL QDVRELLRQQ          60
VKEITFLKNT LLEIWKAAAK EAAAKIEEQA KTFLDKFNHE AEDLFYQS                      108

SEQ ID NO: 44           moltype = AA   length = 108
FEATURE                 Location/Qualifiers
source                  1..108
                        mol_type = protein
                        organism = synthetic construct
REGION                  81..85
                        note = The sequence of residues 81 to 85 may be repeated 1
                        to 50 times
```

```
SEQUENCE: 44
MRGSHHHHHH GSACELAATA TATATATATA ACGDLAPQML RELQETNAAL QDVRELLRQQ    60
VKEITFLKNT LLEIWKAAAK PAPAPIEEQA KTFLDKFNHE AEDLFYQS               108

SEQ ID NO: 45           moltype = AA   length = 108
FEATURE                 Location/Qualifiers
source                  1..108
                        mol_type = protein
                        organism = synthetic construct
REGION                  81..85
                        note = The sequence of residues 81 to 85 may be repeated 1
                        to 50 times
SEQUENCE: 45
MRGSHHHHHH GSASELAATA TATATATATA ASGDLAPQML RELQETNAAL QDVRELLRQQ    60
VKEITFLKNT LLEIWKAAAK PAPAPIEEQA KTFLDKFNHE AEDLFYQS               108

SEQ ID NO: 46           moltype = AA   length = 108
FEATURE                 Location/Qualifiers
source                  1..108
                        mol_type = protein
                        organism = synthetic construct
REGION                  81..85
                        note = The sequence of residues 81 to 85 may be repeated 1
                        to 50 times
SEQUENCE: 46
MRGSHHHHHH GSACELAATA TATATATATA ACGDLAPQML RELQETNAAL QDVRELLRQQ    60
VKEITFLKNT LLEIWKAAAK GGGGSIEEQA KTFLDKFNHE AEDLFYQS               108

SEQ ID NO: 47           moltype = AA   length = 108
FEATURE                 Location/Qualifiers
source                  1..108
                        mol_type = protein
                        organism = synthetic construct
REGION                  81..85
                        note = The sequence of residues 81 to 85 may be repeated 1
                        to 50 times
SEQUENCE: 47
MRGSHHHHHH GSASELAATA TATATATATA ASGDLAPQML RELQETNAAL QDVRELLRQQ    60
VKEITFLKNT LLEIWKAAAK GGGGSIEEQA KTFLDKFNHE AEDLFYQS               108

SEQ ID NO: 48           moltype = AA   length = 105
FEATURE                 Location/Qualifiers
source                  1..105
                        mol_type = protein
                        organism = synthetic construct
REGION                  81..82
                        note = The sequence of residues 81 to 82 may be repeated 1
                        to 50 times
SEQUENCE: 48
MRGSHHHHHH GSACELAATA TATATATATA ACGDLAPQML RELQETNAAL QDVRELLRQQ    60
VKEITFLKNT LLEIWKAAAK ATIEEQAKTF LDKFNHEAED LFYQS                  105

SEQ ID NO: 49           moltype = AA   length = 105
FEATURE                 Location/Qualifiers
source                  1..105
                        mol_type = protein
                        organism = synthetic construct
REGION                  81..82
                        note = The sequence of residues 81 to 82 may be repeated 1
                        to 50 times
SEQUENCE: 49
MRGSHHHHHH GSASELAATA TATATATATA ASGDLAPQML RELQETNAAL QDVRELLRQQ    60
VKEITFLKNT LLEIWKAAAK ATIEEQAKTF LDKFNHEAED LFYQS                  105

SEQ ID NO: 50           moltype = AA   length = 111
FEATURE                 Location/Qualifiers
source                  1..111
                        mol_type = protein
                        organism = synthetic construct
SEQUENCE: 50
MRGSHHHHHH GSACELAATA TATATATATA ACGDLAPQML RELQETNAAL QDVRELLRQQ    60
VKEITFLKNT LLEIWKAAKE AAKEAAAKLE EQYKTFLDKF MHELEDLLYQ L           111

SEQ ID NO: 51           moltype = AA   length = 111
FEATURE                 Location/Qualifiers
source                  1..111
                        mol_type = protein
                        organism = synthetic construct
SEQUENCE: 51
```

```
MRGSHHHHHH GSASELAATA TATATATATA ASGDLAPQML RELQETNAAL QDVRELLRQQ    60
VKEITFLKNT LLEIWKAAKE AAKEAAAKLE EQYKTFLDKF MHELEDLLYQ L            111

SEQ ID NO: 52           moltype = AA  length = 107
FEATURE                 Location/Qualifiers
source                  1..107
                        mol_type = protein
                        organism = synthetic construct
REGION                  80..84
                        note = The sequence of residues 80 to 84 can be repeated 1
                        to 50 times
SEQUENCE: 52
MRGSHHHHHH GSACELAATA TATATATATA ACGDLAPQML RELQETNAAL QDVRELLRQQ    60
VKEITFLKNT LLEIWKAAKE AAAKLEEQYK TFLDKFMHEL EDLLYQL                 107

SEQ ID NO: 53           moltype = AA  length = 107
FEATURE                 Location/Qualifiers
source                  1..107
                        mol_type = protein
                        organism = synthetic construct
REGION                  80..84
                        note = The sequence of residues 80 to 84 can be repeated 1
                        to 50 times
SEQUENCE: 53
MRGSHHHHHH GSASELAATA TATATATATA ASGDLAPQML RELQETNAAL QDVRELLRQQ    60
VKEITFLKNT LLEIWKAAKE AAAKLEEQYK TFLDKFMHEL EDLLYQL                 107

SEQ ID NO: 54           moltype = AA  length = 107
FEATURE                 Location/Qualifiers
source                  1..107
                        mol_type = protein
                        organism = synthetic construct
REGION                  80..84
                        note = The sequence of residues 80 to 84 can be repeated 1
                        to 50 times
SEQUENCE: 54
MRGSHHHHHH GSACELAATA TATATATATA ACGDLAPQML RELQETNAAL QDVRELLRQQ    60
VKEITFLKNT LLEIWKAAKP APAPLEEQYK TFLDKFMHEL EDLLYQL                 107

SEQ ID NO: 55           moltype = AA  length = 107
FEATURE                 Location/Qualifiers
source                  1..107
                        mol_type = protein
                        organism = synthetic construct
REGION                  80..84
                        note = The sequence of residues 80 to 84 can be repeated 1
                        to 50 times
SEQUENCE: 55
MRGSHHHHHH GSASELAATA TATATATATA ASGDLAPQML RELQETNAAL QDVRELLRQQ    60
VKEITFLKNT LLEIWKAAKP APAPLEEQYK TFLDKFMHEL EDLLYQL                 107

SEQ ID NO: 56           moltype = AA  length = 107
FEATURE                 Location/Qualifiers
source                  1..107
                        mol_type = protein
                        organism = synthetic construct
REGION                  80..84
                        note = The sequence of residues 80 to 84 can be repeated 1
                        to 50 times
SEQUENCE: 56
MRGSHHHHHH GSACELAATA TATATATATA ACGDLAPQML RELQETNAAL QDVRELLRQQ    60
VKEITFLKNT LLEIWKAAKG GGGSLEEQYK TFLDKFMHEL EDLLYQL                 107

SEQ ID NO: 57           moltype = AA  length = 107
FEATURE                 Location/Qualifiers
source                  1..107
                        mol_type = protein
                        organism = synthetic construct
REGION                  80..84
                        note = The sequence of residues 80 to 84 can be repeated 1
                        to 50 times
SEQUENCE: 57
MRGSHHHHHH GSASELAATA TATATATATA ASGDLAPQML RELQETNAAL QDVRELLRQQ    60
VKEITFLKNT LLEIWKAAKG GGGSLEEQYK TFLDKFMHEL EDLLYQL                 107

SEQ ID NO: 58           moltype = AA  length = 104
FEATURE                 Location/Qualifiers
source                  1..104
                        mol_type = protein
```

```
                        organism = synthetic construct
REGION                  80..81
                        note = The sequence of residues 80 to 81 can be repeated 1
                        to 50 times
SEQUENCE: 58
MRGSHHHHHH GSACELAATA TATATATATA ACGDLAPQML RELQETNAAL QDVRELLRQQ    60
VKEITFLKNT LLEIWKAAKA TLEEQYKTFL DKFMHELEDL LYQL                    104

SEQ ID NO: 59           moltype = AA   length = 104
FEATURE                 Location/Qualifiers
source                  1..104
                        mol_type = protein
                        organism = synthetic construct
REGION                  80..81
                        note = The sequence of residues 80 to 81 can be repeated 1
                        to 50 times
SEQUENCE: 59
MRGSHHHHHH GSASELAATA TATATATATA ASGDLAPQML RELQETNAAL QDVRELLRQQ    60
VKEITFLKNT LLEIWKAAKA TLEEQYKTFL DKFMHELEDL LYQL                    104

SEQ ID NO: 60           moltype = AA   length = 113
FEATURE                 Location/Qualifiers
source                  1..113
                        mol_type = protein
                        organism = synthetic construct
SEQUENCE: 60
MRGSHHHHHH GSACELAATA TATATATATA ACGDLAPQML RELQETNAAL QDVRELLRQQ    60
VKEITFLKNT LLEIWKAAKE AAKEAAAKIE EQAKTFLDKF NGEELLRALD QVN          113

SEQ ID NO: 61           moltype = AA   length = 113
FEATURE                 Location/Qualifiers
source                  1..113
                        mol_type = protein
                        organism = synthetic construct
SEQUENCE: 61
MRGSHHHHHH GSASELAATA TATATATATA ASGDLAPQML RELQETNAAL QDVRELLRQQ    60
VKEITFLKNT LLEIWKAAKE AAKEAAAKIE EQAKTFLDKF NGEELLRALD QVN          113

SEQ ID NO: 62           moltype = AA   length = 127
FEATURE                 Location/Qualifiers
source                  1..127
                        mol_type = protein
                        organism = synthetic construct
SEQUENCE: 62
MRGSPKKKRK VGGGGSHHHH HHHHGSACEL AATATATATA TATAACGDLA PQMLRELQET    60
NAALQDVREL LRQQVKEITF LKNTLLEIWK AAKEAAKEAA AKIEEQAKTF LDKFNGEELL   120
RALDQVN                                                             127

SEQ ID NO: 63           moltype = AA   length = 127
FEATURE                 Location/Qualifiers
source                  1..127
                        mol_type = protein
                        organism = synthetic construct
SEQUENCE: 63
MRGSPKKKRK VGGGGSHHHH HHHHGSASEL AATATATATA TATAASGDLA PQMLRELQET    60
NAALQDVREL LRQQVKEITF LKNTLLEIWK AAKEAAKEAA AKIEEQAKTF LDKFNGEELL   120
RALDQVN                                                             127

SEQ ID NO: 64           moltype = AA   length = 109
FEATURE                 Location/Qualifiers
source                  1..109
                        mol_type = protein
                        organism = synthetic construct
REGION                  80..84
                        note = The sequence of residues 80 to 84 can be repeated 1
                        to 50 times
SEQUENCE: 64
MRGSHHHHHH GSACELAATA TATATATATA ACGDLAPQML RELQETNAAL QDVRELLRQQ    60
VKEITFLKNT LLEIWKAAKE AAAKIEEQAK TFLDKFNGEE LLRALDQVN               109

SEQ ID NO: 65           moltype = AA   length = 109
FEATURE                 Location/Qualifiers
source                  1..109
                        mol_type = protein
                        organism = synthetic construct
REGION                  80..84
                        note = The sequence of residues 80 to 84 can be repeated 1
                        to 50 times
SEQUENCE: 65
```

```
MRGSHHHHHH GSASELAATA TATATATATA ASGDLAPQML RELQETNAAL QDVRELLRQQ    60
VKEITFLKNT LLEIWKAAKE AAAKIEEQAK TFLDKFNGEE LLRALDQVN               109

SEQ ID NO: 66            moltype = AA  length = 109
FEATURE                  Location/Qualifiers
source                   1..109
                         mol_type = protein
                         organism = synthetic construct
REGION                   80..84
                         note = The sequence of residues 80 to 84 can be repeated 1
                         to 50 times
SEQUENCE: 66
MRGSHHHHHH GSACELAATA TATATATATA ACGDLAPQML RELQETNAAL QDVRELLRQQ    60
VKEITFLKNT LLEIWKAAKP APAPIEEQAK TFLDKFNGEE LLRALDQVN               109

SEQ ID NO: 67            moltype = AA  length = 109
FEATURE                  Location/Qualifiers
source                   1..109
                         mol_type = protein
                         organism = synthetic construct
REGION                   80..84
                         note = The sequence of residues 80 to 84 can be repeated 1
                         to 50 times
SEQUENCE: 67
MRGSHHHHHH GSASELAATA TATATATATA ASGDLAPQML RELQETNAAL QDVRELLRQQ    60
VKEITFLKNT LLEIWKAAKP APAPIEEQAK TFLDKFNGEE LLRALDQVN               109

SEQ ID NO: 68            moltype = AA  length = 109
FEATURE                  Location/Qualifiers
source                   1..109
                         mol_type = protein
                         organism = synthetic construct
REGION                   80..84
                         note = The sequence of residues 80 to 84 can be repeated 1
                         to 50 times
SEQUENCE: 68
MRGSHHHHHH GSACELAATA TATATATATA ACGDLAPQML RELQETNAAL QDVRELLRQQ    60
VKEITFLKNT LLEIWKAAKG GGGSIEEQAK TFLDKFNGEE LLRALDQVN               109

SEQ ID NO: 69            moltype = AA  length = 109
FEATURE                  Location/Qualifiers
source                   1..109
                         mol_type = protein
                         organism = synthetic construct
REGION                   80..84
                         note = The sequence of residues 80 to 84 can be repeated 1
                         to 50 times
SEQUENCE: 69
MRGSHHHHHH GSASELAATA TATATATATA ASGDLAPQML RELQETNAAL QDVRELLRQQ    60
VKEITFLKNT LLEIWKAAKG GGGSIEEQAK TFLDKFNGEE LLRALDQVN               109

SEQ ID NO: 70            moltype = AA  length = 106
FEATURE                  Location/Qualifiers
source                   1..106
                         mol_type = protein
                         organism = synthetic construct
REGION                   80..81
                         note = The sequence of residues 80 to 81 can be repeated 1
                         to 50 times
SEQUENCE: 70
MRGSHHHHHH GSACELAATA TATATATATA ACGDLAPQML RELQETNAAL QDVRELLRQQ    60
VKEITFLKNT LLEIWKAAKA TIEEQAKTFL DKFNGEELLR ALDQVN                  106

SEQ ID NO: 71            moltype = AA  length = 106
FEATURE                  Location/Qualifiers
source                   1..106
                         mol_type = protein
                         organism = synthetic construct
REGION                   80..81
                         note = The sequence of residues 80 to 81 can be repeated 1
                         to 50 times
SEQUENCE: 71
MRGSHHHHHH GSASELAATA TATATATATA ASGDLAPQML RELQETNAAL QDVRELLRQQ    60
VKEITFLKNT LLEIWKAAKA TIEEQAKTFL DKFNGEELLR ALDQVN                  106

SEQ ID NO: 72            moltype = AA  length = 103
FEATURE                  Location/Qualifiers
source                   1..103
                         mol_type = protein
```

```
                        organism = synthetic construct
SEQUENCE: 72
GSACELAATA TATATATATA ACGDLAPQML RELQETNAAL QDVRELLRQQ VKEITFLKNT    60
LLEIWKAAAK EAAAKEAAAK IEEQAKTFLD KFNHEAEDLF YQS                    103

SEQ ID NO: 73           moltype = AA   length = 103
FEATURE                 Location/Qualifiers
source                  1..103
                        mol_type = protein
                        organism = synthetic construct
SEQUENCE: 73
GSASELAATA TATATATATA ASGDLAPQML RELQETNAAL QDVRELLRQQ VKEITFLKNT    60
LLEIWKAAAK EAAAKEAAAK IEEQAKTFLD KFNHEAEDLF YQS                    103

SEQ ID NO: 74           moltype = AA   length = 98
FEATURE                 Location/Qualifiers
source                  1..98
                        mol_type = protein
                        organism = synthetic construct
REGION                  71..75
                        note = The sequence of residues 71 to 75 can be repeated 1
                        to 50 times
SEQUENCE: 74
GSACELAATA TATATATATA ACGDLAPQML RELQETNAAL QDVRELLRQQ VKEITFLKNT    60
LLEIWKAAAK EAAAKIEEQA KTFLDKFNHE AEDLFYQS                           98

SEQ ID NO: 75           moltype = AA   length = 98
FEATURE                 Location/Qualifiers
source                  1..98
                        mol_type = protein
                        organism = synthetic construct
REGION                  71..75
                        note = The sequence of residues 71 to 75 can be repeated 1
                        to 50 times
SEQUENCE: 75
GSASELAATA TATATATATA ASGDLAPQML RELQETNAAL QDVRELLRQQ VKEITFLKNT    60
LLEIWKAAAK EAAAKIEEQA KTFLDKFNHE AEDLFYQS                           98

SEQ ID NO: 76           moltype = AA   length = 98
FEATURE                 Location/Qualifiers
source                  1..98
                        mol_type = protein
                        organism = synthetic construct
REGION                  71..75
                        note = The sequence of residues 71 to 75 can be repeated 1
                        to 50 times
SEQUENCE: 76
GSACELAATA TATATATATA ACGDLAPQML RELQETNAAL QDVRELLRQQ VKEITFLKNT    60
LLEIWKAAAK PAPAPIEEQA KTFLDKFNHE AEDLFYQS                           98

SEQ ID NO: 77           moltype = AA   length = 98
FEATURE                 Location/Qualifiers
source                  1..98
                        mol_type = protein
                        organism = synthetic construct
REGION                  71..75
                        note = The sequence of residues 71 to 75 can be repeated 1
                        to 50 times
SEQUENCE: 77
GSASELAATA TATATATATA ASGDLAPQML RELQETNAAL QDVRELLRQQ VKEITFLKNT    60
LLEIWKAAAK PAPAPIEEQA KTFLDKFNHE AEDLFYQS                           98

SEQ ID NO: 78           moltype = AA   length = 98
FEATURE                 Location/Qualifiers
source                  1..98
                        mol_type = protein
                        organism = synthetic construct
REGION                  71..75
                        note = The sequence of residues 71 to 75 can be repeated 1
                        to 50 times
SEQUENCE: 78
GSACELAATA TATATATATA ACGDLAPQML RELQETNAAL QDVRELLRQQ VKEITFLKNT    60
LLEIWKAAAK GGGGSIEEQA KTFLDKFNHE AEDLFYQS                           98

SEQ ID NO: 79           moltype = AA   length = 98
FEATURE                 Location/Qualifiers
source                  1..98
                        mol_type = protein
                        organism = synthetic construct
```

```
REGION                  71..75
                        note = The sequence of residues 71 to 75 can be repeated 1
                        to 50 times
SEQUENCE: 79
GSASELAATA TATATATATA ASGDLAPQML RELQETNAAL QDVRELLRQQ VKEITFLKNT    60
LLEIWKAAAK GGGGSIEEQA KTFLDKFNHE AEDLFYQS                           98

SEQ ID NO: 80           moltype = AA  length = 95
FEATURE                 Location/Qualifiers
source                  1..95
                        mol_type = protein
                        organism = synthetic construct
REGION                  71..72
                        note = The sequence of residues 71 to 72 is repeated 1 to
                        50 times
SEQUENCE: 80
GSACELAATA TATATATATA ACGDLAPQML RELQETNAAL QDVRELLRQQ VKEITFLKNT    60
LLEIWKAAAK ATIEEQAKTF LDKFNHEAED LFYQS                              95

SEQ ID NO: 81           moltype = AA  length = 95
FEATURE                 Location/Qualifiers
source                  1..95
                        mol_type = protein
                        organism = synthetic construct
REGION                  71..72
                        note = The sequence of residues to 71 to 72 can be repeated
                        1 to 50 times
SEQUENCE: 81
GSASELAATA TATATATATA ASGDLAPQML RELQETNAAL QDVRELLRQQ VKEITFLKNT    60
LLEIWKAAAK ATIEEQAKTF LDKFNHEAED LFYQS                              95

SEQ ID NO: 82           moltype = AA  length = 101
FEATURE                 Location/Qualifiers
source                  1..101
                        mol_type = protein
                        organism = synthetic construct
SEQUENCE: 82
GSACELAATA TATATATATA ACGDLAPQML RELQETNAAL QDVRELLRQQ VKEITFLKNT    60
LLEIWKAAKE AAKEAAAKLE EQYKTFLDKF MHELEDLLYQ L                      101

SEQ ID NO: 83           moltype = AA  length = 101
FEATURE                 Location/Qualifiers
source                  1..101
                        mol_type = protein
                        organism = synthetic construct
SEQUENCE: 83
GSASELAATA TATATATATA ASGDLAPQML RELQETNAAL QDVRELLRQQ VKEITFLKNT    60
LLEIWKAAKE AAKEAAAKLE EQYKTFLDKF MHELEDLLYQ L                      101

SEQ ID NO: 84           moltype = AA  length = 97
FEATURE                 Location/Qualifiers
source                  1..97
                        mol_type = protein
                        organism = synthetic construct
REGION                  70..74
                        note = The sequence of residues 70 to 74 can be repeated 1
                        to 50 times
SEQUENCE: 84
GSACELAATA TATATATATA ACGDLAPQML RELQETNAAL QDVRELLRQQ VKEITFLKNT    60
LLEIWKAAKE AAAKLEEQYK TFLDKFMHEL EDLLYQL                            97

SEQ ID NO: 85           moltype = AA  length = 97
FEATURE                 Location/Qualifiers
source                  1..97
                        mol_type = protein
                        organism = synthetic construct
REGION                  70..74
                        note = The sequence of residues 70 to 74 can be repeated 1
                        to 50 times
SEQUENCE: 85
GSASELAATA TATATATATA ASGDLAPQML RELQETNAAL QDVRELLRQQ VKEITFLKNT    60
LLEIWKAAKE AAAKLEEQYK TFLDKFMHEL EDLLYQL                            97

SEQ ID NO: 86           moltype = AA  length = 97
FEATURE                 Location/Qualifiers
source                  1..97
                        mol_type = protein
                        organism = synthetic construct
REGION                  70..74
```

```
                        note = The sequence of residues 70 to 74 can be repeated 1
                               to 50 times
SEQUENCE: 86
GSACELAATA TATATATATA ACGDLAPQML RELQETNAAL QDVRELLRQQ VKEITFLKNT    60
LLEIWKAAKP APAPLEEQYK TFLDKFMHEL EDLLYQL                             97

SEQ ID NO: 87           moltype = AA  length = 97
FEATURE                 Location/Qualifiers
source                  1..97
                        mol_type = protein
                        organism = synthetic construct
REGION                  70..74
                        note = The sequence of residues 70 to 74 can be repeated 1
                               to 50 times
SEQUENCE: 87
GSASELAATA TATATATATA ASGDLAPQML RELQETNAAL QDVRELLRQQ VKEITFLKNT    60
LLEIWKAAKP APAPLEEQYK TFLDKFMHEL EDLLYQL                             97

SEQ ID NO: 88           moltype = AA  length = 97
FEATURE                 Location/Qualifiers
source                  1..97
                        mol_type = protein
                        organism = synthetic construct
REGION                  70..74
                        note = The sequence of residues 70 to 74 can be repeated 1
                               to 50 times
SEQUENCE: 88
GSACELAATA TATATATATA ACGDLAPQML RELQETNAAL QDVRELLRQQ VKEITFLKNT    60
LLEIWKAAKG GGGSLEEQYK TFLDKFMHEL EDLLYQL                             97

SEQ ID NO: 89           moltype = AA  length = 97
FEATURE                 Location/Qualifiers
source                  1..97
                        mol_type = protein
                        organism = synthetic construct
REGION                  70..74
                        note = The sequence of residues 70 to 74 can be repeated 1
                               to 50 times
SEQUENCE: 89
GSASELAATA TATATATATA ASGDLAPQML RELQETNAAL QDVRELLRQQ VKEITFLKNT    60
LLEIWKAAKG GGGSLEEQYK TFLDKFMHEL EDLLYQL                             97

SEQ ID NO: 90           moltype = AA  length = 94
FEATURE                 Location/Qualifiers
source                  1..94
                        mol_type = protein
                        organism = synthetic construct
REGION                  70..71
                        note = The sequence of residues 70 to 71 can be repeated 1
                               to 50 times
SEQUENCE: 90
GSACELAATA TATATATATA ACGDLAPQML RELQETNAAL QDVRELLRQQ VKEITFLKNT    60
LLEIWKAAKA TLEEQYKTFL DKFMHELEDL LYQL                                94

SEQ ID NO: 91           moltype = AA  length = 94
FEATURE                 Location/Qualifiers
source                  1..94
                        mol_type = protein
                        organism = synthetic construct
REGION                  70..71
                        note = The sequence of residues 70 to 71 can be repeated 1
                               to 50 times
SEQUENCE: 91
GSASELAATA TATATATATA ASGDLAPQML RELQETNAAL QDVRELLRQQ VKEITFLKNT    60
LLEIWKAAKA TLEEQYKTFL DKFMHELEDL LYQL                                94

SEQ ID NO: 92           moltype = AA  length = 103
FEATURE                 Location/Qualifiers
source                  1..103
                        mol_type = protein
                        organism = synthetic construct
SEQUENCE: 92
GSACELAATA TATATATATA ACGDLAPQML RELQETNAAL QDVRELLRQQ VKEITFLKNT    60
LLEIWKAAKE AAKEAAAKIE EQAKTFLDKF NGEELLRALD QVN                     103

SEQ ID NO: 93           moltype = AA  length = 103
FEATURE                 Location/Qualifiers
source                  1..103
                        mol_type = protein
```

```
SEQUENCE: 93
GSASELAATA TATATATATA ASGDLAPQML RELQETNAAL QDVRELLRQQ VKEITFLKNT    60
LLEIWKAAKE AAKEAAAKIE EQAKTFLDKF NGEELLRALD QVN                    103

SEQ ID NO: 94            moltype = AA   length = 99
FEATURE                  Location/Qualifiers
source                   1..99
                         mol_type = protein
                         organism = synthetic construct
REGION                   70..74
                         note = The sequence of residues 70 to 74 can be repeated 1
                         to 50 times
SEQUENCE: 94
GSACELAATA TATATATATA ACGDLAPQML RELQETNAAL QDVRELLRQQ VKEITFLKNT    60
LLEIWKAAKE AAAKIEEQAK TFLDKFNGEE LLRALDQVN                           99

SEQ ID NO: 95            moltype = AA   length = 99
FEATURE                  Location/Qualifiers
source                   1..99
                         mol_type = protein
                         organism = synthetic construct
REGION                   70..74
                         note = The sequence of residues 70 to 74 can be repeated 1
                         to 50 times
SEQUENCE: 95
GSASELAATA TATATATATA ASGDLAPQML RELQETNAAL QDVRELLRQQ VKEITFLKNT    60
LLEIWKAAKE AAAKIEEQAK TFLDKFNGEE LLRALDQVN                           99

SEQ ID NO: 96            moltype = AA   length = 99
FEATURE                  Location/Qualifiers
source                   1..99
                         mol_type = protein
                         organism = synthetic construct
REGION                   70..74
                         note = The sequence of residues 70 to 74 can be repeated 1
                         to 50 times
SEQUENCE: 96
GSACELAATA TATATATATA ACGDLAPQML RELQETNAAL QDVRELLRQQ VKEITFLKNT    60
LLEIWKAAKP APAPIEEQAK TFLDKFNGEE LLRALDQVN                           99

SEQ ID NO: 97            moltype = AA   length = 99
FEATURE                  Location/Qualifiers
source                   1..99
                         mol_type = protein
                         organism = synthetic construct
REGION                   70..74
                         note = The sequence of residues 70 to 74 can be repeated 1
                         to 50 times
SEQUENCE: 97
GSASELAATA TATATATATA ASGDLAPQML RELQETNAAL QDVRELLRQQ VKEITFLKNT    60
LLEIWKAAKP APAPIEEQAK TFLDKFNGEE LLRALDQVN                           99

SEQ ID NO: 98            moltype = AA   length = 99
FEATURE                  Location/Qualifiers
source                   1..99
                         mol_type = protein
                         organism = synthetic construct
REGION                   70..74
                         note = The sequence of residues 70 to 74 can be repeated 1
                         to 50 times
SEQUENCE: 98
GSACELAATA TATATATATA ACGDLAPQML RELQETNAAL QDVRELLRQQ VKEITFLKNT    60
LLEIWKAAKG GGGSIEEQAK TFLDKFNGEE LLRALDQVN                           99

SEQ ID NO: 99            moltype = AA   length = 99
FEATURE                  Location/Qualifiers
source                   1..99
                         mol_type = protein
                         organism = synthetic construct
REGION                   70..74
                         note = The sequence of residues 70 to 74 can be repeated 1
                         to 50 times
SEQUENCE: 99
GSASELAATA TATATATATA ASGDLAPQML RELQETNAAL QDVRELLRQQ VKEITFLKNT    60
LLEIWKAAKG GGGSIEEQAK TFLDKFNGEE LLRALDQVN                           99

SEQ ID NO: 100           moltype = AA   length = 96
FEATURE                  Location/Qualifiers
```

```
                        source          1..96
                                        mol_type = protein
                                        organism = synthetic construct
                        REGION          70..71
                                        note = The sequence of residues 70 to 71 can be repeated 1
                                        to 50 times
SEQUENCE: 100
GSACELAATA TATATATATA ACGDLAPQML RELQETNAAL QDVRELLRQQ VKEITFLKNT    60
LLEIWKAAKA TIEEQAKTFL DKFNGEELLR ALDQVN                              96

SEQ ID NO: 101          moltype = AA  length = 96
FEATURE                 Location/Qualifiers
source                  1..96
                        mol_type = protein
                        organism = synthetic construct
REGION                  70..71
                        note = The sequence of residues 70 to 71 can be repeated 1
                        to 50 times
SEQUENCE: 101
GSASELAATA TATATATATA ASGDLAPQML RELQETNAAL QDVRELLRQQ VKEITFLKNT    60
LLEIWKAAKA TIEEQAKTFL DKFNGEELLR ALDQVN                              96

SEQ ID NO: 102          moltype = AA  length = 23
FEATURE                 Location/Qualifiers
source                  1..23
                        mol_type = protein
                        organism = synthetic construct
SEQUENCE: 102
GSACELAATA TATATATATA ACG                                            23

SEQ ID NO: 103          moltype = AA  length = 23
FEATURE                 Location/Qualifiers
source                  1..23
                        mol_type = protein
                        organism = synthetic construct
SEQUENCE: 103
GSASELAATA TATATATATA ASG                                            23

SEQ ID NO: 104          moltype = AA  length = 80
FEATURE                 Location/Qualifiers
source                  1..80
                        mol_type = protein
                        organism = synthetic construct
SEQUENCE: 104
DLAPQMLREL QETNAALQDV RELLRQQVKE ITFLKNTLLE IWKAAAKEAA AKEAAAKIEE    60
QAKTFLDKFN HEAEDLFYQS                                                80

SEQ ID NO: 105          moltype = AA  length = 75
FEATURE                 Location/Qualifiers
source                  1..75
                        mol_type = protein
                        organism = synthetic construct
REGION                  48..52
                        note = The sequence of residues 48 to 52 can be repeated 1
                        to 50 times
SEQUENCE: 105
DLAPQMLREL QETNAALQDV RELLRQQVKE ITFLKNTLLE IWKAAAKEAA AKIEEQAKTF    60
LDKFNHEAED LFYQS                                                     75

SEQ ID NO: 106          moltype = AA  length = 75
FEATURE                 Location/Qualifiers
source                  1..75
                        mol_type = protein
                        organism = synthetic construct
REGION                  48..52
                        note = The sequence of residues 48 to 52 are repeated 1 to
                        50 times
SEQUENCE: 106
DLAPQMLREL QETNAALQDV RELLRQQVKE ITFLKNTLLE IWKAAAKPAP APIEEQAKTF    60
LDKFNHEAED LFYQS                                                     75

SEQ ID NO: 107          moltype = AA  length = 75
FEATURE                 Location/Qualifiers
source                  1..75
                        mol_type = protein
                        organism = synthetic construct
REGION                  48..52
                        note = The sequence of residues 48 to 52 can be repeated 1
                        to 50 times
```

```
SEQUENCE: 107
DLAPQMLREL QETNAALQDV RELLRQQVKE ITFLKNTLLE IWKAAAKGGG GSIEEQAKTF    60
LDKFNHEAED LFYQS                                                    75

SEQ ID NO: 108          moltype = AA  length = 72
FEATURE                 Location/Qualifiers
source                  1..72
                        mol_type = protein
                        organism = synthetic construct
REGION                  48..49
                        note = The sequence of residues 48 to 49 can be repeated 1
                        to 50 times
SEQUENCE: 108
DLAPQMLREL QETNAALQDV RELLRQQVKE ITFLKNTLLE IWKAAAKATI EEQAKTFLDK    60
FNHEAEDLFY QS                                                       72

SEQ ID NO: 109          moltype = AA  length = 78
FEATURE                 Location/Qualifiers
source                  1..78
                        mol_type = protein
                        organism = synthetic construct
SEQUENCE: 109
DLAPQMLREL QETNAALQDV RELLRQQVKE ITFLKNTLLE IWKAAKEAAK EAAAKLEEQY    60
KTFLDKFMHE LEDLLYQL                                                 78

SEQ ID NO: 110          moltype = AA  length = 74
FEATURE                 Location/Qualifiers
source                  1..74
                        mol_type = protein
                        organism = synthetic construct
REGION                  47..51
                        note = The sequence of residues 47 to 51 can be repeated 1
                        to 50 times
SEQUENCE: 110
DLAPQMLREL QETNAALQDV RELLRQQVKE ITFLKNTLLE IWKAAKEAAA KLEEQYKTFL    60
DKFMHELEDL LYQL                                                     74

SEQ ID NO: 111          moltype = AA  length = 74
FEATURE                 Location/Qualifiers
source                  1..74
                        mol_type = protein
                        organism = synthetic construct
REGION                  47..51
                        note = The sequence of residues 47 to 51 can be repeated 1
                        to 50 times
SEQUENCE: 111
DLAPQMLREL QETNAALQDV RELLRQQVKE ITFLKNTLLE IWKAAKPAPA PLEEQYKTFL    60
DKFMHELEDL LYQL                                                     74

SEQ ID NO: 112          moltype = AA  length = 74
FEATURE                 Location/Qualifiers
source                  1..74
                        mol_type = protein
                        organism = synthetic construct
REGION                  47..51
                        note = The sequence of residues 47 to 51 can be repeated 1
                        to 50 times
SEQUENCE: 112
DLAPQMLREL QETNAALQDV RELLRQQVKE ITFLKNTLLE IWKAAKGGGG SLEEQYKTFL    60
DKFMHELEDL LYQL                                                     74

SEQ ID NO: 113          moltype = AA  length = 71
FEATURE                 Location/Qualifiers
source                  1..71
                        mol_type = protein
                        organism = synthetic construct
REGION                  47..48
                        note = The sequence of residues 47 to 48 can be repeated 1
                        to 50 times
SEQUENCE: 113
DLAPQMLREL QETNAALQDV RELLRQQVKE ITFLKNTLLE IWKAAKATLE EQYKTFLDKF    60
MHELEDLLYQ L                                                        71

SEQ ID NO: 114          moltype = AA  length = 80
FEATURE                 Location/Qualifiers
source                  1..80
                        mol_type = protein
                        organism = synthetic construct
SEQUENCE: 114
```

```
DLAPQMLREL QETNAALQDV RELLRQQVKE ITFLKNTLLE IWKAAKEAAK EAAAKIEEQA    60
KTFLDKFNGE ELLRALDQVN                                                80

SEQ ID NO: 115          moltype = AA  length = 76
FEATURE                 Location/Qualifiers
source                  1..76
                        mol_type = protein
                        organism = synthetic construct
REGION                  47..51
                        note = The sequence of residues 47 to 51 can be repeated 1
                        to 50 times
SEQUENCE: 115
DLAPQMLREL QETNAALQDV RELLRQQVKE ITFLKNTLLE IWKAAKEAAA KIEEQAKTFL    60
DKFNGEELLR ALDQVN                                                    76

SEQ ID NO: 116          moltype = AA  length = 76
FEATURE                 Location/Qualifiers
source                  1..76
                        mol_type = protein
                        organism = synthetic construct
REGION                  47..51
                        note = The sequence of residues 47 to 51 can be repeated 1
                        to 50 times
SEQUENCE: 116
DLAPQMLREL QETNAALQDV RELLRQQVKE ITFLKNTLLE IWKAAKPAPA PIEEQAKTFL    60
DKFNGEELLR ALDQVN                                                    76

SEQ ID NO: 117          moltype = AA  length = 76
FEATURE                 Location/Qualifiers
source                  1..76
                        mol_type = protein
                        organism = synthetic construct
REGION                  47..51
                        note = The sequence of residues 47 to 51 can be repeated 1
                        to 50 times
SEQUENCE: 117
DLAPQMLREL QETNAALQDV RELLRQQVKE ITFLKNTLLE IWKAAKGGGG SIEEQAKTFL    60
DKFNGEELLR ALDQVN                                                    76

SEQ ID NO: 118          moltype = AA  length = 73
FEATURE                 Location/Qualifiers
source                  1..73
                        mol_type = protein
                        organism = synthetic construct
REGION                  47..48
                        note = The sequence of residues 47 to 48 can be repeated 1
                        to 50 times
SEQUENCE: 118
DLAPQMLREL QETNAALQDV RELLRQQVKE ITFLKNTLLE IWKAAKATIE EQAKTFLDKF    60
NGEELLRALD QVN                                                       73

SEQ ID NO: 119          moltype = AA  length = 10
FEATURE                 Location/Qualifiers
source                  1..10
                        mol_type = protein
                        organism = synthetic construct
SEQUENCE: 119
MRGSHHHHHH                                                           10

SEQ ID NO: 120          moltype = AA  length = 33
FEATURE                 Location/Qualifiers
source                  1..33
                        mol_type = protein
                        organism = synthetic construct
SEQUENCE: 120
MRGSHHHHHH GSASELAATA TATATATATA ASG                                 33

SEQ ID NO: 121          moltype = AA  length = 33
FEATURE                 Location/Qualifiers
source                  1..33
                        mol_type = protein
                        organism = synthetic construct
SEQUENCE: 121
MRGSHHHHHH GSASELAATA TATATATATA ACG                                 33

SEQ ID NO: 122          moltype = AA  length = 49
FEATURE                 Location/Qualifiers
source                  1..49
                        mol_type = protein
```

```
                                    organism = synthetic construct
SEQUENCE: 122
GDLAPQMLRE LQETNAALQD VRELLRQQVK EITFLKNTVM ECDACGKLN              49

SEQ ID NO: 123          moltype = AA   length = 49
FEATURE                 Location/Qualifiers
source                  1..49
                        mol_type = protein
                        organism = synthetic construct
SEQUENCE: 123
GDLAPQMLRE LQETNAALQD VRELLRQQVK EITFLKNTVM ESDASGKLN              49

SEQ ID NO: 124          moltype = AA   length = 49
FEATURE                 Location/Qualifiers
source                  1..49
                        mol_type = protein
                        organism = synthetic construct
SEQUENCE: 124
GDLAPQMLRE AQETNAALQD VRELLRQQVK EITFLKNTVM ESDASGKLN              49

SEQ ID NO: 125          moltype = AA   length = 56
FEATURE                 Location/Qualifiers
source                  1..56
                        mol_type = protein
                        organism = synthetic construct
SEQUENCE: 125
GDLAPQMLRE LQEANAALQD VRELLRQQVK EITFLKNTVM ESDASGKLNS EQIDNO      56

SEQ ID NO: 126          moltype = AA   length = 49
FEATURE                 Location/Qualifiers
source                  1..49
                        mol_type = protein
                        organism = synthetic construct
SEQUENCE: 126
GDLAPQMLRE LQETNAAAQD VRELLRQQVK EITFLKNTVM ESDASGKLN              49

SEQ ID NO: 127          moltype = AA   length = 49
FEATURE                 Location/Qualifiers
source                  1..49
                        mol_type = protein
                        organism = synthetic construct
SEQUENCE: 127
GDLAPQMLRE LQETNAALQD ARELLRQQVK EITFLKNTVM ESDASGKLN              49

SEQ ID NO: 128          moltype = AA   length = 49
FEATURE                 Location/Qualifiers
source                  1..49
                        mol_type = protein
                        organism = synthetic construct
SEQUENCE: 128
GDLAPQMLRE LQETNAALQD VRELARQQVK EITFLKNTVM ESDASGKLN              49

SEQ ID NO: 129          moltype = AA   length = 49
FEATURE                 Location/Qualifiers
source                  1..49
                        mol_type = protein
                        organism = synthetic construct
SEQUENCE: 129
GDLAPQMLRE LQETNAALQD VRELLRQAVK EITFLKNTVM ESDASGKLN              49

SEQ ID NO: 130          moltype = AA   length = 49
FEATURE                 Location/Qualifiers
source                  1..49
                        mol_type = protein
                        organism = synthetic construct
SEQUENCE: 130
GDLAPQMLRE LQETNAALQD VRELLRQQVK EATFLKNTVM ESDASGKLN              49

SEQ ID NO: 131          moltype = AA   length = 49
FEATURE                 Location/Qualifiers
source                  1..49
                        mol_type = protein
                        organism = synthetic construct
SEQUENCE: 131
GDLAPQMLRE LQETNAALQD VRELLRQQVK EITFAKNTVM ESDASGKLN              49

SEQ ID NO: 132          moltype = AA   length = 49
FEATURE                 Location/Qualifiers
source                  1..49
```

```
                        mol_type = protein
                        organism = synthetic construct
SEQUENCE: 132
GDLAPQMLRE LQETNAALQD VRELLRQQVK EITFLKNTAM ESDASGKLN              49

SEQ ID NO: 133          moltype = AA  length = 49
FEATURE                 Location/Qualifiers
source                  1..49
                        mol_type = protein
                        organism = synthetic construct
SEQUENCE: 133
GDLAPQMLRE LQETNAALQD VRELLRQQVK EITFLKNTVM EADASGKLN              49

SEQ ID NO: 134          moltype = AA  length = 45
FEATURE                 Location/Qualifiers
source                  1..45
                        mol_type = protein
                        organism = synthetic construct
SEQUENCE: 134
MDLAPQMLRE LQETNAALQD VRELLRQQVK EITFLKNTVM ECDAC                  45

SEQ ID NO: 135          moltype = AA  length = 35
FEATURE                 Location/Qualifiers
source                  1..35
                        mol_type = protein
                        organism = synthetic construct
SEQUENCE: 135
VKEITFLKNT APQMLRELQE TNAALQDVRE LLRQQ                             35

SEQ ID NO: 136          moltype = AA  length = 38
FEATURE                 Location/Qualifiers
source                  1..38
                        mol_type = protein
                        organism = synthetic construct
SEQUENCE: 136
VKEITFLKNT APQMLRELQE TNAALQDVRE LLRQQSKL                          38

SEQ ID NO: 137          moltype = AA  length = 46
FEATURE                 Location/Qualifiers
source                  1..46
                        mol_type = protein
                        organism = synthetic construct
SEQUENCE: 137
GDLAPQMLRE LQETNAALQD VRELLRQQVK EITFLKNTVM ECDACG                 46

SEQ ID NO: 138          moltype = AA  length = 46
FEATURE                 Location/Qualifiers
source                  1..46
                        mol_type = protein
                        organism = synthetic construct
SEQUENCE: 138
GDLAPQMLRE LQETNAALQD VRELLRQIVK EITFLKNTVM ECDACG                 46

SEQ ID NO: 139          moltype = AA  length = 46
FEATURE                 Location/Qualifiers
source                  1..46
                        mol_type = protein
                        organism = synthetic construct
SEQUENCE: 139
GDLAPQMLRE LQETNAALQD VRELLRQLVK EITFLKNTVM ECDACG                 46

SEQ ID NO: 140          moltype = AA  length = 15
FEATURE                 Location/Qualifiers
source                  1..15
                        mol_type = protein
                        organism = synthetic construct
REGION                  11..15
                        note = The sequence of residues 11 to 15 can be repeated at
                        least two times
SEQUENCE: 140
LLEIWKAAAK EAAAK                                                   15

SEQ ID NO: 141          moltype = AA  length = 15
FEATURE                 Location/Qualifiers
source                  1..15
                        mol_type = protein
                        organism = synthetic construct
REGION                  11..15
                        note = The sequence of residues 11 to 15 can be repeated at
```

```
                              least 2 times
SEQUENCE: 141
LERYYKEAAK EAAAK                                                              15

SEQ ID NO: 142           moltype = AA  length = 33
FEATURE                  Location/Qualifiers
source                   1..33
                         mol_type = protein
                         organism = synthetic construct
SEQUENCE: 142
MRGSHHHHHH GSACELAATA TATATATATA ACG                                          33

SEQ ID NO: 143           moltype = AA  length = 25
FEATURE                  Location/Qualifiers
source                   1..25
                         mol_type = protein
                         organism = synthetic construct
SEQUENCE: 143
LQAATATATA TATATAVDKP IAASA                                                   25

SEQ ID NO: 144           moltype = AA  length = 19
FEATURE                  Location/Qualifiers
source                   1..19
                         mol_type = protein
                         organism = synthetic construct
SEQUENCE: 144
MRGSHHHHHH GSKPIAASA                                                          19

SEQ ID NO: 145           moltype = AA  length = 6
FEATURE                  Location/Qualifiers
source                   1..6
                         mol_type = protein
                         organism = synthetic construct
SEQUENCE: 145
LEGSGT                                                                         6

SEQ ID NO: 146           moltype = AA  length = 23
FEATURE                  Location/Qualifiers
source                   1..23
                         mol_type = protein
                         organism = synthetic construct
SEQUENCE: 146
LEGSELAATA TATATATATA ACG                                                     23

SEQ ID NO: 147           moltype = AA  length = 25
FEATURE                  Location/Qualifiers
source                   1..25
                         mol_type = protein
                         organism = synthetic construct
SEQUENCE: 147
LQAATATATA TATATAVDKP IAASA                                                   25

SEQ ID NO: 148           moltype = AA  length = 24
FEATURE                  Location/Qualifiers
source                   1..24
                         mol_type = protein
                         organism = synthetic construct
SEQUENCE: 148
LQARGDATAT ATATAVDKPI AASA                                                    24

SEQ ID NO: 149           moltype = AA  length = 223
FEATURE                  Location/Qualifiers
source                   1..223
                         mol_type = protein
                         organism = synthetic construct
SEQUENCE: 149
RVQPTESIVR FPNITNLCPF GEVFNATRFA SVYAWNRKRI SNCVADYSVL YNSASFSTFK              60
CYGVSPTKLN DLCFTNVYAD SFVIRGDEVR QIAPGQTGKI ADYNYKLPDD FTGCVIAWNS             120
NNLDSKVGGN YNYLYRLFRK SNLKPFERDI STEIYQAGST PCNGVEGFNC YFPLQSYGFQ             180
PTNGVGYQPY RVVVLSFELL HAPATVCGPK KSTNLVKNKC VNF                              223

SEQ ID NO: 150           moltype = AA  length = 206
FEATURE                  Location/Qualifiers
source                   1..206
                         mol_type = protein
                         organism = synthetic construct
SEQUENCE: 150
PNITNLCPFG EVFNATRFAS VYAWNRKRIS NCVADYSVLY NSASFSTFKC YGVSPTKLND              60
LCFTNVYADS FVIRGDEVRQ IAPGQTGKIA DYNYKLPDDF TGCVIAWNSN NLDSKVGGNY             120
```

```
NYLYRLFRKS NLKPFERDIS TEIYQAGSTP CNGVEGFNCY FPLQSYGFQP TNGVGYQPYR   180
VVVLSFELLH APATVCGPKK STGTLE                                       206

SEQ ID NO: 151           moltype = AA  length = 196
FEATURE                  Location/Qualifiers
source                   1..196
                         mol_type = protein
                         organism = synthetic construct
SEQUENCE: 151
TNLCPFGEVF NATRFASVYA WNRKRISNCV ADYSVLYNSA SFSTFKCYGV SPTKLNDLCF   60
TNVYADSFVI RGDEVRQIAP GQTGKIADYN YKLPDDFTGC VIAWNSNNLD SKVGGNYNYL  120
YRLFRKSNLK PFERDISTEI YQAGSTPCNG VEGFNCYFPL QSYGFQPTNG VGYQPYRVVV  180
LSFELLHAPA TVCGKK                                                 196

SEQ ID NO: 152           moltype = AA  length = 217
FEATURE                  Location/Qualifiers
source                   1..217
                         mol_type = protein
                         organism = synthetic construct
SEQUENCE: 152
RVVPSGDVVR FPNITNLCPF GEVFNATKFP SVYAWERKKI SNCVADYSVL YNSTFFSTFK   60
CYGVSATKLN DLCFSNVYAD SFVVKGDDVR QIAPGQTGVI ADYNYKLPDD FMGCVLAWNT  120
RNIDATSTGN YNYKYRLFRK SNLKPFERDI STEIYQAGST PCNGVEGFNC YFPLQSYGFQ  180
PTNGVGYQPY RVVVLSFELL NAPATVCGPK LSTDLIK                          217

SEQ ID NO: 153           moltype = AA  length = 32
FEATURE                  Location/Qualifiers
source                   1..32
                         mol_type = protein
                         organism = synthetic construct
SEQUENCE: 153
IYQAGSTPCN GVEGFNCYFP LQSYGFQPTN GV                                32

SEQ ID NO: 154           moltype = AA  length = 27
FEATURE                  Location/Qualifiers
source                   1..27
                         mol_type = protein
                         organism = synthetic construct
SEQUENCE: 154
GDDVRQIAPG QTGVIADYNY KLPDDFM                                      27

SEQ ID NO: 155           moltype = AA  length = 25
FEATURE                  Location/Qualifiers
source                   1..25
                         mol_type = protein
                         organism = synthetic construct
SEQUENCE: 155
NTRNIDATST GNYNYKYRLF RKSNL                                        25

SEQ ID NO: 156           moltype = AA  length = 109
FEATURE                  Location/Qualifiers
source                   1..109
                         mol_type = protein
                         organism = synthetic construct
SEQUENCE: 156
VVKGDDVRQI APGQTGVIAD YNYKLPDDFM GCVLAWNTRN IDATSTGNYN YKYRLFRKSN   60
LKPFERDIST EIYQAGSTPC NGVEGFNCYF PLQSYGFQPT NGVGYQPYR              109

SEQ ID NO: 157           moltype = AA  length = 1236
FEATURE                  Location/Qualifiers
source                   1..1236
                         mol_type = protein
                         organism = synthetic construct
SEQUENCE: 157
SDLDRCTTFD DVQAPNYTQH TSSMRGVYYP DEIFRSDTLY LTQDLFLPFY SNVTGFHTIN   60
HTFGNPVIPF KDGIYFAATE KSNVVRGWVF GSTMNNKSQS VIIINNSTNV VIRACNFELC  120
DNPFFAVSKP MGTQTHTMIF DNAFNCTFEY ISDAFSLDVS EKSGNFKHLR EFVFKNKDGF  180
LYVYKGYQPI DVVRDLPSGF NTLKPIFKLP LGINITNFRA ILTAFSPAQD IWGTSAAAYF  240
VGYLKPTTFM LKYDENGTIT DAVDCSQNPL AELKCSVKSF EIDKGIYQTS NFRVVPSGDV  300
VRFPNITNLC PFGEVFNATK FPSVYAWERK KISNCVADYS VLYNSTFFST FKCYGVSATK  360
LNDLCFSNVY ADSFVVKGDD VRQIAPGQTG VIADYNYKLP DDFMGCVLAW NTRNIDATST  420
GNYNYKYRYL RHGKLRPFER DISNVPFSPD GKPCTPPALN CYWPLNDYGF YTTTGIGYQP  480
YRVVVLSFEL LNAPATVCGP KLSTDLIKNQ CVNFNFNGLT GTGVLTPSSK RFQPFQQFGR  540
DVSDFTDSVR DPKTSEILDI SPCAFGGVSV ITPGTNASSE VAVLYQDVNC TDVSTAIHAD  600
QLTPAWRIYS TGNNVFQTQA GCLIGAEHVD TSYECDIPIG AGICASYHTV SLLRSTSQKS  660
IVAYTMSLGA DSSIAYSNNT IAIPTNFSIS ITTEVMPVSM AKTSVDCNMY ICGDSTECAN  720
LLLQYGSFCT QLNRALSGIA AEQDRNTREV FAQVKQMYKT PTLKYFGGFN FSQILPDPLK  780
PTKRSFIEDL LFNKVTLADA GFMKQYGECL GDINARDLIC AQKFNGLTVL PPLLTDDMIA  840
AYTAALVSGT ATAGWTFGAG AALQIPFAMQ MAYRFNGIGV TQNVLYENQK QIANQFNKAI  900
```

```
SQIQESLTTT STALGKLQDV VNQNAQALNT LVKQLSSNFG AISSVLNDIL SRLDPPEAEV    960
QIDRLITGRL QSLQTYVTQQ LIRAAEIRAS ANLAATKMSE CVLGQSKRVD FCGKGYHLMS   1020
FPQAAPHGVV FLHVTYVPSQ ERNFTTAPAI CHEGKAYFPR EGVFVFNGTS WFITQRNFFS   1080
PQIITTDNTF VSGNCDVVIG IINNTVYDPL QPELDSFKEE LDKYFKNHTS PDVDLGDISG   1140
INASVVNIQK EIDRLNEVAK NLNESLIDLQ ELGKYEQGSG YIPEAPRDGQ AYVRKDGEWV   1200
LLSTFLGRSL EVLFQGPGHH HHHHHHSAWS HPQFEK                             1236

SEQ ID NO: 158          moltype = AA  length = 814
FEATURE                 Location/Qualifiers
source                  1..814
                        mol_type = protein
                        organism = synthetic construct
SEQUENCE: 158
MRSSSSWLLL SLVAVTAAWS HPQFEKQSTI EEQAKTFLDK FNHEAEDLFY QSSLASWNYN    60
TNITEENVQN MNNAGDKWSA FLKEQSTLAQ MYPLQEIQNL TVKLQLQALQ QNGSSVLSED   120
KSKRLNTILN TMSTIYSTGK VCNPDNPQEC LLLEPGLNEI MANSLDYNER LWAWESWRSE   180
VGKQLRPLYE EYVVLKNEMA RANHYEDYGD YWRGDYEVNG VDGYDYSRGQ LIEDVEHTFE   240
EIKPLYEHLH AYVRAKLMNA YPSYISPIGC LPAHLLGDMW GRFWTNLYSL TVPFGQKPNI   300
DVTDAMVDQA WDAQRIFKEA EKFFVSVGLP NMTQGFWENS MLTDPGNVQK AVCHPTAWDL   360
GKGDFRILMC TKVTMDDFLT AHHEMGHIQY DMAYAAQPFL LRNGANEGFH EAVGEIMSLS   420
AATPKHLKSI GLLSPDFQED NETEINFLLK QALTIVGTLP FTYMLEKWRW MVFKGEIPKD   480
QWMKKWWEMK REIVGVVEPV PHDETYCDPA SLFHVSNDYS FIRYYTRTLY QFQFQEALCQ   540
AAKHEGPLHK CDISNSTEAG QKLFNMLRLG KSEPWTLALE NVVGAKNMNV RPLLNYFEPL   600
FTWLKDQNKN SFVGWSTDWS PYADQSIKVR ISLKSALGDK AYEWNDNEMY LFRSSVAYAM   660
RQYFLKVKNQ MILFGEEDVR VANLKPRISF NFFVTAPKNV SDIIPRTEVE KAIRMSRSRI   720
NDAFRLNDNS LEFLGIQPTL GPPNQPPVSI WLIVFGVVMG VIVVGIVILI FTGIRDRKKK   780
NKARSGENPY ASIDISKGEN NPGFQNTDDV QTSF                               814

SEQ ID NO: 159          moltype = AA  length = 23
FEATURE                 Location/Qualifiers
source                  1..23
                        mol_type = protein
                        organism = synthetic construct
SEQUENCE: 159
IEEQAKTFLD KFNHEAEDLF YQS                                            23

SEQ ID NO: 160          moltype = AA  length = 28
FEATURE                 Location/Qualifiers
source                  1..28
                        mol_type = protein
                        organism = synthetic construct
SEQUENCE: 160
TEENVQNMNN AGDKWSAFLK EQSTLAQM                                       28

SEQ ID NO: 161          moltype = AA  length = 92
FEATURE                 Location/Qualifiers
source                  1..92
                        mol_type = protein
                        organism = synthetic construct
SEQUENCE: 161
MRSSSSWLLL SLVAVTAAWS HPQFEKQSTI EEQAKTFLDK FNHEAEDLFY QSSLASWNYN    60
TNITEENVQN MNNAGDKWSA FLKEQSTLAQ MY                                  92

SEQ ID NO: 162          moltype = AA  length = 117
FEATURE                 Location/Qualifiers
source                  1..117
                        mol_type = protein
                        organism = synthetic construct
SEQUENCE: 162
MRSSSSWLLL SLVAVTAAWS HPQFEKQSTI EEQAKTFLDK FNHEAEDLFY QSSLASWNYN    60
TNITEENVQN MNNAGDKWSA FLKEQSTLAQ MYPLQEIQNL TVKLQLQALQ QNGSSVL      117

SEQ ID NO: 163          moltype = AA  length = 123
FEATURE                 Location/Qualifiers
source                  1..123
                        mol_type = protein
                        organism = synthetic construct
REGION                  94..98
                        note = The sequence of residues 94 to 98 can be repeated 1
                        to 50 times
SEQUENCE: 163
MRGSPKKKRK VGGGGSHHHH HHHHGSACEL AATATATATA TATAACGDLA PQMLRELQET    60
NAALQDVREL RQQVKEITFL KNTLLEIWKA AKEAAAKIE EQAKTFLDKF NGEELLRALD    120
QVN                                                                 123

SEQ ID NO: 164          moltype = AA  length = 123
FEATURE                 Location/Qualifiers
source                  1..123
                        mol_type = protein
```

```
                         organism = synthetic construct
REGION                   94..98
                         note = The sequence of residues 94 to 98 can be repeated 1
                           to 50 times
SEQUENCE: 164
MRGSPKKKRK VGGGGSHHHH HHHHGSASEL AATATATATA TATAASGDLA PQMLRELQET    60
NAALQDVREL LRQQVKEITF LKNTLLEIWK AAKEAAAKIE EQAKTFLDKF NGEELLRALD   120
QVN                                                                123

SEQ ID NO: 165           moltype = AA  length = 123
FEATURE                  Location/Qualifiers
source                   1..123
                         mol_type = protein
                         organism = synthetic construct
REGION                   94..98
                         note = The sequence of residues 94 to 98 can be repeated 1
                           to 50 times
SEQUENCE: 165
MRGSPKKKRK VGGGGSHHHH HHHHGSACEL AATATATATA TATAACGDLA PQMLRELQET    60
NAALQDVREL LRQQVKEITF LKNTLLEIWK AAKPAPAPIE EQAKTFLDKF NGEELLRALD   120
QVN                                                                123

SEQ ID NO: 166           moltype = AA  length = 123
FEATURE                  Location/Qualifiers
source                   1..123
                         mol_type = protein
                         organism = synthetic construct
REGION                   94..98
                         note = The sequence of residues 94 to 98 can be repeated 1
                           to 50 times
SEQUENCE: 166
MRGSPKKKRK VGGGGSHHHH HHHHGSASEL AATATATATA TATAASGDLA PQMLRELQET    60
NAALQDVREL LRQQVKEITF LKNTLLEIWK AAKPAPAPIE EQAKTFLDKF NGEELLRALD   120
QVN                                                                123

SEQ ID NO: 167           moltype = AA  length = 123
FEATURE                  Location/Qualifiers
source                   1..123
                         mol_type = protein
                         organism = synthetic construct
REGION                   94..98
                         note = The sequence of residues 94 to 98 can be repeated 1
                           to 50 times
SEQUENCE: 167
MRGSPKKKRK VGGGGSHHHH HHHHGSACEL AATATATATA TATAACGDLA PQMLRELQET    60
NAALQDVREL LRQQVKEITF LKNTLLEIWK AAKGGGGSIE EQAKTFLDKF NGEELLRALD   120
QVN                                                                123

SEQ ID NO: 168           moltype = AA  length = 123
FEATURE                  Location/Qualifiers
source                   1..123
                         mol_type = protein
                         organism = synthetic construct
REGION                   94..98
                         note = The sequence of residues 94 to 98 can be repeated 1
                           to 50 times
SEQUENCE: 168
MRGSPKKKRK VGGGGSHHHH HHHHGSASEL AATATATATA TATAASGDLA PQMLRELQET    60
NAALQDVREL LRQQVKEITF LKNTLLEIWK AAKGGGGSIE EQAKTFLDKF NGEELLRALD   120
QVN                                                                123

SEQ ID NO: 169           moltype = AA  length = 120
FEATURE                  Location/Qualifiers
source                   1..120
                         mol_type = protein
                         organism = synthetic construct
REGION                   94..95
                         note = The sequence of residues 94 to 95 can be repeated 1
                           to 50 times
SEQUENCE: 169
MRGSPKKKRK VGGGGSHHHH HHHHGSACEL AATATATATA TATAACGDLA PQMLRELQET    60
NAALQDVREL LRQQVKEITF LKNTLLEIWK AAKATIEEQA KTFLDKFNGE ELLRALDQVN   120

SEQ ID NO: 170           moltype = AA  length = 120
FEATURE                  Location/Qualifiers
source                   1..120
                         mol_type = protein
                         organism = synthetic construct
REGION                   94..95
```

```
                         note = The sequence of residues 94 to 95 can be repeated 1
                                to 50 times
SEQUENCE: 170
MRGSPKKKRK VGGGGSHHHH HHHHGSASEL AATATATATA TATAASGDLA PQMLRELQET    60
NAALQDVREL LRQQVKEITF LKNTLLEIWK AAKATIEEQA KTFLDKFNGE ELLRALDQVN   120

SEQ ID NO: 171           moltype = AA  length = 81
FEATURE                  Location/Qualifiers
source                   1..81
                         mol_type = protein
                         organism = synthetic construct
SEQUENCE: 171
MDLAPQMLRE LQETNAALQD VRELLRQQVK EITFLKNTLL EIWKAAKEAA KEAAAKIEEQ    60
AKTFLDKFNG EELLRALDQV N                                              81

SEQ ID NO: 172           moltype = AA  length = 70
FEATURE                  Location/Qualifiers
source                   1..70
                         mol_type = protein
                         organism = synthetic construct
SEQUENCE: 172
MRGSHHHHHH GSACELAATA TATATATATA ACGDLAPQML RELQETNAAL QDVRELLRQQ    60
VKEITFLKNT                                                           70

SEQ ID NO: 173           moltype = AA  length = 70
FEATURE                  Location/Qualifiers
source                   1..70
                         mol_type = protein
                         organism = synthetic construct
SEQUENCE: 173
MRGSHHHHHH GSASELAATA TATATATATA ASGDLAPQML RELQETNAAL QDVRELLRQQ    60
VKEITFLKNT                                                           70

SEQ ID NO: 174           moltype = AA  length = 76
FEATURE                  Location/Qualifiers
source                   1..76
                         mol_type = protein
                         organism = synthetic construct
SEQUENCE: 174
MRGSHHHHHH GSACELAATA TATATATATA ACGDLAPQML RELQETNAAL QDVRELLRQQ    60
VKEITFLKNT LLEIWK                                                    76

SEQ ID NO: 175           moltype = AA  length = 76
FEATURE                  Location/Qualifiers
source                   1..76
                         mol_type = protein
                         organism = synthetic construct
SEQUENCE: 175
MRGSHHHHHH GSASELAATA TATATATATA ASGDLAPQML RELQETNAAL QDVRELLRQQ    60
VKEITFLKNT LLEIWK                                                    76

SEQ ID NO: 176           moltype = AA  length = 5
FEATURE                  Location/Qualifiers
source                   1..5
                         mol_type = protein
                         organism = synthetic construct
REGION                   5
                         note = The entire sequence can be repeated 1 to 50 times
SEQUENCE: 176
EAAAK                                                                 5

SEQ ID NO: 177           moltype = AA  length = 106
FEATURE                  Location/Qualifiers
source                   1..106
                         mol_type = protein
                         organism = synthetic construct
REGION                   80..83
                         note = The sequence of residues 80 to 83 can be repeated 1
                                to 50 times
SEQUENCE: 177
MRGSHHHHHH GSACELAATA TATATATATA ACGDLAPQML RELQETNAAL QDVRELLRQQ    60
VKEITFLKNT LLEIWKAAKE AAKLEEQYKT FLDKFMHELE DLLYQL                  106

SEQ ID NO: 178           moltype = AA  length = 106
FEATURE                  Location/Qualifiers
source                   1..106
                         mol_type = protein
                         organism = synthetic construct
REGION                   80..83
```

```
                                note = The sequence of residues 80 to 83 can be repeated 1
                                to 50 times
SEQUENCE: 178
MRGSHHHHHH GSASELAATA TATATATATA ASGDLAPQML RELQETNAAL QDVRELLRQQ    60
VKEITFLKNT LLEIWKAAKE AAKLEEQYKT FLDKFMHELE DLLYQL                  106

SEQ ID NO: 179          moltype = AA  length = 108
FEATURE                 Location/Qualifiers
source                  1..108
                        mol_type = protein
                        organism = synthetic construct
REGION                  80..83
                        note = The sequence of residues 80 to 83 can be repeated 1
                        to 50 times
SEQUENCE: 179
MRGSHHHHHH GSACELAATA TATATATATA ACGDLAPQML RELQETNAAL QDVRELLRQQ    60
VKEITFLKNT LLEIWKAAKE AAKIEEQAKT FLDKFNGEEL LRALDQVN                108

SEQ ID NO: 180          moltype = AA  length = 108
FEATURE                 Location/Qualifiers
source                  1..108
                        mol_type = protein
                        organism = synthetic construct
REGION                  80..83
                        note = The sequence of residues 80 to 83 can be repeated 1
                        to 50 times
SEQUENCE: 180
MRGSHHHHHH GSASELAATA TATATATATA ASGDLAPQML RELQETNAAL QDVRELLRQQ    60
VKEITFLKNT LLEIWKAAKE AAKIEEQAKT FLDKFNGEEL LRALDQVN                108

SEQ ID NO: 181          moltype = AA  length = 122
FEATURE                 Location/Qualifiers
source                  1..122
                        mol_type = protein
                        organism = synthetic construct
REGION                  94..97
                        note = The sequence of residues 94 to 97 can be repeated 1
                        to 50 times
SEQUENCE: 181
MRGSPKKKRK VGGGGSHHHH HHHHGSACEL AATATATATA TATAACGDLA PQMLRELQET    60
NAALQDVREL LRQQVKEITF LKNTLLEIWK AAKEAAKIEE QAKTFLDKFN GEELLRALDQ   120
VN                                                                 122

SEQ ID NO: 182          moltype = AA  length = 122
FEATURE                 Location/Qualifiers
source                  1..122
                        mol_type = protein
                        organism = synthetic construct
REGION                  94..97
                        note = The sequence of residues 94 to 97 can be repeated 1
                        to 50 times
SEQUENCE: 182
MRGSPKKKRK VGGGGSHHHH HHHHGSASEL AATATATATA TATAASGDLA PQMLRELQET    60
NAALQDVREL LRQQVKEITF LKNTLLEIWK AAKEAAKIEE QAKTFLDKFN GEELLRALDQ   120
VN                                                                 122

SEQ ID NO: 183          moltype = AA  length = 96
FEATURE                 Location/Qualifiers
source                  1..96
                        mol_type = protein
                        organism = synthetic construct
REGION                  70..73
                        note = The sequence of residues 70 to 73 can be repeated 1
                        to 50 times
SEQUENCE: 183
GSACELAATA TATATATATA ACGDLAPQML RELQETNAAL QDVRELLRQQ VKEITFLKNT    60
LLEIWKAAKE AAKLEEQYKT FLDKFMHELE DLLYQL                             96

SEQ ID NO: 184          moltype = AA  length = 96
FEATURE                 Location/Qualifiers
source                  1..96
                        mol_type = protein
                        organism = synthetic construct
REGION                  70..73
                        note = The sequence of residues 70 to 73 can be repeated 1
                        to 50 times
SEQUENCE: 184
GSASELAATA TATATATATA ASGDLAPQML RELQETNAAL QDVRELLRQQ VKEITFLKNT    60
LLEIWKAAKE AAKLEEQYKT FLDKFMHELE DLLYQL                             96
```

```
SEQ ID NO: 185          moltype = AA  length = 73
FEATURE                 Location/Qualifiers
source                  1..73
                        mol_type = protein
                        organism = synthetic construct
REGION                  47..50
                        note = The sequence of residues 47 to 50 can be repeated 1
                        to 50 times
SEQUENCE: 185
DLAPQMLREL QETNAALQDV RELLRQQVKE ITFLKNTLLE IWKAAKEAAK LEEQYKTFLD   60
KFMHELEDLL YQL                                                     73

SEQ ID NO: 186          moltype = AA  length = 98
FEATURE                 Location/Qualifiers
source                  1..98
                        mol_type = protein
                        organism = synthetic construct
REGION                  70..73
                        note = The sequence of residues 70 to 73 can be repeated 1
                        to 50 times
SEQUENCE: 186
GSACELAATA TATATATATA ACGDLAPQML RELQETNAAL QDVRELLRQQ VKEITFLKNT   60
LLEIWKAAKE AAKIEEQAKT FLDKFNGEEL LRALDQVN                           98

SEQ ID NO: 187          moltype = AA  length = 98
FEATURE                 Location/Qualifiers
source                  1..98
                        mol_type = protein
                        organism = synthetic construct
REGION                  70..73
                        note = The sequence of 70 to 73 can be repeated 1 to 50
                        times
SEQUENCE: 187
GSASELAATA TATATATATA ASGDLAPQML RELQETNAAL QDVRELLRQQ VKEITFLKNT   60
LLEIWKAAKE AAKIEEQAKT FLDKFNGEEL LRALDQVN                           98

SEQ ID NO: 188          moltype = AA  length = 75
FEATURE                 Location/Qualifiers
source                  1..75
                        mol_type = protein
                        organism = synthetic construct
REGION                  47..50
                        note = The sequence of residues 47 to 50 can be repeated 1
                        to 50 times
SEQUENCE: 188
DLAPQMLREL QETNAALQDV RELLRQQVKE ITFLKNTLLE IWKAAKEAAK IEEQAKTFLD   60
KFNGEELLRA LDQVN                                                   75

SEQ ID NO: 189          moltype = AA  length = 14
FEATURE                 Location/Qualifiers
source                  1..14
                        mol_type = protein
                        organism = synthetic construct
SEQUENCE: 189
AAAKEAAAKE AAAK                                                    14

SEQ ID NO: 190          moltype = AA  length = 26
FEATURE                 Location/Qualifiers
source                  1..26
                        mol_type = protein
                        organism = synthetic construct
SEQUENCE: 190
LEEQAKTFLD KFNGEELLRA LQDQVN                                       26
```

The invention claimed is:

1. A protein comprising one or more $X_1$ blocks, $X_2$ blocks, and $X_3$ blocks, wherein the $X_1$ block is a coiled-coil domain, the $X_2$ block is a linker, and the $X_3$ block is a binding domain for a target protein, wherein the $X_1$, $X_2$, and $X_3$ blocks are oriented from the N to C-terminus as $(X_1)_a$-$(X_2)_b$-$(X_3)_c$ or $(X_3)_c$-$(X_2)_b$-$(X_1)_a$, wherein a, b, and c are the number of repeat units for the blocks, wherein a, b, and c are each independently 1 to 50, wherein $X_3$ is IEEQAKTFLDKFNGEELLRALDQVN (SEQ ID NO:39) or a sequence having at least 85% identity thereto and $X_1$ comprises the following sequence:

(SEQ ID NO: 3)
MRGSHHHHHHGSACELAATATATATATATATAACGDLAPQMLRELQETNAAL
QDVRELLRQQVKEITFLKNTLLEIWKAAAK;

(SEQ ID NO: 4)

```
                                              -continued
MRGSHHHHHHGSASELAATATATATATATATAASGDLAPQMLRELQETNAAL
QDVRELLRQQVKEITFLKNTLLEIWKAAAK;

(SEQ ID NO: 5)
MRGSHHHHHHGSACELAATATATATATATATAACGDLAPQMLRELQETNAAL
QDVRELLRQQVKEITFLKNTLLEIWK;

(SEQ ID NO: 6)
MRGSHHHHHHGSASELAATATATATATATATAASGDLAPQMLRELQETNAAL
QDVRELLRQQVKEITFLKNTLLEIWK;

(SEQ ID NO: 172)
MRGSHHHHHHGSACELAATATATATATATATAACGDLAPQMLRELQETNAAL
QDVRELLRQQVKEITFLKNT, (SEQ ID NO: 173)
MRGSHHHHHHGSASELAATATATATATATATAASGDLAPQMLRELQETNAAL
QDVRELLRQQVKEITFLKNT, (SEQ ID NO: 8)
GSACELAATATATATATATATAACGDLAPQMLRELQETNAALQDVRELLRQQ
VKEITFLKNTLLEIWKAAAK;

(SEQ ID NO: 9)
GSASELAATATATATATATATAASGDLAPQMLRELQETNAALQDVRELLRQQ
VKEITFLKNTLLEIWKAAAK;

(SEQ ID NO: 10)
GSACELAATATATATATATATAACGDLAPQMLRELQETNAALQDVRELLRQQ
VKEITFLKNTLLEIWK;

(SEQ ID NO: 11)
GSASELAATATATATATATATAASGDLAPQMLRELQETNAALQDVRELLRQQ
VKEITFLKNTLLEIWK;

(SEQ ID NO: 174)
MRGSHHHHHHGSACELAATATATATATATATAACGDLAPQMLRELQETNAAL
```

```
                                              -continued
QDVRELLRQQVKEITFLKNTLLEIWK, (SEQ ID NO: 175)
MRGSHHHHHHGSASELAATATATATATATATAASGDLAPQMLRELQETNAAL
QDVRELLRQQVKEITFLKNTLLEIWK, (SEQ ID NO: 12)
DLAPQMLRELQETNAALQDVRELLRQQVKEITFLKNTLLEIWKAAAK, (SEQ ID NO: 13)
DLAPQMLRELQETNAALQDVRELLRQQVKEITFLKNTLLEIWK, (SEQ ID NO: 14)
DLAPQMLRELQETNAALQDVRELLRQQVKEITFLKNT,
``` or
a sequence having at least 85% identity with any one of SEQ ID NOs:3-6, 8-14, and 172-175.

2. The protein of claim 1, wherein $X_2$ comprises the following sequence: $(G_4S)_n$ (SEQ ID NO:22), $[EAAAK]_n$, (SEQ ID NO:176), $(EAAK)_n$ (SEQ ID NO:23), $(PAPAP)_n$ (SEQ ID NO:24), $A(EAAAK)_4ALEA(EAAAK)_4A$ (SEQ ID NO:25), AEAAAKEAAAKA (SEQ ID NO:26), $(Ala-Pro)_n$, VSQTSKLTRAETVFPDV (SEQ ID NO:27), PLGLWA (SEQ ID NO:28), RVLAEA (SEQ ID NO:29), EDVVCCSMSY (SEQ ID NO:30), GGIEGRGS (SEQ ID NO:31), TRHRQPRGWE (SEQ ID NO:32), AGNRVRRSVG (SEQ ID NO:33), AAAKEAAAKEAAAK (SEQ ID NO:189), RRRRRRRRR (SEQ ID NO:34), GFLG (SEQ ID NO:37 SEQ ID NO:35), LE, $(G)_n$, a disulfide bridge, or a sequence having at least 75% homology with any one of SEQ ID NOs:22-35, 176, or 189, wherein n is 1-50.

3. The protein of claim 1, wherein the protein comprises one or more of the following sequences:

```
                                             (SEQ ID NO: 60)
MRGSHHHHHHGSACELAATATATATATATATAACGDLAPQMLRELQETNAALQDVRE
LLRQQVKEITFLKNTLLEIWKAAKEAAKEAAAKIEEQAKTFLDKFNGEELL;

(SEQ ID NO: 61)
MRGSHHHHHHGSASELAATATATATATATATAASGDLAPQMLRELQETNAALQDVRE
LLRQQVKEITFLKNTLLEIWKAAKEAAKEAAAKIEEQAKTFLDKFNGEELLRALDQV
N;

(SEQ ID NO: 62)
MRGSPKKKRKVGGGGSHHHHHHHHGSACELAATATATATATATATAACGDLAPQML
RELQETNAALQDVRELLRQQVKEITFLKNTLLEIWKAAKEAAKEAAAKIEEQAKTFL
DKFNGEELLRALDQVN;

(SEQ ID NO: 63)
MRGSPKKKRKVGGGGSHHHHHHHHGSASELAATATATATATATATAASGDLAPQML
RELQETNAALQDVRELLRQQVKEITFLKNTLLEIWKAAKEAAKEAAAKIEEQAKTFL
DKFNGEELLRALDQVN (SEQ ID NO: 64)
MRGSHHHHHHGSACELAATATATATATATATAACGDLAPQMLRELQETNAALQDVRE
LLRQQVKEITFLKNTLLEIWKAAK(EAAAK)ₙIEEQAKTFLDKFNGEELLRALDQVN;

(SEQ ID NO: 65)
MRGSHHHHHHGSASELAATATATATATATATAASGDLAPQMLRELQETNAALQDVRE
LLRQQVKEITFLKNTLLEIWKAAK(EAAAK)ₙIEEQAKTFLDKFNGEELLRALDQVN;

(SEQ ID NO: 66)
MRGSHHHHHHGSACELAATATATATATATATAACGDLAPQMLRELQETNAALQDVRE
LLRQQVKEITFLKNTLLEIWKAAK(PAPAP)ₙIEEQAKTFLDKFNGEELLRALDQVN;

(SEQ ID NO: 67)
MRGSHHHHHHGSASELAATATATATATATATAASGDLAPQMLRELQETNAALQDVRE
LLRQQVKEITFLKNTLLEIWKAAK(PAPAP)ₙIEEQAKTFLDKFNGEELLRALDQVN;

(SEQ ID NO: 68)
MRGSHHHHHHGSACELAATATATATATATATAACGDLAPQMLRELQETNAALQDVRE
LLRQQVKEITFLKNTLLEIWKAAK(GGGGS)ₙIEEQAKTFLDKFNGEELLRALDQVN;

(SEQ ID NO: 69)
```

-continued

MRGSHHHHHHGSASELAATATATATATATAASGDLAPQMLRELQETNAALQDVRE
LLRQQVKEITFLKNTLLEIWKAAK(GGGGS)$_n$IEEQAKTFLDKFNGEELLRALDQVN;

(SEQ ID NO: 70)
MRGSHHHHHHGSACELAATATATATATATAACGDLAPQMLRELQETNAALQDVRE
LLRQQVKEITFLKNTLLEIWKAAK(AT)$_n$IEEQAKTFLDKFNGEELLRALDQVN;

(SEQ ID NO: 71)
MRGSHHHHHHGSASELAATATATATATATAASGDLAPQMLRELQETNAALQDVRE
LLRQQVKEITFLKNTLLEIWKAAK(AT)$_n$ IEEQAKTFLDKFNGEELLRALDQVN;

(SEQ ID NO: 163)
MRGSPKKKRKVGGGGSHHHHHHHGSACELAATATATATATATAACGDLAPQML
RELQETNAALQDVRELLRQQVKEITFLKNTLLEIWKAAK(EAAAK)$_n$IEEQAKTFLDKF
NGEELLRALDQVN;

(SEQ ID NO: 164)
MRGSPKKKRKVGGGGSHHHHHHHGSASELAATATATATATATAASGDLAPQML
RELQETNAALQDVRELLRQQVKEITFLKNTLLEIWKAAK(EAAAK)$_n$IEEQAKTFLDKF
NGEELLRALDQVN;

(SEQ ID NO: 165)
MRGSPKKKRKVGGGGSHHHHHHHGSACELAATATATATATATAACGDLAPQML
RELQETNAALQDVRELLRQQVKEITFLKNTLLEIWKAAK(PAPAP)$_n$IEEQAKTFLDKF
NGEELLRALDQVN;

(SEQ ID NO: 166)
MRGSPKKKRKVGGGGSHHHHHHHGSASELAATATATATATATAASGDLAPQML
RELQETNAALQDVRELLRQQVKEITFLKNTLLEIWKAAK(PAPAP)$_n$IEEQAKTFLDKF
NGEELLRALDQVN;

(SEQ ID NO: 167)
MRGSPKKKRKVGGGGSHHHHHHHGSACELAATATATATATATAACGDLAPQML
RELQETNAALQDVRELLRQQVKEITFLKNTLLEIWKAAK(GGGGS)$_n$IEEQAKTFLDKF
NGEELLRALDQVN;

(SEQ ID NO: 168)
MRGSPKKKRKVGGGGSHHHHHHHGSASELAATATATATATATAASGDLAPQML
RELQETNAALQDVRELLRQQVKEITFLKNTLLEIWKAAK(GGGGS)$_n$IEEQAKTFLDKF
NGEELLRALDQVN;

(SEQ ID NO: 169)
MRGSPKKKRKVGGGGSHHHHHHHGSACELAATATATATATATAACGDLAPQML
RELQETNAALQDVRELLRQQVKEITFLKNTLLEIWKAAK(AT)$_n$IEEQAKTFLDKFNGE
ELLRALDQVN;

(SEQ ID NO: 170)
MRGSPKKKRKVGGGGSHHHHHHHGSASELAATATATATATATAASGDLAPQML
RELQETNAALQDVRELLRQQVKEITFLKNTLLEIWKAAK(AT)$_n$IEEQAKTFLDKFNGE
ELLRALDQVN;

(SEQ ID NO: 92)
GSACELAATATATATATATAACGDLAPQMLRELQETNAALQDVRELLRQQVKEITF
LKNTLLEIWKAAKEAAKEAAAKIEEQAKTFLDKFNGEELLRALDQVN;

(SEQ ID NO: 93)
GSASELAATATATATATATAASGDLAPQMLRELQETNAALQDVRELLRQQVKEITFL
KNTLLEIWKAAKEAAKEAAAKIEEQAKTFLDKFNGEELLRALDQVN;

(SEQ ID NO: 94)
GSACELAATATATATATATAACGDLAPQMLRELQETNAALQDVRELLRQQVKEITF
LKNTLLEIWKAAK(EAAAK)$_n$IEEQAKTFLDKFNGEELLRALDQVN;

(SEQ ID NO: 95)
GSASELAATATATATATATAASGDLAPQMLRELQETNAALQDVRELLRQQVKEITFL
KNTLLEIWKAAK(EAAAK)$_n$IEEQAKTFLDKFNGEELLRALDQVN;

(SEQ ID NO: 96)
GSACELAATATATATATATAACGDLAPQMLRELQETNAALQDVRELLRQQVKEITF
LKNTLLEIWKAAK(PAPAP)$_n$IEEQAKTFLDKFNGEELLRALDQVN;

(SEQ ID NO: 97)
GSASELAATATATATATATAASGDLAPQMLRELQETNAALQDVRELLRQQVKEITFL
KNTLLEIWKAAK(PAPAP)$_n$IEEQAKTFLDKFNGEELLRALDQVN;

(SEQ ID NO: 98)
GSACELAATATATATATATAACGDLAPQMLRELQETNAALQDVRELLRQQVKEITF
LKNTLLEIWKAAK(GGGGS)$_n$IEEQAKTFLDKFNGEELLRALDQVN;

(SEQ ID NO: 99)
GSASELAATATATATATATAASGDLAPQMLRELQETNAALQDVRELLRQQVKEITFL

-continued

KNTLLEIWKAAK(GGGGS)$_n$IEEQAKTFLDKFNGEELLRALDQVN;

(SEQ ID NO: 100)
GSACELAATATATATATATAACGDLAPQMLRELQETNAALQDVRELLRQQVKEITF
LKNTLLEIWKAAK(AT)$_n$IEEQAKTFLDKFNGEELLRALDQVN;

(SEQ ID NO: 101)
GSASELAATATATATATATAASGDLAPQMLRELQETNAALQDVRELLRQQVKEITFL
KNTLLEIWKAAK(AT)$_n$IEEQAKTFLDKFNGEELLRALDQVN;

(SEQ ID NO: 114)
DLAPQMLRELQETNAALQDVRELLRQQVKEITFLKNTLLEIWKAAKEAAKEAAAKI
EEQAKTFLDKFNGEELLRALDQVN (SEQ ID NO: 115)
DLAPQMLRELQETNAALQDVRELLRQQVKEITFLKNTLLEIWKAAK(EAAAK)$_n$IEEQ
AKTFLDKFNGEELLRALDQVN;

(SEQ ID NO: 116)
DLAPQMLRELQETNAALQDVRELLRQQVKEITFLKNTLLEIWKAAK(PAPAP)$_n$IEEQA
KTFLDKFNGEELLRALDQVN;

(SEQ ID NO: 117)
DLAPQMLRELQETNAALQDVRELLRQQVKEITFLKNTLLEIWKAAK(GGGGS)$_n$IEEQ
AKTFLDKFNGEELLRALDQVN;
or (SEQ ID NO: 118)
DLAPQMLRELQETNAALQDVRELLRQQVKEITFLKNTLLEIWKAAK(AT)$_n$IEEQAKT
FLDKFNGEELLRALDQVN, wherein n is 1-50.

4. A multivalent target-binding oligomer comprising a plurality of proteins of claim 1.

5. The multivalent target-binding oligomer of claim 4, wherein the oligomer is a pentamer.

6. The multivalent target-binding oligomer of claim 4, wherein the oligomer is a trimer or tetramer.

7. A method for treatment of SARS-CoV-2 infection and/or cancer and/or a disease and/or a viral infection in a subject in need of treatment, comprising administering to the subject in need of treatment a composition comprising a therapeutically effective amount of the multivalent target-binding oligomer of claim 4.

8. The method of claim 7, wherein the subject in need of treatment is symptomatic or asymptomatic of the SARS-CoV-2 infection, wherein the SARS-CoV-2 infection is caused by a SARS-CoV-2 variant alpha, beta, delta, gamma, epsilon, eta, iota, kappa, mu, and/or zeta.

9. A method of reducing the severity of an already contracted SARS-CoV-2 infection, or an expected SARS-CoV-2 infection comprising administering to the subject a composition comprising the multivalent target-binding oligomer of claim 4.

10. The method of claim 9, wherein the SARS-CoV-2 infection is caused by a SARS-CoV-2 variant alpha, beta, delta, gamma, epsilon, eta, iota, kappa, mu, and/or zeta.

* * * * *